(12) United States Patent
Puerta et al.

(10) Patent No.: US 7,786,316 B2
(45) Date of Patent: Aug. 31, 2010

(54) METALLOPROTEIN INHIBITORS

(75) Inventors: David T. Puerta, Melrose, MA (US); Seth M. Cohen, San Marcos, CA (US); Jana A. Lewis, La Jolla, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 12/503,190

(22) Filed: Jul. 15, 2009

(65) Prior Publication Data

US 2009/0286987 A1  Nov. 19, 2009

Related U.S. Application Data

(60) Division of application No. 11/554,478, filed on Oct. 30, 2006, now Pat. No. 7,579,486, and a continuation-in-part of application No. PCT/US2005/014747, filed on Apr. 28, 2005, and a continuation-in-part of application No. PCT/US2005/009277, filed on Mar. 21, 2005.

(60) Provisional application No. 60/566,882, filed on Apr. 29, 2004, provisional application No. 60/576,444, filed on Jun. 3, 2004, provisional application No. 60/826,488, filed on Sep. 21, 2006.

(51) Int. Cl.
*C07D 315/00* (2006.01)
*C07D 211/72* (2006.01)

(52) U.S. Cl. ........................ 549/418; 546/290

(58) Field of Classification Search ................ 546/290; 549/417, 418
See application file for complete search history.

(56) References Cited

U.S. PATENT DOCUMENTS

| | | | |
|---|---|---|---|
| 4,585,780 | A | 4/1986 | Hider et al. |
| 5,981,496 | A | 11/1999 | Cohen et al. |
| 6,552,073 | B1 | 4/2003 | Leblanc et al. |
| 6,825,204 | B2 | 11/2004 | Liu |
| 6,932,960 | B2 | 8/2005 | Liu |
| 7,579,486 | B2 | 8/2009 | Puerta et al. |
| 7,705,164 | B2 | 4/2010 | Puerta et al. |
| 2004/0063673 | A1 | 4/2004 | Johnson |
| 2007/0117848 | A1 | 5/2007 | Puerta et al. |
| 2008/0103129 | A1 | 5/2008 | Zhang et al. |
| 2008/0161362 | A1 | 7/2008 | Puerta et al. |
| 2010/0173952 | | 7/2010 | Puerta et al. |

FOREIGN PATENT DOCUMENTS

| EP | 1006112 A1 | 6/2000 |
|---|---|---|
| WO | WO-2004/110442 A1 | 12/2004 |
| WO | WO-2005/110399 A2 | 11/2005 |
| WO | WO-2006/028523 A2 | 3/2006 |

OTHER PUBLICATIONS

"U.S. Appl. No. 11/554,475, Preliminary Amendment filed Oct. 22, 2007", 7 pgs.
"U.S. Appl. No. 11/554,475, Response filed Jan. 9, 2009 to Final Office Action mailed Nov. 12, 2008", 17 pgs.
"U.S. Appl. No. 11/554,475, Final Office Action mailed Feb. 4, 2009", 7 pgs.
"U.S. Appl. No. 11/554,475, Advisory Action mailed May 15, 2009", 3 pgs.
"U.S. Appl. No. 11/554,475, Final Office Action mailed Nov. 12, 2008", 11 pgs.
"U.S. Appl. No. 11/554,475, Interview Summary of Jun. 3, 2008", 1 pg.
"U.S. Appl. No. 11/554,475, Non-Final Office Action mailed Jun. 19, 2008", 10 pgs.
"U.S. Appl. No. 11/554,475, Notice of Allowance mailed Jun. 3, 2009", 6 pgs.
"U.S. Appl. No. 11/554,475, Response filed Apr. 21, 2009 to Final Office Action mailed Feb. 4, 2009", 10 pgs.
"U.S. Appl. No. 11/554,475, Response filed Apr. 18, 2008 to Restriction Requirement mailed Feb. 26, 2008", 10 pgs.
"U.S. Appl. No. 11/554,475, Restriction Requirement mailed Feb. 26, 2008", 8 pgs.
"U.S. Appl. No. 11/554,475, Summary of Interview Under 37 C.F.R. § 1.133(b) filed Jul. 9, 2008", 1 pg.

(Continued)

*Primary Examiner*—D. Margaret Seaman
*Assistant Examiner*—Nizal S Chandrakumar
(74) *Attorney, Agent, or Firm*—Schwegman, Lundberg & Woessner, P.A.

(57) ABSTRACT

The present invention relates to metalloprotein inhibitors comprising:

a. an organic substituent and at least one zinc binding group (ZBG) covalently attached thereto; or
b. a ZBG substituted by a side chain wherein the ZBG is of formula (I):

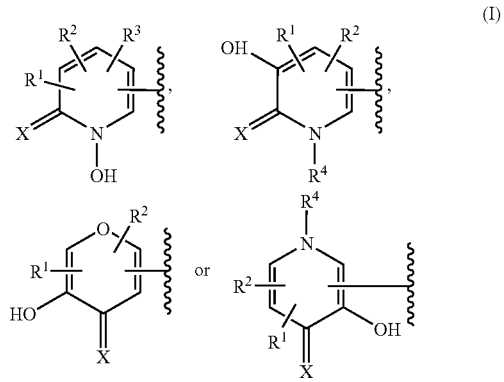

wherein X is O or S and each $R^1$, $R^2$, $R^3$, and $R^4$ is individually hydrogen or an organic radical. The metalloprotein inhibitors are useful for preventing or treating a pathological disease, condition, or symptom that is associated with pathological metalloprotein activity and/or that is alleviated by inhibition of said activity.

4 Claims, 8 Drawing Sheets

OTHER PUBLICATIONS

"U.S. Appl. No. 11/554,475, Amendment and Response filed Sep. 17, 2008 to Non-Final Action mailed Jun. 19, 2008", 11 pgs.

"U.S. Appl. No. 11/568,505, Preliminary Amendment mailed Oct. 30, 2006", 11 pgs.

"U.S. Appl. No. 11/568,505, Supplemental Preliminary Amendment filed Oct. 26, 2007", 9 pgs.

"U.S. Appl. No. 11/568,505, Second Preliminary Amendment filed Aug. 20, 2007", 10 pgs.

"U.S. Appl. No. 11/568,505, Non-Final Office Action mailed Nov. 3, 2008", 12 pgs.

"U.S. Appl. No. 11/568,505, Non-Final Office Action mailed Feb. 25, 2009", 16 pgs.

"U.S. Appl. No. 11/568,505, Response filed Jul. 23, 2009 to Non Final Office Action mailed Feb. 25, 2009", 26 pgs.

"U.S. Appl. No. 11/568,505, Response filed Oct. 17, 2008 to Restriction Requirement mailed Jun. 19, 2008", 15 pgs.

"U.S. Appl. No. 11/568,505, Response filed Feb. 2, 2009 to Non-Final Office Action mailed Nov. 3, 2008", 21 pgs.

"U.S. Appl. No. 11/568,505, Restriction Requirement mailed Jun. 19, 2008", 7 pgs.

"European Applicatiion Serial No. 05818191.8, Communication Pursuant to Article 96(2) EPC mailed Jul. 5, 2007", 4 pgs.

"European Applicatiion Serial No. 05818191.8, Response filed Nov. 7, 2007 to Communication mailed Jul. 5, 2007", 20 pgs.

"European Application Serial No. 05818191.8, Communication mailed Aug. 7, 2009", 4 pgs.

"International Application Serial No. PCT/US2005/014747, International Search Report mailed Mar. 10, 2006", 6 pgs.

"International Application Serial No. PCT/US2005/014747, Written Opinion mailed Mar. 10, 2006", 6 pgs.

Atkinson, J. G., et al., "Kojic Amine—A Novel γ-Aminobutyric Acid Analogue", *Journal of Medicinal Chemistry*, 22 (1), (1979), 99-106.

Aytemir, M. D., et al., "Synthesis and Evaluation of Antimicrobial Activity of New 3-hydroxy-6-methyl-4-xox-4*H*-pyran-2-carbox amide derivatives", *Turkish Journal of Chemistry*, 27(6), (2003), 757-764.

Aytemir, M. D., et al., "Synthesis of New Antimicrobial Agents; Amide Derivatives of Pyranones and Pyridinones", *Turk. J. Chem.*, 27, (2003), 445-452.

Beckett, R. P., et al., "Matrix Metalloproteinase Inhibitors 1998", *Expert Opinion on Therapeutic Patents*, 8(3), (Mar. 1998), 259-282.

Beckett, R. P., et al., "Recent Advances in Matrix Metalloproteinase Inhibitor Research", *Drug Discovery Today*, 1(1), (Jan. 1996), 16-26.

Belonosov, I. S., et al., "4—Pyronecarboxylic acids and their transformations", *Zhumai Prikladnoi Khimii( Sankt-Petersburg, Russian Federation)*, vol. 24, (Abstract Only), (1951), 1 pg.

Brinckerhoff, C. E., et al., "Matrix Metalloproteinases: A Tail of a Frog That Become a Prince", *Nature Reviews—Molecular Cell Biology*, 3, (Mar. 2002), 207-214.

Chen, L., et al., "Crystal Structure of the Stromelysin Catalytic Doman at 2.0 Å Resolution: Inhibitor-Induced Conformational Changes", *Journal of Molecular Biology*, 293, (1999), 545-557.

Cohen, S. M., et al., "Mixed Hydroxypyridinonate Ligands as Iron Chelators", *American Chemical Society*, 39, (Aug. 30, 2000), 4339-4346.

Cohen, S. M., et al., "Syntheses and Relaxation Properties of Mixed Gadolinium Hydroxypyridinonate MRI Contrast Agents", *American Chemical Society*, 39, (2000), 5747-5756.

Cohen, S. M., et al., "Synthesis and Metal Binding Properties of Salicylate-, Catecholate-, and Hydroxypyridinonate-Functionalized Dendrimers", *Chem. Eur. J.*, 7(1), (2001), 272-279.

Georg Iou, N. A., et al., "Human Immunodeficiency Virus Type 1 Replication Inhibition by the Bidentate Iron Chelators CP502 and CP511 IS Caused by Proliferation Inhibition and the Onset of Apoptosis", *European Journal of Clinical Investigation*, 32 ((Issue S1), (2002), 91-96.

Gorden, A. E. V., et al., "Rational Design of Sequestering Agents for Plutonium and Other Actinides", *Chemical Reviews*, 103(11), (2003), 4207-4282.

Hajduk, P. J., et al., "NMR-Based Modification of Matrix Metalloproteinase Inhibitors With Improved Bioavailability", *Journal of Medicinal Chemistry*, 45, (2002), 5628-5639.

Hoeksama, H., et al., "The chemistry of rubradirin. III. The rubradiric acids and the structure of rubradirin", *Journal of Antibiotics*, 32.(7), (Abstract Only), (1979), 1 pg.

Jacobsen, F. E., et al., "Using Model Complexes to Augment and Advance Metalloproteinase Inhibitor Design", *Inorganic Chemistry*, 43 (2004), 3038-3047.

Lewis, J. A., et al., "Metal Complexes of the *trans*-Influencing Ligand Thiomaltol", *Inorganic Chemistry*, 42(23), (2003), 7455-7459.

Lim, S., "Competitive Inhibition of Tyrosinase by 5-Hydroxy-2-phenylalanylaminomethyl-4-pyron", *Yakhak Hoechi*, 44 (3), (w/ English Abstract), (2000), 279-282.

Liu, Z. D., et al., "Design of iron chelators with therapeutic application", *Coordination Chemistry Reviews*, 232, (2002), 151-171.

Liu, Z. D., et al., "Design, Synthesis, and Evaluation of Novel 2-Substituted 3-Hydroxypyridin-4-ones: Structure-Activity Investigation of Metalloenzyme Inhibition by Iron Chelators", *Journal of Medicial Chemistry*, 45(3), (2002), 631-639.

Liu, Z. D., et al., "Synthesis of 2-Amido-3-hydroxypryidin-4(1*H*)-ones: Novel Iron Chelators with Enhanced $pFe^{3+}$ Values", *Bioorganic and Medicinal Chemistry*, 9, (2001), 563-573.

Opdenakker, G., et al., "Cytokines and Proteases in Invasive Processes: Molecular Similarities Between Inflammation and Cancer", *Cytokine*, 4(4), (Jul. 1992), 251-258.

Overall, C. M., et al., "Strategies for NMP Inhibition in Cancer: Innovations for the Post-Trial Era", *Nature Reviews, Cancer*, 2, (Sep. 2002), 657-672.

Pace, P., et al., "The monoethyl ester of meconic acid is an active site inhibitor of HCV NS5B RNA-dependent RNA polymerase", *Bioorganic & Medicinal Chemistry Letters*, 14, (2004), 3257-3261.

Piyamongkol, S., et al., "Novel synthetic approach to 2-(1'-hydroxyalkyl)- and 2-amido-3-hydroxypyridin-4-ones", *Tetrahedron*, 57, (2001), 3479-3486.

Puerta, D. T., et al., "A Bioinorganic Perspective on Matrix Metalloproteinase Inhibition", *Current Topics in Medicinal Chemistry*, 4, (2004), 1551-1573.

Puerta, D. T., et al., "Elucidating Drug-Metalloprotein Interactions with Tris(pyrazolyl)borate Model Complexes", *Inorganic Chemistry*, 41(20), (2002), 5075-5082.

Puerta, D. T., et al., "Examination of Novel Zinc-Binding Groups for Use in Matrix Metalloproteinase Inhibitors", *Inorganic Chemistry*, 42, (2003), 3423-3430.

Puerta, D. T., et al., "From Model Complexes to Metalloprotein Inhibition: A Synergistic Approach to Structure-Based Drug Discovery", *Angewandte Chemie International Edition*, 42(32), (2003), 3772-3774.

Puerta, D. T., et al., "New Beginnings for Matrix Metalloproteinase Inhibitors: Identification of High-Affinity Zinc-Binding Groups", *Journal of the American Chemical Society*, 126(27), (2004), 8388-8389.

Puerta, D. T, et al., "Potent, Selective Pyrone-Based Inhibitors of Stromelysin-1", *J. Am. Chem. Soc.*, 127(41), (2005), 14148-14149.

Scarrow, R. C., et al., "Ferric Ion Sequestering Agents. 13. Synthesis, Structures, and Thermodynamics of Complexation of Cobalt(III) and Iron(III) Tris Complexes of Several Chelating Hydroxypyridinones", *Inorganic Chemistry*, 24(6), (1984), 954-967.

Shapiro, S. D., et al., "Proteolysis In The Lungs", *Eur Respir J*, 22 Suppl. 44), (2003), 30s-32s.

Skiles, J. W., et al., "The Design, Structure, and Therapeutic Application of Matrix Metalloproteinase Inhibitors", *Current Medicinal Chemistry*, 8(4), (2001), 425-474.

Storr, T., et al., "Vanadyl-Thiazolidinedione Combination Agents for Diabetes Therapy", *Bioconjugate Chem.* 14 (1). (2003), 212-221.

White, D. L., et al., "Specific Sequestering Agents for the Actinides. 16. Syntheses and Initial Biological Testing of Polydentate Oxohydroxypyridinecarboxylate Ligands", *J. Med. Chem.*, 31, (1988), 11-18.

Whittaker, M., et al., "Design and Therapeutic Application of Matrix Metalloproteinase Inhibitors", *Chem. Rev.*, 99, (1999), 2735-2776.

Whittaker, M., et al., "Matrix Metalloproteinases and Their Inhibitors—Current Status and Future Challenges", *Celltransmissions*, 17(1), (2001), 3-14.

Wojtowicz-Praga, S. M., et al., "Matrix Metalloproteinase Inhibitors", *Investigational New Drugs*, 15, (1997), 61-75.

Woods, L. L., "Mannich Bases from Kojic Acid and Aryl Amines", *Journal of the American Chemistry Society*, 68, (1946), 2744-2745.

Xu, J., et al., "Specific Sequestering Agents for the Actinides. 28. Syntheses and Initial Evaluation of Multidentate 4-Carbamoyl-3-hydroxy-1-methyl-2(1*H*)-pyridinone Ligands for in Vivo Plutonium(IV) Chelation", *J. Med. Chem*, 38, (1995), 2606-2614.

Yeh, L.-A., et al., "Inhibition of Metalloproteinase by Futoenone Derivatives", *Biorbanic & Medicinal Chemistry Letters*, 5(15), (Aug. 1995), 1637-1642.

"U.S. Appl. No. 11/568,505 Notice of Allowance Mailed Dec. 7, 2009", 6 pgs.

"U.S. Appl. No. 11/568,505, Final Office Action mailed Oct. 21, 2009", 9 pgs.

"U.S. Appl. No. 11/568,505, Response filed Nov. 6, 2009 to Final Office Action mailed Oct. 21, 2009", 12 pgs.

"U.S. Appl. No. 11/554,475, Examiner Interview Summary mailed Apr. 15, 2009", 2 pgs.

"U.S. Appl. No. 11/568,505, Examiner Interview Summary mailed Nov. 20, 2009", 3 pgs.

"U.S. Appl. No. 12/722,623, Preliminary Amendment mailed Mar. 12, 2010", 12 pgs.

"European Application Serial No. 05818191.8, Response filed Jan. 22, 2010 to Communication mailed Aug. 7, 2009", 8 pgs.

| ZBG | MMP-1[a] | MMP-2[a] | MMP-3[a] | MMP3 Colorimetric2[a] |
|---|---|---|---|---|
| AHA | 41600(±400) | 15300(±3000) | 25000(±4000) | |
| 1 | 5960(±40) | 5600(±100) | 1600(±100) | 1500((±10) |
| 2 | 4200(±300) | 2600(±400) | 5100(±200) | |
| 4 | not determined | not determined | 7200(±1200) | 8300(±900) |
| 5 | 4200(±300) | 2600(±100) | 5700(±100) | 16000(±2000) |
| 6 | not determined | not determined | 5700(±200) | 5000(±1000) |
| 7 | 490(±10) | 100(±40) | 35(±3) | 20(±4) |
| 8 | 680(±20) | 380(±10) | 362(±3) | |
| 9 | 150(±10) | 60(±10) | 140(±20) | |
| 10 | not determined | not determined | 120 (±40) | |
| 11 | 400(±10) | 140(±10) | 210 (±20) | |

[a] values based on at least three repetitions

R = any of the backbone groups listed in claims 14 or 57    Some are listed below.

METALLOPROTEIN INHIBITORS

RELATED APPLICATIONS

This application is a divisional application of U.S. Ser. No. 11/554,475, filed Oct. 30, 2006, now U.S. Pat. No. 7,579,486 which claims priority under 35 U.S.C. §119(e) from U.S. Provisional Application Ser. No. 60/826,488, filed Sep. 21, 2006; this application is also a continuation-in-part of PCT/US2005/014747, filed Apr. 28, 2005 and published in English as WO 2006/028523 on Mar. 16, 2006 which claims priority under 35 U.S.C. §119(e) from U.S. Provisional Application Ser. Nos. 60/566,882, filed Apr. 29, 2004, and 60/576,444, filed Jun. 3, 2004; PCT/US2005/014747 is also a continuation-in-part of PCT/US2005/009277, filed Mar. 21, 2005 and published in English as WO 2005/110399 on Nov. 24, 2005, the contents of the applications and publications are incorporated herein by reference in their entireties.

GOVERNMENT GRANT SUPPORT

The present invention was made with the support of the U.S. Government under NIH Grant GM-72129-01. The Government has certain rights in this invention.

BACKGROUND OF THE INVENTION

Metalloprotein inhibition is important for many potential medicinal and cosmetic applications. MMPs are a class of zinc(II)-containing hydrolytic enzymes involved in the breakdown of the extracellular matrix and the basement-membrane including components such as aggrecan, collagen, elastin, fibronectin, gelatin, and laminin. The ability of MMPs to degrade components of the extracellular matrix is essential to tasks such as cell growth, cell division, bone growth, wound healing, embryogenesis, and angiogenesis.[1,2] Disruption of the regulation of MMP activity is correlated to disease states including but not limited to cardiovascular disease, stroke, arthritis, and tumor metastasis.[1-3] Many factors must be considered in designing an effective and selective drug. In the case of matrix metalloproteinase inhibitors (MMPi), the drug typically consists of two parts, a peptidomimetic backbone and a zinc-binding group (ZBG). The backbone serves as a substrate analogue, allowing the inhibitor to fit in the active-site cleft of the enzyme. The ZBG binds to the catalytic zinc(II) ion, thereby rendering the MMP inactive. The vast majority of MMPi investigations have focused on improving the backbone interactions of MMPi while opting to use a well-known ZBG, namely a hydroxamic acid moiety, that has been in regular use for more than 20 years.[1] Although extensive efforts have been made to improve MMPi by manipulating the substrate-like backbone of the drug, significantly fewer efforts have concentrated on improving the ZBG. Thus, there is a need for the identification of more potent and selective ZBGs to take MMPi toward a more productive second generation of development.

Histone deacetylases (HDACs) and the silent information regulator-like family of NAD-dependent deacetylases are important in transcriptional regulation. Acetylation neutralizes the lysine charge, and DNA unwinds, thus allowing active gene expression to occur.[4] Deacetylation leads to the packing of nucleosomes as chromatins and thus gene repression. HDACs deacetylate using an activated water in the active site where two glutamic acid residues and a histidine residue are coordinated to an active site metal ion with a histidine-aspartate charge-relay system.[5] Anomalous HDAC activity has been associated with cancer, and HDAC inhibitors have been proposed as cancer treatments.[6] With HDAC inhibitors (HDACi), the drug generally has a form of a ZBG to bind the catalytic zinc ion, a linker to interact with the narrow channel leading down to the active site, and a surface recognition or capping group that will interact with the surface of the protein.[7] Some of the HDACi in the literature include short chain fatty acids like valproic acid, hydroxamates like trichostatin A, cyclic hydroxamic-acid-containing peptide compounds, epoxides, and benzamidines.[7,8]

Anthrax spores are taken up by alveolar macrophages and germinate in the lymphnodes where the spores create toxins to inhibit immune responses.[9] Anthrax is often asymptomatic until it reaches the blood, and then it is often fatal and non-responsive to traditional antibiotics. In order for an anthrax infection to be toxic, the protective antigen (PA) must form a heptamer that will mediate entry of up to three molecules of edema factor (EF) and lethal factor (LF) per heptamer into cells.[10] Anthrax lethal factor is one of three proteins involved in anthrax pathogenesis and lethality. Inactivation of the LF gene in B. anthracis leads to a thousand-fold or greater reduction of virulence, which suggests that anthrax pathology is largely determined by LF.[11] LF cleaves the N-terminus of the D-domain of mitogen-activated protein kinase kinases (MAPKK), which impairs essential signal transduction pathways such as inhibiting the activation of p38 MAPK switching the signaling macrophage apoptosis before macrophages can be activated and spread the alarm of infection.[9] The active site of anthrax lethal factor consists of two histidine residues and a glutamic acid residue bound to a zinc(II) ion. Again, many known LF inhibitors contain a hydroxamate as a ZBG, and some proposed inhibitors are based on animoglycosides, small peptides attached to a ZBG, or were identified from the NCI Diversity Set.[12-14]

SUMMARY OF THE INVENTION

The present invention provides metalloprotein inhibitors (MPI), such as matrix metalloproteinase inhibitors (MMPi), histone deacetylase inhibitors (HDACi), or anthrax lethal factor inhibitors (LFi).

The present invention provides a metalloprotein inhibitor, of formula (I):

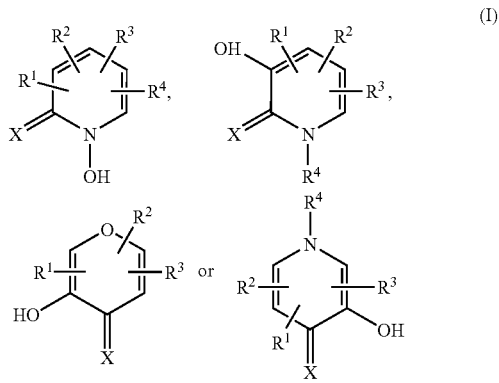

wherein X is O or S and each $R^1$, $R^2$, $R^3$, and $R^4$ is individually hydrogen or another substituent, wherein at least one of $R^1$, $R^2$, $R^3$ and $R^4$ is an organic substituent, or a pharmaceutically acceptable salt thereof. Preferably, at least one or two of $R^1$, $R^2$, $R^3$ and $R^4$ is an organic substituent.

In another embodiment, the present invention provides a metalloprotein inhibitor comprising: an organic substituent and two or more zinc binding groups (ZBG) covalently attached thereto, wherein the ZBG is of formula (II):

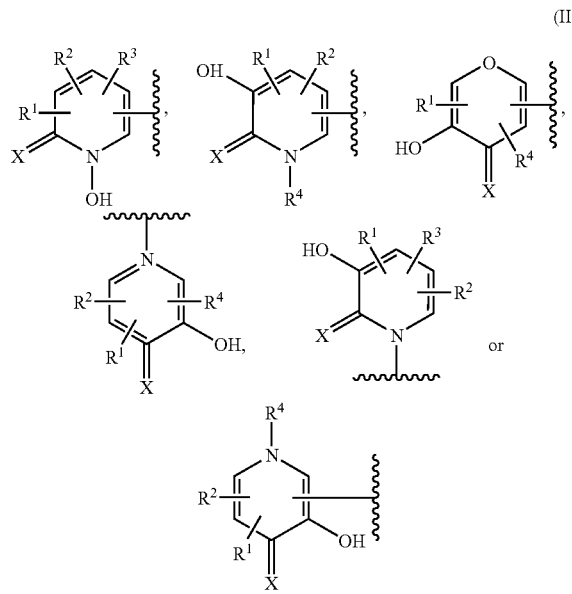

(II)

wherein X is O or S and each $R^1$, $R^2$, $R^3$, and $R^4$ is individually hydrogen or another substituent, or a pharmaceutically acceptable salt thereof. Preferably, at least one of $R^1$, $R^2$, $R^3$ and $R^4$ is an organic substituent.

In a further embodiment of the invention, at least one of $R^1$, $R^2$, $R^3$ or $R^4$ comprises one or more amido and/or amino moieties, including one or more peptidyl residues. For example, at least one of $R^1$, $R^2$, $R^3$ or $R^4$ can be a naturally-occurring peptide, a synthetic peptide, or a peptide analog (peptidomimetic), e.g., an organic group that comprises one or more amido moieties (—C(O)NH—).

Specific embodiments of the invention include compounds, wherein one or two of $R^1$, $R^2$, $R^3$ or $R^4$ is [[($C_6$-$C_{10}$)aryl]$_x$-[($C_6$-$C_{10}$)aryl]$_q$-[O]$_p$—[($C_6$-$C_{10}$)aryl]-[O]$_r$-[($C_1$-$C_6$)alkyl]$_o$-[C(O)]$_s$-[N(R)]-[C(O)]$_t$-[($C_1$-$C_6$)alkyl]$_w$-]  (III)
wherein q, p, r, o, s, t, w and x are individually 0 or 1 and R is H, ($C_1$-$C_4$)alkyl, phenyl, or benzyl.

In specific embodiments of the invention;
preferably ($C_6$-$C_{10}$)aryl is phenyl, preferably 1,4-phenylene;
preferably p and r are 0 and w is 1;
preferably t is 1;
preferably t is 1 and w or o is 1, most preferably —CH$_2$—, —(CH$_2$)$_2$— or —(CH$_2$)$_3$—;
preferably p is 0, r is 0, o is ($C_1$-$C_3$)alkyl or 0, s is 0, t is 1 and w is 0;
preferably q, p, r, and t or s are 0;
preferably q is 1, p is 1, o is 0, s is 0, t is 1 and w is 0;
preferably q is 0 or 1, p is 0 or 1, r is 0, o is 1, s is 0, t is 0 and w is 1; and
Preferably q is 0 or 1, p is 0 or 1, r is 0, o is 0 or 1, s is 0 or 1, t is 0 or 1 and w is 1, with the proviso that s and t are not both 1. When o is 0, w can be 0 or 1.

Preferably x is 1, q is 1, p is 0, r is 0, o and/or w are ($C_1$-$C_3$)alkyl, s is 0 and t is 1.

Preferably x is 1, q is 1, p is 0, r is 0, o is 1, r is 0, s is 0, t is 1 and w is 0 or 1, preferably 0.

Preferably R is H or CH$_3$—.

Preferably one of $R^1$, $R^2$, $R^3$ or $R^4$ is substituent (III); for example, one or two of $R^1$, $R^2$, $R^3$ or $R^4$ are individually biphenylcarbamyl, biphenylcarbamyl($C_1$-$C_6$)alkyl, biphenyl ($C_1$-$C_6$)alkylcarbamyl, biphenyl($C_1$-$C_6$)alkylcarbamyl ($C_1$-$C_6$)alkyl, 4-phenylbiphenylcarbamyl, 4-phenylbiphenyl($C_1$-$C_6$)alkylcarbamyl, 4-cyanophenyl)benzylcarbamyl, 4-methyoxybenzylcarbamyl, phenoxyphenylcarbamyl, ($C_6$-$C_{10}$)aryl($C_1$-$C_6$)alkylamino($C_1$-$C_6$)alkyl, biphenyl($C_1$-$C_6$)alkylamino($C_1$-$C_6$)alkyl, ($C_6$-$C_{10}$)arylcarbonylamino($C_1$-$C_6$)alkyl, ($C_6$-$C_{10}$)aryl($C_1$-$C_6$)alkylcarbonylamino($C_1$-$C_6$)alkyl, biphenyloxy($C_1$-$C_6$)alkylcarbonylamino($C_1$-$C_6$)alkyl, or phenoxyphenylcarbamyl($C_1$-$C_6$)alkyl, wherein, the phenyl or aryl group(s) may be optionally substituted, or a pharmaceutically acceptable salt thereof.

The invention also provides a pharmaceutical composition, such as a unit dosage form, comprising a metalloprotein inhibitor (MPI) compound of the invention, or a pharmaceutically acceptable salt thereof, in combination with a pharmaceutically acceptable diluent or carrier, that can optionally include stabilizers, preservatives, buffers, and absorption control agents.

Additionally, the invention provides a therapeutic method for preventing or treating a pathology, condition or symptom in a mammal, such as a human, that is associated with pathological metalloprotein activity, such as a matrix metalloproteinase (MMP), histone deacetylase (HDAC) or anthrax lethal factor (LF) activity that is alleviated by inhibition of said activity, comprising administering to a mammal in need of such therapy, an effective amount of a metalloprotein inhibitor (MPI) of the invention, including a pharmaceutically acceptable salt thereof.

Also within the scope of the invention is a method of preparing a metalloprotein inhibitor (MPI), by covalently attaching a ZBG of formula (II) to one or more backbone molecules.

Additionally, many of the MPIs of the invention can be used as intermediates to prepare other MPIs of the invention.

SUMMARY OF THE FIGURES

FIG. 4. Summary table of IC$_{50}$ values (uM) for novel ZBGs against MMP-1, -2, and -3 measured using either a fluorescence- or colorimetric-based assay.

DETAILED DESCRIPTION OF THE INVENTION

Figure 1:
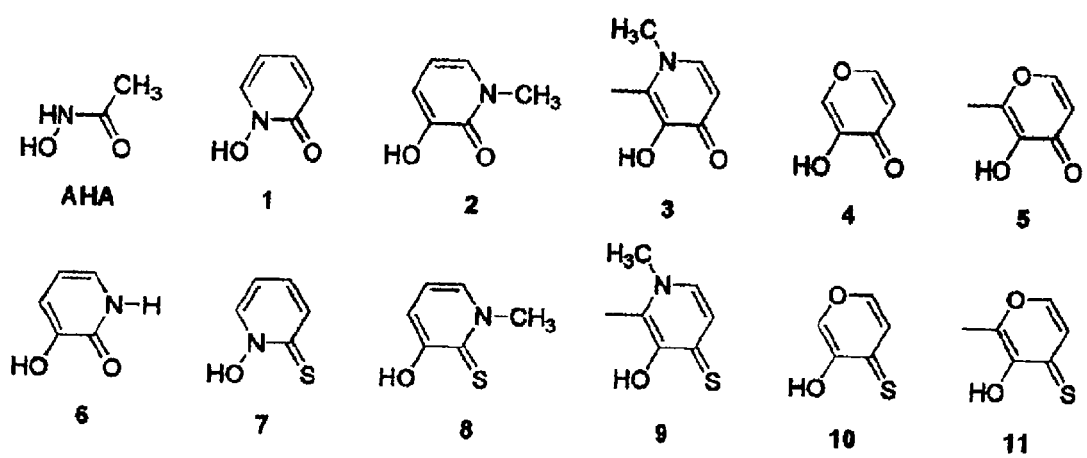
FIG. 1. Representative zinc-binding groups (ZBGs) (1-11). Acetohydroxamic acid (AHA) shown as reference.

Connective tissue, extracellular matrix constituents and basement membranes are required components of all mammals. These components are the biological materials that provide rigidity, differentiation, attachments and, in some cases, elasticity to biological systems including human beings and other mammals. Connective tissues components include, for example, collagen, elastin, proteoglycans, fibronectin and laminin. These biochemicals makeup, or are components of structures, such as skin, bone, teeth, tendon, cartilage, basement membrane, blood vessels, cornea and vitreous humor.

Under normal conditions, connective tissue turnover and/or repair processes are controlled and in equilibrium. The loss of this balance for whatever reason leads to a number of disease states. Inhibition of the enzymes responsible for loss of equilibrium provides a control mechanism for this tissue decomposition and, therefore, a treatment for these diseases.

Degradation of connective tissue or connective tissue components is carried out by the action of proteinase enzymes released from resident tissue cells and/or invading inflammatory or tumor cells. A major class of enzymes involved in this function is the MMPs.

The MMPs are divided into classes with some members having several different names in common use. Examples are: collagenase I (MMP-1, fibroblast collagenase; EC 3.4.24.3); collagenase II (MMP-8, neutrophil collagenase; EC 3.4.24.34), collagenase III (MMP-13), stromelysin 1 (MMP-3; EC 3.4.24.17), stromelysin 2 (MMP-10; EC 3.4.24.22), proteoglycanase, matrilysin (MMP-7), gelatinase A (MMP-2, 72 kDa gelatinase, basement membrane collagenase; EC 3.4.24.24), gelatinase B (MMP-9, 92 kDa gelatinase; EC 3.4.24.35), stromelysin 3 (MMP-11), metalloelastase (MMP-12, HME, human macrophage elastase) and membrane MMP (MMP-14). MMP is an abbreviation or acronym representing the term matrix metalloproteinase with the attached numerals providing differentiation between specific members of the MMP group.

Transcriptional regulation is key to normal functioning in biological systems including human beings and other mammals. Histones form the protein core of nucleosomes, which are DNA/protein complexes that are the subunits of eukaryotic chromatin. The histones are subject to a variety of post-translational modifications such as phosphorylation, ubiquitination and acetylation. These modifications have profound regulatory functions in gene transcription.

The packing and unpacking of nucleosomes as chromatins regulates gene expression. Acetylation of histones leads to an open chromatin structure and gene activation while the deacetylation of histones leads to a condensed chromatin structure and gene repression. The loss of this balance for whatever reason leads to a number of disease states. Inhibition of the enzymes responsible for the loss of equilibrium provides a control mechanism for transcription and gene expression or repression and, therefore, a treatment for these diseases. A major class of enzymes involved in regulation of transcription is (HDACs). HDAC is an abbreviation or acronym representing the term histone deacetylase with the attached numerals providing differentiation between specific members of the HDAC group.

The HDACs are divided into different classes with some members being $NAD^+$-dependent, sometimes referred to as sirtuins. Examples are: HDAC1, HDAC4, HDAC6, HDAC11.

Anthrax lethal toxin, which is a combination of anthrax lethal factor and anthrax protective antigen, impairs multiple systems in the host including human beings and other mammals. Inactivation of the mitogen activated protein kinase (MAPK) signaling pathway in macrophages and dendritic cells impairs innate and adaptive immunity. This disruption of the MAPK pathway has many consequences for the host including but not limited to suppression of cytokine secretion, downregulation of costimulatory molecules, defective T and B cell priming, impaired p38 phosphorylation, endothelial cell apoptosis, macrophage apoptosis and suppression of inflammation.[15] Inhibition of enzymes responsible for these devastating effects provides a control mechanism and, therefore, a treatment for this disease. Anthrax lethal factor is involved in the effects of anthrax infection and the effects of anthrax lethal toxin.

Preferably the organic substituent(s) do(es) not substantially interfere with the ability of the moiety

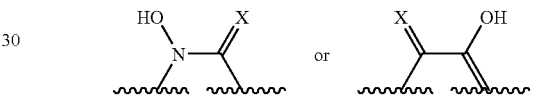

to bind to the metal ion of the target metalloprotein, such as the Zn(II) of a matrix metalloproteinase (MMP). Preferably, the organic radical(s) enhance(s) the ability of said moieties to bind to said Zn(II), or other metal ions.

Generally, the others of $R^1$, $R^2$, $R^3$ and $R^4$ are less bulky than the primary organic substituent(s), although 1-2 of $R^1$, $R^2$, or $R^3$ can be a second or third organic substituent in some instances. Thus, $R^1$, $R^2$, $R^3$, and $R^4$ are individually H, halo, CN, nitro, carboxyl, amino, sulfonamido, $(C_1-C_6)$alkyl, $(C_1-C_6)$alkoxy, $(C_3-C_6)$cycloalkyl, $(C_3-C_6)$cycloalkyl$((C_1-C_6)$alkyl), $(C_6-C_{10})$aryl, $(C_6-C_{10})$aryl$(C_2-C_{10})$alkyl, $(C_6-C_{10})$aryl$(C_2-C_{10})$alkenyl, $(C_6-C_{10})$heteroaryl, $(C_3-C_6)$heterocycloalkyl, $(C_3-C_6)$heterocycloalkyl$(C_1-C_6)$alkyl, $(C_2-C_6)$alkenyl, $(C_2-C_6)$alkynyl, $(C_1-C_6)$alkanoyl, halo$(C_1-C_6)$alkyl, hydroxy$(C_1-C_6)$alkyl, $(C_1-C_6)$alkoxycarbonyl, $(C_1-C_6)$alkylthio, thio$(C_1-C_6)$alkyl, $(C_1-C_6)$alkanoyloxy, biphenylcarbamyl, biphenylcarbamyl-$(C_1-C_6)$alkyl, biphenyl$(C_1-C_6)$alkylcarbamyl, biphenyl$(C_1-C_6)$alkylcarbamyl $(C_1-C_6)$alkyl, phenoxyphenylcarbamyl, $(C_6-C_{10})$aryl$(C_1-C_6)$alkylamino$(C_1-C_6)$alkyl, biphenyl$(C_1-C_6)$alkylamino$(C_1-C_6)$alkyl, $(C_6-C_{10})$arylcarbonylamino$(C_1-C_6)$alkyl, $(C_6-C_{10})$aryl$(C_1-C_6)$alkylcarbonylamino$(C_1-C_6)$alkyl, biphenyloxy$(C_1-C_6)$alkylcarbonylamino$(C_1-C_6)$alkyl, phenoxyphenylcarbamyl $(C_1-C_6)$alkyl, $N(R^6)(R^7)$ or $SO_2N(R^6)(R^7)$, wherein $R^6$ and $R^7$ are individually H, =O, —OH, $(C_1-C_6)$alkyl, $(C_3-C_6)$cycloalkyl, $(C_3-C_6)$cycloalkyl$(C_1-C_6)$alkyl, phenyl or benzyl, or $R^6$ and $R^7$, together with the N to which they are attached, form a 5- or 6-membered ring which may optionally contain 1-2 S, $N(R^6)$ or nonperoxide O; or $R^1$ and $R^2$ together are methylenedioxy; optionally any of $R^1$, $R^2$, $R^3$, and $R^4$ is substituted with one to four $R^1$.

In one embodiment, one of $R^3$ or $R^4$ is $[[(C_6-C_{10})aryl]_q-[O]_q—[(C_6-C_{10})aryl]-[O]_q—[(C_1-C_6)alkyl]_q-[C(O)]_q—[N$ (R)]—[C(O)]$_q$—[(C$_1$-C$_6$)alkyl]$_q$-] wherein each q is 0 or 1 and R is H, (C$_1$-C$_4$)alkyl, phenyl, or benzyl.

In another embodiment, one of R$^3$ or R$^4$ is [[(C$_6$-C$_{10}$)aryl]$_q$-[(C$_6$-C$_{10}$)aryl]$_q$-[O]$_q$—[(C$_6$-C$_{10}$)aryl]-[O]$_q$—[(C$_1$-C$_6$)alkyl]$_q$-[C(O)]$_q$—[N(R)]—[C(O)]$_q$—[(C$_1$-C$_6$)alkyl]$_q$-] wherein q is 0 or 1 and R is H, (C$_1$-C$_4$)alkyl, phenyl, or benzyl, and the ZBG is as shown in Table 1.

TABLE 1

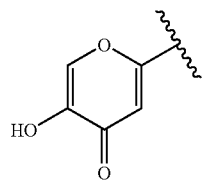

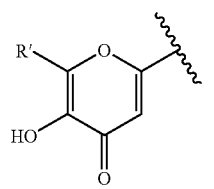

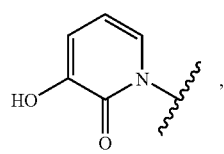

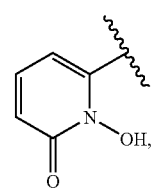

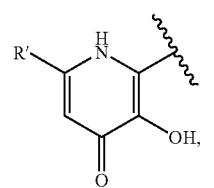

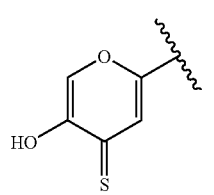

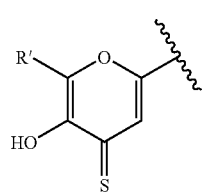

TABLE 1-continued

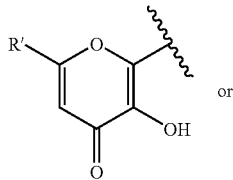

or

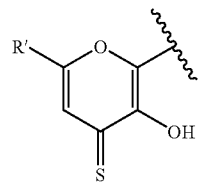

wherein R' is H or CH$^3$. The compounds of the invention also include those in which the free OH or NH of the ZBG is protected with a removable hydroxyl- or amino-protecting group, including (R) as defined above for N(R) and O(R) wherein R" is benzyl, THP, EtOEt-, (C$_1$-C$_4$)alkyl, (C$_1$-C$_4$)$_3$Si— and the like.

In a further embodiment, R$^3$ and R$^4$ are side chains that are individually biphenylcarbamyl, biphenylcarbamyl-(C$_1$-C$_6$)alkyl, biphenyl(C$_1$-C$_6$)alkylcarbamyl, biphenyl(C$_1$-C$_6$)alkylcarbamyl (C$_1$-C$_6$)alkyl, phenoxyphenylcarbamyl, (C$_6$-C$_{10}$)aryl(C$_1$-C$_6$)alkylamino(C$_1$-C$_6$)alkyl, biphenyl(C$_1$-C$_6$)alkylamino(C$_1$-C$_6$)alkyl, (C$_6$-C$_{10}$)arylcarbonylamino(C$_1$-C$_6$)alkyl, (C$_6$-C$_{10}$)aryl(C$_1$-C$_6$)alkylcarbonylamino (C$_1$-C$_6$)alkyl, biphenyloxy(C$_1$-C$_6$)alkylcarbonylamino (C$_1$-C$_6$)alkyl, phenoxyphenylcarbamyl(C$_1$-C$_6$)alkyl, wherein the phenyl or aryl group(s) in the side chains may be optionally substituted with one to four R$^1$.

Exemplary side chains include biphenylmethylcarbamyl, phenoxyphenylcarbamyl, biphenylcarbamyl, benzylaminomethyl, phenethylaminomethyl, benzoylaminomethyl, benzylcarbonylaminomethyl, phenethylcarbonylaminomethyl, phenylpropylcarbonylaminomethyl, biphenylmethylcarbamylmethyl, phenoxyphenylcarbamylmethyl, biphenylcarbamylmethyl, and biphenylyloxyethylcarbonylaminomethyl, wherein the phenyl groups are optionally substituted with one to four R$^1$. Biphenyl is (4-phenyl)phenyl. Phenethyl is 2-phenylethyl.

Further embodiments of the invention include MPI compounds comprising ZBGs of formula (II) wherein the dangling valence is substituted by R$^7$, wherein R$^7$ is selected from R$^1$, R$^2$, or R$^3$. R$^7$ can also be a polymer chain, such as a polyanhydride, polylactone, polyether, polyester, polyamide, polyalkenylene, polyol, and the like.

As used herein, the term "treatment" of a metalloprotein-associated pathology, includes inhibiting metalloprotein activity such as HDAC, LF, or MMP activity in a subject exhibiting at least one of the symptoms of the onset of a metalloprotein-associated pathology or who is likely to develop such a pathology as well as the ability to halt or slow the progression of a metalloprotein-associated pathology or to reduce or alleviate at least one of the symptoms of said pathology.

A "therapeutic effect", "effective amount," or "therapeutic effective amount" is intended to qualify the amount of an anticancer agent according to the present invention required to relieve to some extent one or more of the symptoms and/or conditions of cancer, including, but is not limited to: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with cancer; and/or 7) relieving or reducing the side effects associated with the administration of anticancer agents. The terms also are intended to qualify the amounts of anti-inflammatory agents or anti-anthrax lethal factor agents according to the present invention required to relieve to some extent one or more of the symptoms and/or conditions of diseases including, but not limited to inhibition of anthrax toxin generation or its effects in vivo, including edema, septicemia and pneumonia, as well as inflammatory pathologies such as arthritis (e.g., RA), restenosis, aortic aneurism, IBD, glomerular nephritis, MS, stroke, diabetes, bacterial meningitis, and graft vs. host disease. The terms also are intended to qualify the amounts of agents according to the present invention required to relieve to some extent one or more of the symptoms and/or conditions of diseases include epidermal scars, myocardial infarction, and periodontal disease.

The use of the term "about" in the present disclosure means "approximately," and encompasses variations in parameters that would arise during practice of the relevant art. Illustratively, the use of the term "about" indicates that dosages outside the cited ranges may also be effective and safe, and such dosages are also encompassed by the scope of the present claims.

The term "pharmaceutically acceptable" is used adjectivally herein to mean that the modified noun is appropriate for use in a pharmaceutical product.

The phrase "metalloprotein inhibitor" or "MPI" includes agents that specifically inhibit a class of enzymes such as MMP, HDAC, and LF. The MMPs are involved in the degradation of connective tissue or connective tissue components. These enzymes are released from resident tissue cells and/or invading inflammatory or tumor cells. Blocking the action of MMPs interferes with the creation of paths for newly forming blood vessels to follow. Examples of MMPi are described in Whittaker et al. and Skiles et al. and are hereby incorporated by reference.[1,40]

The following definitions are used, unless otherwise described: halo is fluoro, chloro, bromo, or iodo. Alkyl, alkoxy, alkenyl, alkynyl, etc. denote both straight and branched groups; but reference to an individual radical such as Apropyl@ embraces only the straight chain radical, a branched chain isomer such as Aisopropyl@ being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing about 5 or 6 ring atoms consisting of carbon and one to four heteroatoms each selected from the group consisting of non-peroxide oxygen, sulfur, and $N(R^7)$ wherein $R^7$ is absent or is as defined above; as well as a radical of an ortho-fused bicyclic heterocycle of about eight to ten ring atoms derived therefrom, particularly a benz-derivative or one derived by fusing a propylene, trimethylene, or tetramethylene diradical thereto.

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_{12})$cycloalkyl can be monocyclic, bicyclic or tricyclic and includes cyclopropyl, cyclobutyl, cyclopentyl, cyclohexyl, bicyclo[2.2.2]octanyl, norbornyl, adamantyl as well as various terpene and terpenoid structures. $(C_3-C_{12})$cycloalkyl$(C_1-C_6)$alkyl includes the foregoing cycloalkyl and can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl. Heterocycloalkyl and (heterocycloalkyl)alkyl include the foregoing cycloalkyl wherein the cycloalkyl ring system is monocyclic, bicyclic or tricyclic and optionally comprises 1-2 S, non-peroxide O or $N(R^7)$ as well as 2-12 ring carbon atoms; such as morpholinyl, piperidinyl, piperazinyl, indanyl, 1,3-dithian-2-yl, and the like; the cycloalkyl ring system optionally includes 1-3 double bonds or epoxy moieties and optionally is substituted with 1-3 OH, $(C_1-C_6)$alkanoyloxy, (CO), $(C_1-C_6)$alkyl or $(C_2-C_6)$alkynyl. $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be formyl, acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be alkyl substituted with 1 or 2 OH groups, such as hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 3,4-dihydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, indanyl, or naphthyl; and heteroaryl can be furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl, (or its N-oxide), thienyl, pyrimidinyl (or its N-oxide), 1H-indolyl, isoquinolyl (or its N-oxide) or quinolyl (or its N-oxide).

Optionally, any of $R^1$, $R^2$, or $R^3$ can be substituted by one to three $R^1$ (except for H, halo or CN).

Preferably, one of $R^1$, $R^2$, or $R^3$ is $(C_1-C_3)$alkyl.

Preferably, one of $R^1$, $R^2$, or $R^3$ is H.

Preferably, $R^4$ is $(C_1-C_3)$alkyl, benzyl, t-Boc, $(C_3-C_6)$cycloalkyl$(C_1-C_3)$alkyl, or H.

Figure 5:
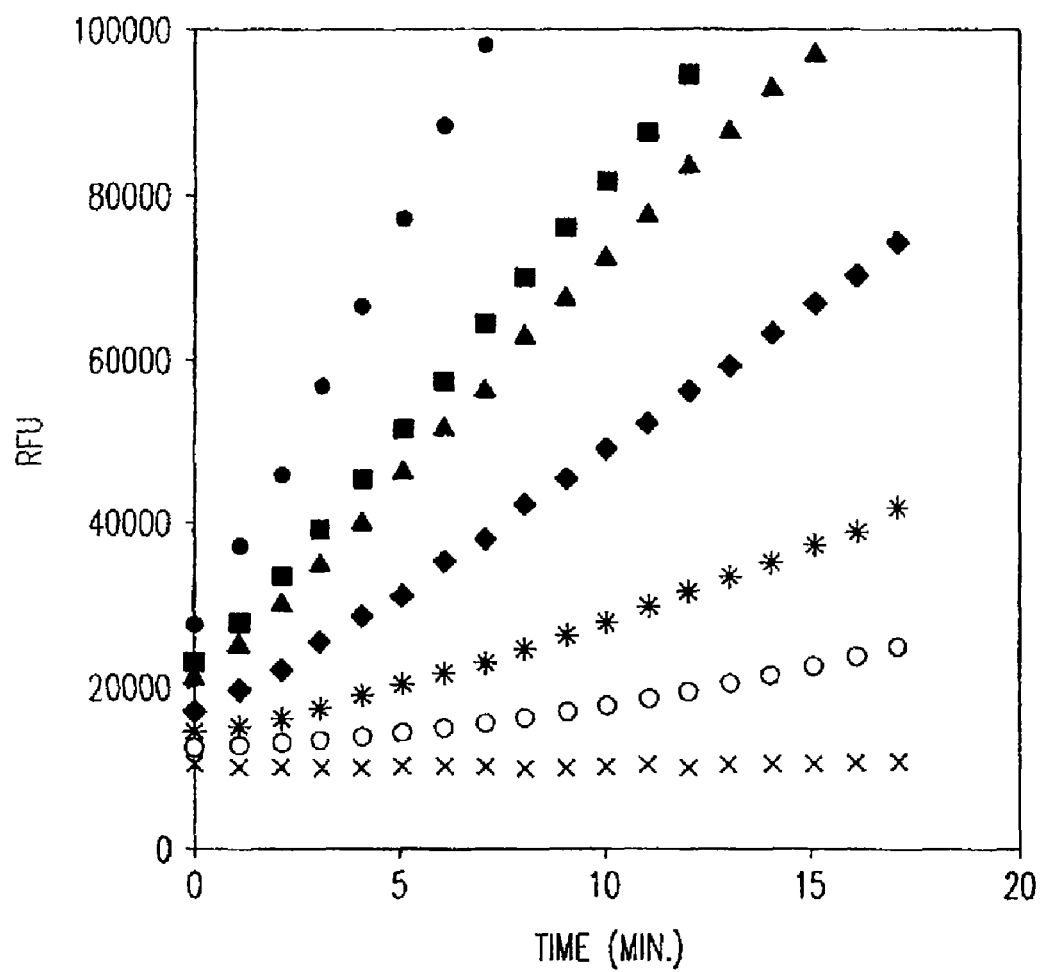
FIG. 5. Raw data from fluorescent assay of 11 with MMP-3. Relative fluorescent units (RFU) produced from substrate cleavage in each reaction well: control (0 mM 11, circles ●), 11 0.05 mM (squares), 11 0.1 mM (triangles ▲), 11 0.2 mM (diamonds ◆), 11 0.3 mM (*), 11 0.5 mM (○), and 11 1.0 mM (x) are plotted versus time in minutes FIG. 6. IC$_{50}$ plot of 11. The slopes of kinetic traces from the plot shown in FIG. 5 containing inhibitor are compared to the slope of the control (no inhibitor). The [(inhibitor slope/control slope)×100] (% Control) is plotted versus inhibitor concentration. A linear fit of the data for each experiment (three experiments shown in FIG. 6) gives the $IC_{50}$ value of the inhibitor where y=50%.
Figure 6:
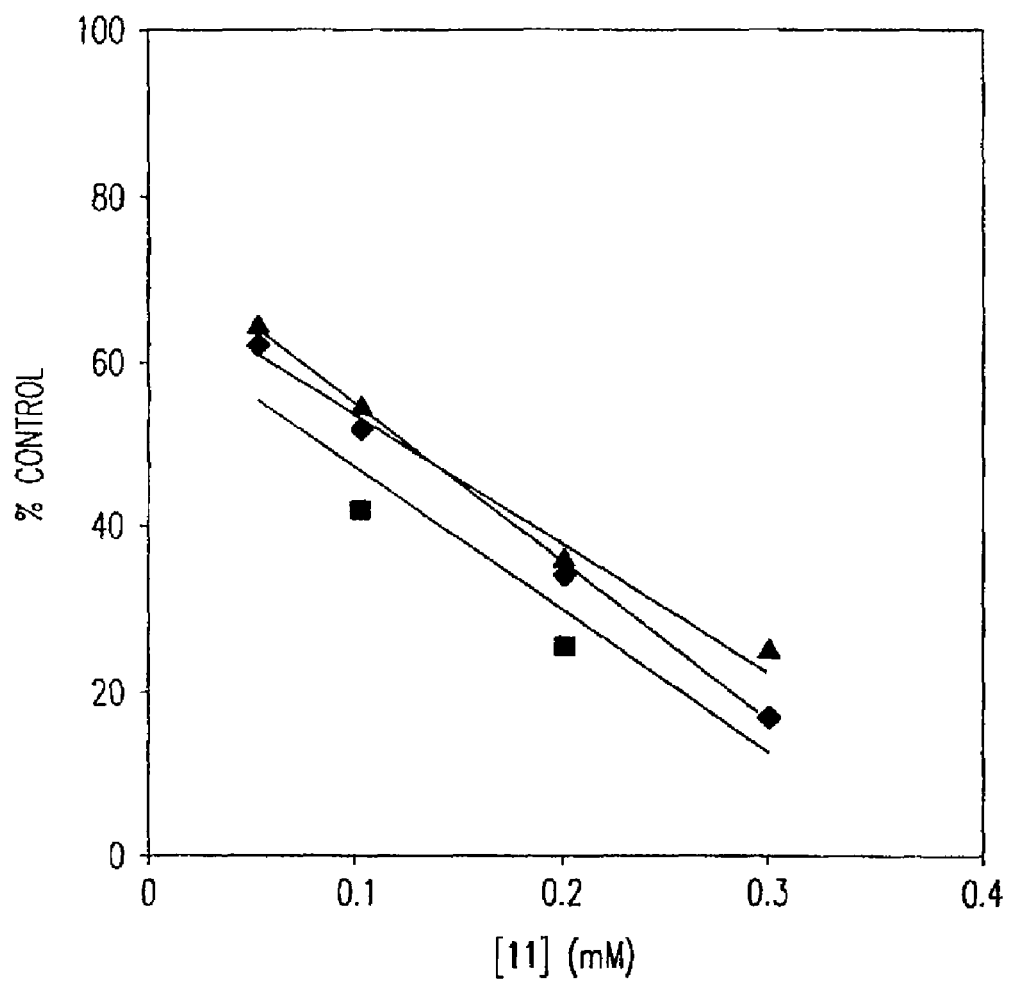

Useful backbone molecules comprise organic substituents having the structural features depicted in FIG. 5 and FIG. 6 of Whittaker et al.,[1] wherein the moiety HON(H)—C(O)—CH($R_a$)— has been replaced with a ZBG of formula (I), or the structural features depicted in the claims of EPA 126,974, wherein at least the moiety $COR^1$ has been replaced by a ZBG of formula (I).

The structure of the organic backbone molecule(s) and other organic substituents preferably do not interfere with and, preferably enhance the ability of the MPI to direct the ZBG toward one or more complexed metal ions, such as Zn(II) atoms of the MMP. For example, Pep can be any of the organic radicals derived from the structures shown on Scheme 1 of the Whittaker et. al.,[1] after removal of the C(O)

NH(OH) group, or in the claims of published European patent application No. 126,974, after removal of COR$^1$.

The organic backbone molecule and/or organic substituent(s) can be a naturally-occurring peptide, a synthetic peptide or a peptide analog (peptidomimetic). Such groups may comprise one or more amido moieties (—C(O)NH—), which can be or comprise, peptidyl bonds, e.g., amide bonds formed by reaction of the amino group of an alpha-aminocarboxylic acid with the carboxy group of a second amino acid.

For example, embodiments of the compound of formula (I) or (II) can be represented by [ZBG]-C(R$^5$)(R$^6$)—C(O)NH—, [ZBG]-C(R$^8$)—C(O)N(H)—CH(R$^9$)—C(O)NH(R$^{10}$), or [ZBG-C(R$^5$)(R$^6$)—C(O)N(H)—CH(R$^9$)—C(O)NH(R$^{10}$), wherein ZBG comprises the heterocyclic ring of formula (I) or (II) R$^8$, R$^9$ and R$^{10}$ correspond to R$^1$, R$^2$ and R$^3$ respectively, and wherein R$^5$ is H and R$^6$ is $(C_1\text{-}C_{22})$alkyl, $(C_2\text{-}C_6)$alkenyl, $(C_6\text{-}C_{10})$aryl, $(C_1\text{-}C_6)$alkyl, $(C_6\text{-}C_{10})$heteroaryl, $(C_6\text{-}C_{10})$heteroaryl$(C_1\text{-}C_6)$alkyl, $(C_3\text{-}C_6)$cycloalkyl, $(C_3\text{-}C_6)$cycloalkyl$(C_1\text{-}C_6)$alkyl, or R$^5$ and R$^6$ together with the carbon atom to which they are attached can be $(C_4\text{-}C_6)$ spiroalkyl or spiroheterocycloalkyl. In certain embodiments of the invention, peptidyl or peptidomimetic substituents are terminated by a ZBG of formula (I) or (II), and optionally, the other terminus is C(O)N(R$^6$)(R$^7$).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-toxin activity using the standard tests described herein, or using other similar tests which are well known in the art.

In cases where compounds are sufficiently basic or acidic to form stable nontoxic acid or base salts, administration of the compounds as salts may be appropriate. Pharmaceutically acceptable salts may be obtained using standard procedures well known in the art, for example by reacting a sufficiently basic compound such as an amine with a suitable acid affording a physiologically acceptable anion.

Pharmaceutically acceptable salts include metallic ions and organic ions. More preferred metallic ions include, but are not limited to appropriate alkali metal (Group Ia) salts, for example, sodium potassium, or lithium, and alkaline earth metal (Group IIa) salts, for example, calcium, and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine.

Illustrative pharmaceutically acceptable salts are prepared from hydrochloric, hydrobromic, phosphoric, sulfuric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxy-ethanesulfonic, sulfanilic, cyclohexylaminosulfonic, algenic, β-hydroxybutyric, galactaric and galacturonic acids.

The compositions of the present invention are usually administered in the form of pharmaceutical compositions. These compositions can be administered by any appropriate route including, but not limited to, oral, nasogastric, rectal, transdermal, parenteral (for example, subcutaneous, intramuscular, intravenous, intramedullary, intrasternal, and intradermal injections, or infusion techniques), intranasal, transmucosal, implantation, vaginal, topical, buccal, and sublingual administration. Such preparations may routinely contain buffering agents, preservatives, penetration enhancers, compatible carriers, and other therapeutic or non-therapeutic ingredients.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, or polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono-, di- or triglycerides, fatty acids and polyethylene glycols that are solid at ordinary temperatures but liquid at the rectal temperature and will therefore melt in the rectum and release the drug.

Solid dosage forms for oral administration can include capsules, ingestible tablets, buccal tablets, troches, dragées, pills, powders, granules, and wafers. In such solid dosage forms, the compounds of this invention are ordinarily combined with one or more adjuvants appropriate to the indicated route of administration. The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, granules, or capsules may be coated with gelatin, wax, shellac or sugar and the like. The tablets, pills, granules, or capsules comprising the inventive compositions may be film coated or enteric-coated.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Useful liquid carriers include water, alcohols or glycols, or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of active ingredient that can be combined with the carrier materials to produce a single dosage form varies depending upon the mammalian host treated and the particular mode of administration.

The present invention also includes methods employing a pharmaceutical composition that contains the composition of the present invention associated with pharmaceutically acceptable carriers or excipients. As used herein, the terms "pharmaceutically acceptable carrier" or "pharmaceutically acceptable excipients" includes any and all solvents, dispersion media, coatings, antibacterial and antifungal agents, isotonic and absorption delaying agents, and the like. The use of such media and agents for ingestible substances is well known in the art. Except insofar as any conventional media or agent is incompatible with the compositions, its use is contemplated. Supplementary active ingredients can also be incorporated into the compositions. In making the compositions of the present invention, the compositions(s) can be mixed with a pharmaceutically acceptable excipient, diluted by the excipient or enclosed within such a carrier, which can be in the form of a capsule, sachet, or other container. The carrier materials that can be employed in making the composition of the present invention are any of those commonly used excipients in pharmaceutics and should be selected on the basis of compatibility with the active drug and the release profile properties of the desired dosage form.

Illustratively, pharmaceutical excipients are chosen below as examples:

(a) Binders such as acacia, alginic acid and salts thereof, cellulose derivatives, methylcellulose, hydroxyethyl cellulose, hydroxypropyl cellulose, magnesium aluminum silicate, polyethylene glycol, gums, polysaccharide acids, bentonites, hydroxypropyl methylcellulose, gelatin, polyvinylpyrrolidone, polyvinylpyrrolidone/vinyl acetate copolymer, crospovidone, povidone, polymethacrylates, hydroxypropylmethylcellulose, hydroxypropylcellulose, starch, pregelatinized starch, ethylcellulose, tragacanth, dextrin, microcrystalline cellulose, sucrose, or glucose, and the like.

(b) Disintegration agents such as starches, pregelatinized corn starch, pregelatinized starch, celluloses, cross-linked carboxymethylcellulose, sodium starch glycolate, crospovidone, cross-linked polyvinylpyrrolidone, croscarmellose sodium, microcrystalline cellulose, a calcium, a sodium alginate complex, clays, alginates, gums, or sodium starch glycolate, and any disintegration agents used in tablet preparations.

(c) Filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

(d) Surfactants such as sodium lauryl sulfate, sorbitan monooleate, polyoxyethylene sorbitan monooleate, polysorbates, polaxomers, bile salts, glyceryl monostearate, Pluronic™ line (BASF), and the like.

(e) Solubilizer such as citric acid, succinic acid, fumaric acid, malic acid, tartaric acid, maleic acid, glutaric acid sodium bicarbonate and sodium carbonate and the like.

(f) Stabilizers such as any antioxidation agents, buffers, or acids, and the like, can also be utilized.

(g) Lubricants such as magnesium stearate, calcium hydroxide, talc, sodium stearyl fumarate, hydrogenated vegetable oil, stearic acid, glyceryl behapate, magnesium, calcium and sodium stearates, stearic acid, talc, waxes, Stearowet, boric acid, sodium benzoate, sodium acetate, sodium chloride, DL-leucine, polyethylene glycols, sodium oleate, or sodium lauryl sulfate, and the like.

(h) Wetting agents such as oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, or sodium lauryl sulfate, and the like.

(i) Diluents such lactose, starch, mannitol, sorbitol, dextrose, microcrystalline cellulose, dibasic calcium phosphate, sucrose-based diluents, confectioner's sugar, monobasic calcium sulfate monohydrate, calcium sulfate dihydrate, calcium lactate trihydrate, dextrates, inositol, hydrolyzed cereal solids, amylose, powdered cellulose, calcium carbonate, glycine, or bentonite, and the like.

(j) Anti-adherents or glidants such as talc, corn starch, DL-leucine, sodium lauryl sulfate, and magnesium, calcium, or sodium stearates, and the like.

(k) Pharmaceutically compatible carrier comprises acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, or pregelatinized starch, and the like.

Additionally, drug formulations are discussed in, for example, Remington's The Science and Practice of Pharmacy (2000). Another discussion of drug formulations can be found in Liberman, H. A. and Lachman, L., Eds., Pharmaceutical Dosage Forms, Marcel Decker, New York, N.Y., 1980.

Besides being useful for human treatment, the present invention is also useful for other subjects including veterinary animals, reptiles, birds, exotic animals, and farm animals, including mammals, rodents, and the like. Mammal includes a primate, for example, a monkey, or a lemur, a horse, a dog, a pig, or a cat. A rodent includes a rat, a mouse, a squirrel, or a guinea pig.

Additionally, the invention provides a therapeutic method for preventing or treating a pathological disease, condition or symptom in a mammal, such as a human, that is associated with pathological metalloprotein activity, such as a matrix metalloproteinase (MMP), histone deacetylase (HDAC) or anthrax lethal factor (LF) activity that is alleviated by inhibition of said activity, comprising administering to a mammal in need of such therapy, an effective amount of a metalloprotein inhibitor (MPI) of the invention, including a pharmaceutically acceptable salt thereof.

Such conditions, disease or symptoms include cancer, anthrax pathogenesis associated with anthrax lethal factor, and the inflammatory pathologies set forth in Whitaker, et al. or EPA 126,974, cited above, including arthritis (e.g., RA), restenosis, aortic aneurism, IBD, glomerular nephritis, MS, stroke, diabetes, bacterial meningitis, and graft vs. host disease. Cancers amenable to treatment include leukemia, myeloma, lymphoma, metastatic breast or metastatic prostate cancer, Hodgkin's lymphoma, non-Hodgkin's lymphoma, osteosarcoma, germ cell tumor, lung cancer, ovarian cancer, pancreatic cancer, renal cell carcinoma, melanoma, myelodysplastic syndrome, Ewing's sarcoma, and Paget's disease. Other conditions or diseases amenable to treatment include epidermal scars, myocardial infarction, and periodontal disease.

For treatment of a pathological disease, condition, or symptom associated with pathological metalloprotein activity, such as a matrix metalloproteinase (MMP) activity, histone deacetylase activity (HDAC), or lethal factor activity (LF), and/or that is alleviated by inhibition of said activity, compositions of the invention can be used to provide a dose of a compound of the present invention in an amount sufficient to elicit a therapeutic response, e.g., inhibition of tumor growth, for example a dose of about 5 ng to about 1000 mg, or about 100 ng to about 600 mg, or about 1 mg to about 500 mg, or about 20 mg to about 400 mg. Typically a dosage effective amount will range from about 0.0001 mg/kg to 1500 mg/kg, more preferably 1 to 1000 mg/kg, more preferably from about 1 to 150 mg/kg of body weight, and most preferably about 50 to 100 mg/kg of body weight. A dose can be administered in one to about four doses per day, or in as many doses per day to elicit a therapeutic effect. Illustratively, a dosage unit of a composition of the present invention can typically contain, for example, about 5 ng, 50 ng 100 ng, 500 ng, 1 mg, 10 mg, 20 mg, 40 mg, 80 mg, 100 mg, 125 mg, 150 mg, 200 mg, 250 mg, 300 mg, 350 mg, 400 mg, 450 mg, 500 mg, 550 mg, 600 mg, 700 mg, 800 mg, 900 mg, or 1000 mg of a compound of the present invention. The dosage form can be selected to accommodate the desired frequency of administration used to achieve the specified dosage. The amount of the unit dosage form of the composition that is administered and the dosage regimen for treating the condition or disorder depends on a variety of factors, including, the age, weight, sex and medical condition, of the subject, the severity of the condition or disorder, the route and frequency of administration, and this can vary widely, as is well known.

In one embodiment of the present invention, the composition is administered to a subject in an effective amount, that is, the composition is administered in an amount that achieves a therapeutically effective dose of a compound of the present invention in the blood serum of a subject for a period of time to elicit a desired therapeutic effect. Illustratively, in a fasting adult human (fasting for generally at least 10 hours) the composition is administered to achieve a therapeutically effective dose of a compound of the present invention in the blood serum of a subject from about 5 minutes after administration of the composition. In another embodiment of the present invention, a therapeutically effective dose of the compound of the present invention is achieved in the blood serum of a subject at about 10 minutes from the time of administration of the composition to the subject. In another embodiment of the present invention, a therapeutically effective dose of the compound of the present invention is achieved in the blood serum of a subject at about 20 minutes from the time of administration of the composition to the subject. In yet another embodiment of the present invention, a therapeutically effective dose of the compound of the present invention is achieved in the blood serum of a subject at about 30 minutes from the time of administration of the composition to the subject. In still another embodiment of the present invention, a therapeutically effective dose of the compound of the present invention is achieved in the blood serum of a subject at about 40 minutes from the time of administration of the composition to the subject. In one embodiment of the present invention, a therapeutically effective dose of the compound of the present invention is achieved in the blood serum of a subject at about 20 minutes to about 12 hours from the time of administration of the composition to the subject. In another embodiment of the present invention, a therapeutically effective dose of the compound of the present invention is achieved in the blood serum of a subject at about 20 minutes to about 6 hours from the time of administration of the composition to the subject. In yet another embodiment of the present invention, a therapeutically effective dose of the compound of the present invention is achieved in the blood serum of a subject at about 20 minutes to about 2 hours from the time of administration of the composition to the subject. In still another embodiment of the present invention, a therapeutically effective dose of the compound of the present invention is achieved in the blood serum of a subject at about 40 minutes to about 2 hours from the time of administration of the composition to the subject. And in yet another embodiment of the present invention, a therapeutically effective dose of the compound of the present invention is achieved in the blood serum of a subject at about 40 minutes to about 1 hour from the time of administration of the composition to the subject.

In one embodiment of the present invention, a composition of the present invention is administered at a dose suitable to provide a blood serum concentration with a half maximum dose of a compound of the present invention. Illustratively, a blood serum concentration of about 0.01 to about 1000 nM, or about 0.1 to about 750 nM, or about 1 to about 500 nM, or about 20 to about 1000 nM, or about 100 to about 500 nM, or about 200 to about 400 nM is achieved in a subject after administration of a composition of the present invention.

Contemplated compositions of the present invention provide a therapeutic effect as compound of the present invention medications over an interval of about 5 minutes to about 24 hours after administration, enabling once-a-day or twice-a-day administration if desired. In one embodiment of the present invention, the composition is administered at a dose suitable to provide an average blood serum concentration with a half maximum dose of a compound of the present invention of at least about 1 µg/ml, or at least about 5 µg/ml, or at least about 10 µg/ml, or at least about 50 µg/ml, or at least about 100 µg/ml, or at least about 500 µg/ml, or at least about 1000 µg/ml in a subject about 10, 20, 30, or 40 minutes after administration of the composition to the subject.

The amount of therapeutic agent necessary to elicit a therapeutic effect can be experimentally determined based on, for example, the absorption rate of the agent into the blood serum, the bioavailability of the agent, and the potency for treating the disorder. It is understood, however, that specific dose levels of the therapeutic agents of the present invention for any particular subject depends upon a variety of factors including the activity of the specific compound employed, the age, body weight, general health, sex, and diet of the subject (including, for example, whether the subject is in a fasting or fed state), the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for subject administration. Studies in animal models generally may be used for guidance regarding effective dosages for treatment of diseases in accordance with the present invention. In terms of treatment protocols, it should be appreciated that the dosage to be administered will depend on several factors, including the particular agent that is administered, the route administered, the condition of the particular subject, etc. Generally speaking, one will desire to administer an amount of the compound that is effective to achieve a serum level commensurate with the concentrations found to be effective in vitro for a period of time effective to elicit a therapeutic effect. Thus, where a compound is found to demonstrate in vitro activity at, for example, a half-maximum effective dose of 200 nM, one will desire to administer an amount of the drug that is effective to provide about a half-maximum effective dose of 200 nM concentration in vivo for a period of time that elicits a desired therapeutic effect, for example, treating a disorder related to high beta-amyloid-induced neurotoxicity and other indicators as are selected as appropriate measures by those skilled in the art. Determination of these parameters is well within the skill of the art. These considerations are well known in the art and are described in standard textbooks.

In order to measure and determine the effective amount of a compound of the present invention to be delivered to a subject, serum concentrations of a compound of the present invention can be measured using standard assay techniques.

Contemplated compositions of the present invention provide a therapeutic effect over an interval of about 30 minutes to about 24 hours after administration to a subject. In one embodiment compositions provide such therapeutic effect in about 30 minutes. In another embodiment compositions provide therapeutic effect over about 24 hours, enabling once-a-day administration to improve patient compliance.

The present methods and compositions can also be used in combination ("combination therapy") with another pharmaceutical agent that is indicated for treating cancer, anthrax pathogenesis associated with anthrax lethal factor, and the inflammatory pathologies and other conditions or diseases set forth above.

Tris(pyrazolyl)borate Model Complexes. Previous work has shown that tris(pyrazolyl)borate complexes of zinc provide an accurate model for the tris(histidine) active site of several metalloproteins including MMPs.[16-20] In addition, studies on these model compounds have shown that acetohydroxamic acid forms a complex that is structurally identical to the coordination environment of hydroxamate-based drugs bound to the catalytic zinc(II) ion in MMPs.[16,21] Using this same model, the interaction of ZBGs from identified inhibitors was evaluated where the mode of binding was unknown.[16] This study proved to be very informative, because a direct correlation between the inhibitory activity and mode of binding was found.[10] These observations further validate the use of model complexes as an effective strategy for determining, at a molecular level, the interactions between inhibitors and MMPs.

Figure 2A:
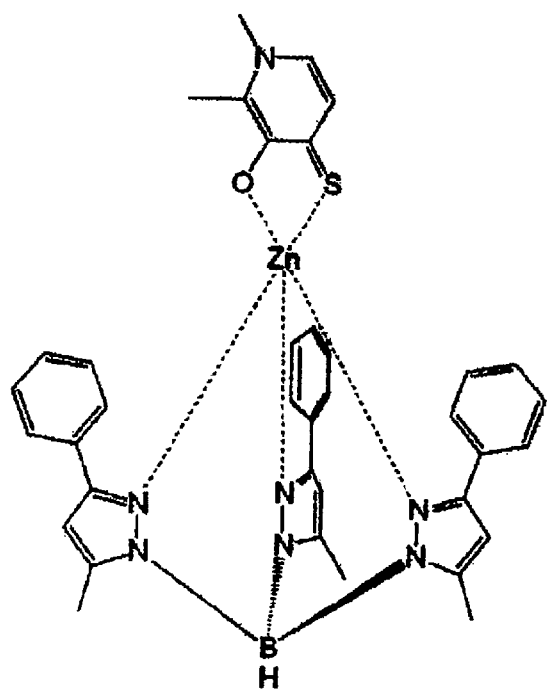
FIGS. 2A. Chemical (top) and 2B structural (bottom, 50% probability ellipsoids) diagram of [(Tp$^{Ph,Me}$)Zn(9)] showing the chelation of the O, S ligand to the zinc(II) ion. Hydrogen atoms have been omitted for clarity.
Figure 2B:
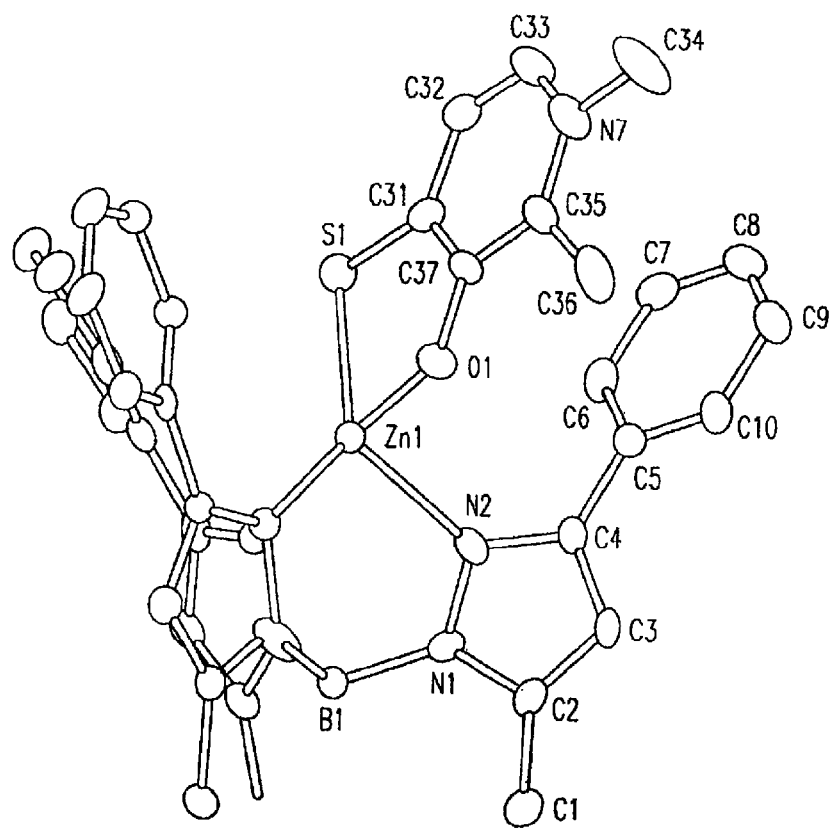

Tris(pyrazolyl)borate complexes of zinc(II) can be used as an initial screen for ZBGs by providing structural and qualitative binding information without the need for sophisticated drug synthesis or protein structure determination. The structures show (FIG. 2 shows a representative example) that all of the novel ZBGs in FIG. 1 can coordinate the zinc(II) ion in a bidentate fashion.[17,22] The metal-ligand bond lengths are compared to those found in the corresponding acetohydroxamate complex.[10] These model-based studies further support the invention described here and are believed to provide additional characterization for the mode of action of these metal chelators toward metalloproteins and MPI design.

The invention will be described further by reference to the following detailed examples, wherein unless otherwise noted, starting materials were obtained from commercial suppliers (Aldrich) and used without further purification. $^1H/^{13}C$ NMR spectra were recorded on a Varian FT-NMR spectrometer running at 300, 400, or 500 MHz located in the Department of Chemistry and Biochemistry, University of California, San Diego. Mass spectra were acquired at the Small Molecule Mass Spectrometry Facility located in the Department of Chemistry and Biochemistry, at the University of California, San Diego. A ThermoFinnigan LCQ-DECA mass spectrometer was used for the APCI and ESI analysis, and the data were analyzed using the Xcalibur software suite. A ThermoFinnigan MAT900XL mass spectrometer was used to acquire the data for the high-resolution mass spectra (HRMS). The value Δ is the error in the measurement (in ppm), given by the equation $\Delta=[(M_E-M_T)/M_T]\times10^6$, where $M_E$ is the experimental mass and $M_T$ is the theoretical mass. The HRMS results were obtained with fast atom bombardment (FAB) or electron impact (EI) as the ion source, 3-nitrobenzyl alcohol as the matrix, and polyethylene glycol or perfluorokerosene as the reference.

The abbreviation DMAP stands for 4-dimethylaminopyridine; TBSCl stands for tert-butyldimethylsilyl chloride; HMDO stands for hexamethyldisiloxane. Illustrative syntheses are disclosed in Schemes 1-10 herein below:

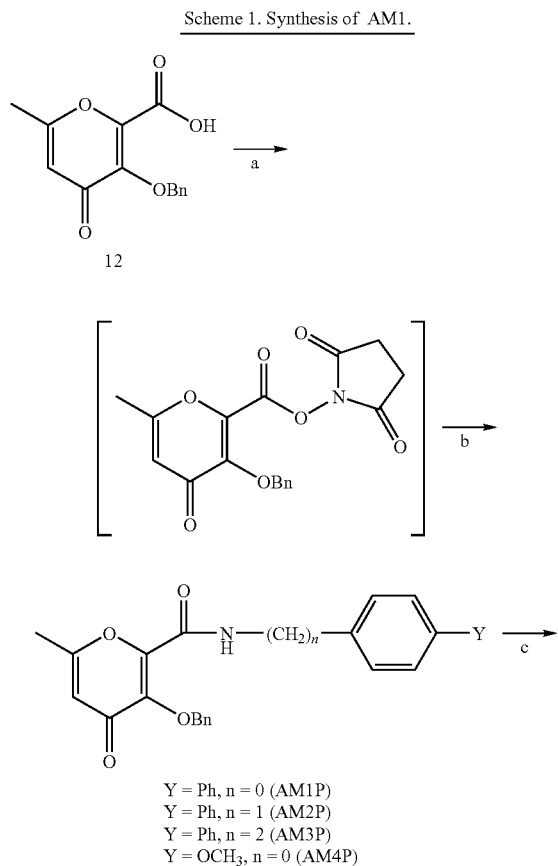

Scheme 1. Synthesis of AM1.

Y = Ph, n = 0 (AM1P)
Y = Ph, n = 1 (AM2P)
Y = Ph, n = 2 (AM3P)
Y = OCH$_3$, n = 0 (AM4P)

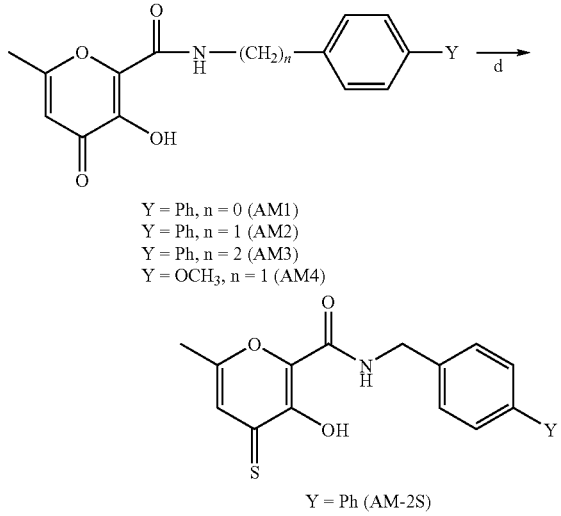

Y = Ph, n = 0 (AM1)
Y = Ph, n = 1 (AM2)
Y = Ph, n = 2 (AM3)
Y = OCH$_3$, n = 1 (AM4)

Y = Ph (AM-2S)

a) NHS, DCC, dry THF, RT; b) 4-phenylphenylamine, 4-phenylbenzylamine, 4-phenylphenethyl amine or 4-methoxybenzyl amine, dry THF, RT, 88% (2 steps); c) Pd/C 10%, H$_2$ 35psi, MeOH, RT, 60%; d) HMDS, P$_4$S$_{10}$ 2-Carboxy-3-benzyloxy-6-methyl-pyran-4(1H)-one (12). This compound was synthesized according to a previous procedure.[23]

3-Benzyloxy-6-methyl-pyran-4(1H)-one-2-carboxy-N-(4-biphenylamide) (AM-1P). To a suspension of 12 (250 mg, 0.95 mmol) in dry THF (25 mL) was added NHS (110 mg, 0.95 mmol) and stirred at room temperature under N$_2$(g) for 30 min. DCC (200 mg, 0.95 mmol) was then added and the reaction was stirred at room temperature under N$_2$(g) for 3 h. The DCU was removed by filtration, and to the resulting filtrate was added 4-biphenylamine (161 mg, 0.95 mmol) as a solid. The reaction was stirred for six days under N$_2$(g) at room temperature. The solvent was removed by evaporation and the residue was taken up in CHCl$_3$. The compound was purified by silica column chromatography (CHC$_3$, with 0-1% MeOH) to yield a white solid (150 mg, 38%). $^1$HNMR (CDCl$_3$, 400 MHz, 25° C.): δ 2.38 (s, 3H, pyrone-CH$_3$), 5.50 (s, 2H, benzyl-CH$_2$), 6.31 (s, 1H, pyrone-H), 7.25 (d, J=8.8 Hz, 2H), 7.34 (m, 1H), 7.41 (m, 4H), 7.47 (m, 4H), 7.56 (m, 3H), 9.78 (br, 1H, amide-H). $^{13}$CNMR (CDCl$_3$, 100 MHz, 25° C.): δ 20.1, 76.3, 115.4, 120.0, 126.7, 127.1, 127.4, 128.7, 129.0, 129.3, 129.4, 135.0, 136.1, 137.6, 140.1, 146.1, 156.4, 165.7, 175.7. ESI-MS (+): m/z 434.04 [M+Na]$^+$. HR-FABMS Calcd for C$_{26}$H$_{22}$NO$_4$: 412.1543. Found: 412.1547.

3-Hydroxy-6-methyl-pyran-4(1H)-one-2-carboxy-N-(4-biphenylamide) (AM-1). To a solution of AM-1P (100 mg, 0.24 mmol) in methanol (100 mL) was added 10% Pd/C (10 mg, 10% w/w). The reaction was placed under H$_2$(g) at 35 psi for 12 h. The catalyst was removed by filtration, and the resulting filtrate was evaporated to an off-white solid and recrystallized from EtOH (60 mg, 77%). $^1$HNMR (d$^3$-MeOD, 300 MHz, 25° C.): δ 2.46 (s, 3H, pyrone-CH$_3$), 6.39 (s, 1H, pyrone-H), 7.34 (m, 1H), 7.43 (t, J=7.2 Hz, 2H), 7.64 (t, J=8.1 Hz, 4H), 7.80 (d, J=8.7 Hz, 2H). $^{13}$CNMR (CDCl$_3$, 100 MHz, 25° C.): δ 20.5, 112.6, 120.8, 126.8, 127.3, 127.7, 128.7, 135.3, 135.7, 140.0, 147.2, 155.4, 165.2, 175.7. ESI-MS (+): m/z 322.06 [M+H]$^+$. Anal. Calcd for C$_{19}$H$_{15}$NO$_4$: C, 69.76; H, 5.27; N, 4.07. Found C, 69.54; H, 5.48; N, 4.30.

3-Benzyloxy-6-methyl-pyran-4(1H)-one-2-carboxy-N-(4-phenylbenzylamide) (AM-2P). To a suspension of 12 (700 mg, 2.7 mmol) in dry THF (40 mL) was added NHS (310 mg, 2.7 mmol) and stirred at room temperature under $N_2(g)$ for 30 min. DCC (557 mg, 2.7 mmol) was then added and the reaction was stirred at room temperature under $N_2(g)$ for 3 h. The DCU was removed by filtration, and to the resulting filtrate was added 4-phenylbenzylamine (495 mg, 2.7 mmol) as a solid. The reaction was stirred overnight under $N_2(g)$ at room temperature. The solvent was removed by evaporation and the residue was taken up in $CHCl_3$. The compound was purified by silica column chromatography ($CHCl_3$ with 0-1% MeOH) to yield a white solid (800 mg, 90%). $^1HNMR$ ($d^6$-DMSO, 400 MHz, 25° C.): δ 2.29 (s, 3H, pyrone-$CH_3$), 4.45 (d, J=6.0 Hz, 2H), 5.15 (s, 2H, benzyl-$CH_2$), 6.38 (s, 1H, pyrone-H), 7.35 (m, 8H), 7.46 (t, J=7.4 Hz, 2H), 7.57 (d, J=8.4 Hz, 2H), 7.62 (d, J=8.4 Hz, 2H), 9.12 (t, J=5.6 Hz, 1H, amide-H). $^{13}CNMR$ (6-DMSO, 100 MHz, 25° C.): δ 19.1, 42.2, 73.4, 114.5, 126.4, 126.5, 127.2, 127.9, 128.0, 128.1, 128.3, 128.7, 136.1, 137.4, 138.7, 139.6, 143.4, 149.0, 158.6, 165.1, 175.1. ESI-MS (+): m/z 448.07 $[M+Na]^+$. HR-FABMS Calcd for $C_{27}H_{24}NO_4$: 426.1700. Found 426.1702.

3-Hydroxy-6-methyl-pyran-4(1)-one-2-carboxy-N-(4-phenylbenzylamide) (AM-2). To a solution of AM-2P (100 mg, 0.24 mmol) in methanol (100 mL) was added 10% Pd/C (10 mg, 10% w/w). The reaction was placed under $H_2(g)$ at 35 psi for 12 h. The catalyst was removed by filtration, and the resulting filtrate was evaporated to an off-white solid (60 mg, 76%). $^1HNMR$ (6-DMSO, 400 MHz, 25° C.): δ 2.31 (s, 3H, pyrone-$CH_3$), 4.53 (d, J=6.4 Hz, 2H), 6.33 (s, 1H, pyrone-H), 7.35 (t, J=7.4 Hz, 1H), 7.43 (q, J=10.8 Hz, 4H), 7.63 (d, J=10.4 Hz, 4H), 9.35 (t, J=6.2 Hz, 1H, amide-H). $^{13}CNMR$ (6-DMSO, 100 MHz, 25° C.): δ 19.4, 42.0, 112.5, 126.4, 126.5, 127.2, 127.9, 128.7, 136.0, 137.4, 138.8, 139.6, 147.3, 162.5, 164.5, 173.3. APCI-MS (+): m/z 335.95 $[M+H]^+$. Anal. Calcd for $C_{20}H_{17}NO_4$: C, 71.63; H, 5.11; N, 4.18. Found C, 71.27; H, 5.43; N, 4.56.

3-Hydroxy-6-methyl-4-thiopyrone-2-carboxy-N-(4-phenylbenzylamide) (AM-2S). 3-Hydroxy-6-methyl-pyran-4(1H)-one-2-carboxy-N-(4-phenylbenzylamide) (AM-2) was synthesized as described above. AM-2 (200 mg, 0.60 mmol, 1.0 equiv) was suspended in benzene (80 mL) and dissolved upon heating to ~65° C. Hexamethyldisiloxane (HMDO, 323 mg, 2.0 mmol, 3.3 equiv) and $P_4S_{10}$ (97 mg, 0.2 mmol, 0.4 equiv) were added to the stirring solution. The reaction flask was fitted with a condenser, and heated to reflux (~90° C.) under a dinitrogen atmosphere for 1.5 h. After heating, a small amount of brown precipitate was removed by vacuum filtration, and the filtrate was concentrated to give a red-orange residue. The residue was purified by silica flash chromatography using a preconditioned column. The column was prepared so as to remove excess metal ions from the silica before loading of the reaction mixture. 3-Hydroxy-2-methyl-4-pyrone (maltol, ~50 mg) was dissolved in 5% MeOH in $CH_2Cl_2$ (~100 mL) and flushed through the packed silica column. Rinsing with the maltol solution was continued until no red color was observed as a mobile band moving through the silica. Upon disappearance of any red color from the column, two more column volumes of the maltol solution were added to ensure complete demetallation of the silica. Finally, the column was flushed with 2×200 mL of 1% MeOH in $CH_2Cl_2$ to remove any remaining maltol. The reaction mixture was then loaded onto the conditioned column and eluted with 1% MeOH in $CH_2Cl_2$ to obtain the desired product as a bright yellow band. After removal of solvent on a rotary evaporator, the product was obtained as a orange microcrystalline solid. Yield: 50%. $^1H$ NMR ($CDCl_3$, 400 MHz, 25° C.): δ 2.43 (s, 3H, pyrone-$CH_3$), 4.71 (d, J=5.6 Hz, 2H, $CH_2$), 7.32 (s, 1H, pyrone-H), 7.36 (m, 1H, Ar—H), 7.44 (m, 4H, Ar—H), 7.58 (m, 4H, Ar—H), 7.99 (br s, 1H, amide-H), 9.53 (s, 1H, pyrone-OH). $^{13}C$ NMR ($CDCl_3$, 100 MHz, 25° C.): δ 19.8, 43.6, 124.2, 126.8, 127.2, 127.3, 128.1, 128.6, 132.2, 136.1, 140.3, 140.6, 149.5, 159.2, 160.3, 190.1. APCI-MS (−): m/z 350.09 $[M-H]^-$. HR-FABMS Calcd for $C_{20}H_{18}NO_3S$ [M+H]: 352.1002. Found, Δ: 352.1004, 0.7 ppm. Anal. Calcd for $C_{20}H_{17}NO_3S$: C, 68.36; H, 4.88; N, 3.99. Found: C, 67.98; H, 4.89; N, 4.16.

3-Benzyloxy-6-methyl-pyran-4(1H)-one-2-carboxy-N-[2-(4-biphenyl)ethylamide)] (AM-3P). To a suspension of 12 (297 mg, 1.1 mmol) in dry THF (25 mL) was added NHS (131 mg, 1.1 mmol) and stirred at room temperature under $N_2(g)$ for 30 min. DCC (236 mg, 1.1 mmol) was then added and the reaction was stirred at room temperature under $N_2(g)$ for 3 h. The DCU was removed by filtration, and to the resulting filtrate was added 2-(4-biphenyl)ethylamide) (217 mg, 1.1 mmol) as a solid. The reaction was stirred overnight under $N_2(g)$ at room temperature. The solvent was removed by evaporation and the residue was taken up in $CHCl_3$. The compound was purified by silica column chromatography ($CH_2Cl_2$) to yield a white solid (450 mg, 90%). $^1HNMR$ ($CDCl_3$, 300 MHz, 25° C.): δ 2.29 (s, 3H, pyrone-$CH_3$), 2.72 (t, J=6.9 Hz, 2H), 3.50 (q, J=6.9 Hz, 2H), 5.25 (s, 2H, benzyl-$CH_2$), 6.23 (s, 1H, pyrone-H), 7.20 (m, 4H), 7.30 (m, 4H), 7.40 (t, J=6.9 Hz, 2H), 7.53 (t, J=6.5 Hz, 4H), 7.83 (t, J=5.1 Hz, 1H, amide-H). $^{13}CNMR$ ($CDCl_3$, 100 MHz, 25° C.): δ 22.0, 36.7, 43.1, 75.0, 117.2, 128.8, 129.1, 129.2, 130.6, 130.7, 130.9, 131.0, 131.1, 137.2, 139.4, 141.4, 142.5, 147.6, 148.4, 160.8, 167.5, 177.9. ESI-MS (+): m/z 462.10 $[M+Na]^+$.

3-Hydroxy-6-methyl-pyran-4(1H)-one-2-carboxy-N-[2-(4-biphenyl)ethylamide)] (AM-3). To a suspension of AM-3P (300 mg, 0.68 mmol) in methanol (50 mL) was added 10% Pd/C (30 mg, 10% w/w). The reaction was placed under $H_2(g)$ at 35 psi for 12 h. The catalyst was removed by filtration, and the resulting filtrate was evaporated to an off-white solid (205 mg, 86%). $^1HNMR$ ($CDCl_3$, 400 MHz, 25° C.): δ 2.31 (s, 3H, pyrone-$CH_3$), 3.00 (t, J=7.2 Hz, 2H), 3.75 (q, J=6.8 Hz, 2H), 6.26 (s, 1H, pyrone-H), 6.89 (br, 1H, amide-H), 7.35 (m, 3H), 7.45 (t, J=7.2 Hz, 2H), 7.59 (d, J=6.8 Hz, 4H). $^{13}CNMR$ ($CDCl_3$, 100 MHz, 25° C.): δ 20.3, 35.1, 40.8, 113.0, 126.8, 127.2, 127.3, 128.7, 129.0, 133.3, 136.9, 137.1, 137.3, 139.6, 140.4, 182.0. HR-FABMS Calcd for $C_{21}H_{20}NO_4$: 350.1387. Found 350.1379. Anal. Calcd for $C_{21}H_{19}NO_4 \cdot 0.20H_2O$: C, 71.46; H, 5.54; N, 3.97. Found C, 71.31; H, 5.66; N, 4.34.

3-Hydroxy-6-methyl-pyran-4(1H)-one-2-carboxy-N-[4-methoxybenzylamide)] (AM-4). AM-4P (120 mg, 0.32 mmol) was dissolved in 7.3 mL of a 1:1 solution of concentrated HCl and glacial acetic acid. The solution was stirred under $N_2(g)$ for 24 h at room temperature. The reaction was co-evaporated with methanol (2×20 mL), and dried under vacuum to yield a crude off-white solid, which was recrystallized from EtOH (55 mg, 60%). $^1HNMR$ ($CDCl_3$, 400 MHz, 25° C.): δ 2.31 (s, 3H, pyrone-$CH_3$), 3.80 (s, 3H, methoxy-$CH_3$), 4.55 (d, J=6.0 Hz, 2H), 6.24 (s, 1H, pyrone-H), 6.88 (d, J=8.4 Hz, 2H), 7.20 (br, 1H, amide-H), 7.28 (d, J=8.8 Hz, 2H). $^{13}CNMR$ ($CDCl_3$, 100 MHz, 25° C.): δ 20.2, 43.0, 55.3, 113.1, 114.1, 128.7, 129.3, 132.4, 148.2, 159.1, 174.0, 181.0. HR-FABMS Calcd for $C_{15}H_{16}NO_5$: 290.1023. Found: 290.1022. Anal. Calcd for $C_{15}H_{15}NO_5$: C, 62.28; H, 5.23; N, 4.84. Found: C, 61.89; H, 5.16; N, 4.95.

Scheme 2. Synthesis of AM-5, AM-6.

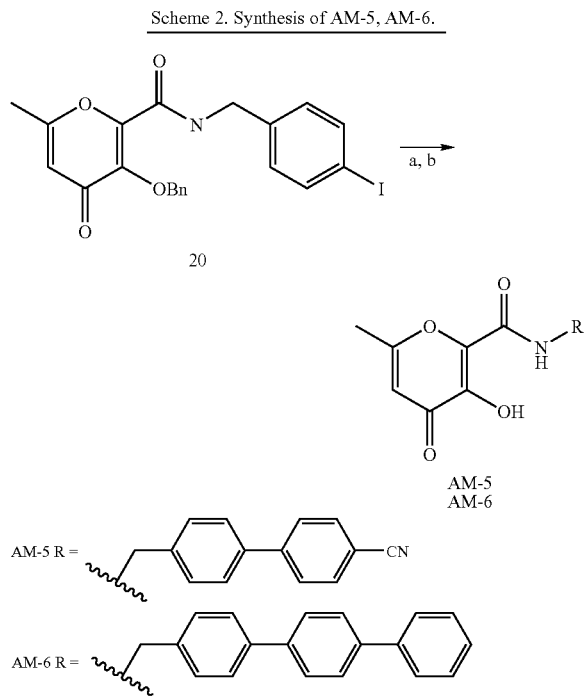

(a) ArB(OH)$_2$, 2 M K$_2$CO$_3$, Pd(C$_2$H$_3$O$_2$)$_2$, PPh$_3$, toluene, 135° C., 40-85%; (b) 10% Pd/C, H$_2$, 35 psi, MeOH or 1:1 HCl:CH$_3$COOH, 60-91%

3-Benzyloxy-6-methyl-pyran-4(1H)-one-2-carboxy-N-(4-iodobenzylamide) (20). To a suspension of 12 (2.4 g, 9.4 mmol) in dry THF (100 mL) was added N-hydroxysuccinamide (NHS) (1.1 g, 9.4 mmol) and stirred at room temperature under N$_2$(g) for 30 min. 1,3-Dicyclohexylcarbodiimide (DCC) (1.9 g, 9.4 mmol) was then added and the reaction was stirred at room temperature under N$_2$(g) for 3 h. The N,N-dicyclohexylurea (DCU) was filtered and to the resulting filtrate was added 4-iodobenzylamine (2.2 g, 9.4 mmol) as a solid. The reaction was stirred overnight under N$_2$(g) at 60° C. The solvent was removed by evaporation and the residue was taken up in CHCl$_3$. The compound was purified by silica column chromatography (CHCl$_3$) to yield a white solid (3 g, 67%). $^1$HNMR (CDCl$_3$, 300 MHz, 25° C.): δ 2.37 (s, 3H, pyrone-CH$_3$), 4.33 (d, J=6.0 Hz, 2H), 5.34 (s, 2H, benzyl-CH$_2$), 6.29 (s, 1H, pyrone-H), 6.89 (d, J=8.4 Hz, 2H), 7.30 (m, 5H), 7.60 (d, J=8.4 Hz, 2H), 8.07 (br, 1H, amide-H). $^{13}$CNMR (CDCl$_3$, 100 MHz, 25° C.): δ 20.1, 43.2, 75.3, 94.2, 115.3, 128.7, 128.9, 129.0, 129.7, 135.0, 136.7, 137.6, 145.9, 165.6, 175.8. ESI-MS (+): m/z 497.94 [M+Na]$^+$.

3-Benzyloxy-6-methyl-pyran-4(1H)-one-2-carboxy-N-4-(4-cyanophenyl)benzylamide) (AM-5P). To a solution of 20 (300 mg, 0.63 mmol) in toluene (20 mL) and 2M aqueous K$_2$CO$_3$ (20 mL) was added 4-cyanophenylboronic acid (139 mg, 0.95 mmol), Pd(C$_2$H$_3$O$_2$)$_2$ (28 mg 0.13 mmol), and PPh$_3$ (34 mg, 0.13 mmol). The reaction was heated to reflux at 135° C. under N$_2$(g) for 10 days. The reaction was extracted with 3×30 mL toluene and the organic layer was washed with 30 mL water. The organic layer was dried over anhydrous MgSO$_4$ and filtered. The resulting filtrate was evaporated to yield a light yellow solid. The product was purified by silica column chromatography (CH$_2$Cl$_2$ with 0-1% MeOH) to yield an off-white solid (100 mg, 40%). $^1$HNMR (CDCl$_3$, 400 MHz, 25° C.): δ 2.35 (s, 3H, pyrone-CH$_3$), 4.45 (d, J=6.0 Hz, 2H), 5.33 (s, 2H, benzyl-CH$_2$), 6.27 (s, 1H, pyrone-H), 7.23 (m, 7H), 7.50 (d, J=8.0 Hz, 2H), 7.64 (d, J=8.0 Hz, 2H), 7.71 (d, J=8.4 Hz, 2H), 8.13 (br, 1H, amide-H). $^{13}$CNMR (CDCl$_3$, 100 MHz, 25° C.): δ 20.0, 43.3, 75.2, 110.9, 115.3, 118.7, 127.4, 127.5, 128.5, 128.6, 128.9, 129.0, 132.5, 137.7, 138.3, 144.8, 145.9, 158.9, 165.6, 175.8. ESI-MS (+): m/z 473.13 [M+Na]$^+$.

3-Hydroxy-6-methyl-pyran-4(1H)-one-2-carboxy-N-(4-(4-cyanophenyl)benzylamide) (AM-5). To a solution of AM-5P (75 mg, 0.17 mmol) in methanol (80 mL) was added 10% Pd/C (8 mg, 10% w/w). The reaction was placed under H$_2$(g) at 35 psi for 20 h. The catalyst was removed by filtration, and the resulting filtrate was evaporated to a white solid (40 mg, 62%). $^1$HNMR (CDCl$_3$, 400 MHz, 25° C.): δ 2.36 (s, 3H, pyrone-CH$_3$), 4.71 (d, J=6.0 Hz, 2H), 6.29 (s, 1H, pyrone-H), 7.23 (br, 1H, amide-H), 7.47 (d, J=8.4 Hz, 2H), 7.60 (d, J=8.0 Hz, 2H), 7.67 (d, J=8.0 Hz, 2H), 7.74 (d, J=8.4 Hz, 2H). 7.41 (m, 4H), 7.47 (m, 4H), 7.56 (m, 3H). $^{13}$CNMR (CDCl$_3$, 100 MHz, 25° C.): δ 19.6, 42.6, 110.3, 112.6, 118.5, 127.1, 127.3, 128.1, 132.3, 136.0, 137.7, 138.0, 144.8, 147.7, 147.8, 162.8, 165.1. HR-FABMS Calcd for C$_{21}$H$_{17}$N$_2$O$_4$: 361.1183. Found: 361.1188. Anal. Calcd for C$_{21}$H$_{16}$N$_2$O$_4$·1.5H$_2$O C, 65.11; H, 4.94; N, 7.23. Found: C, 64.95; H, 4.88; N, 6.87.

3-Benzyloxy-6-methyl-pyran-4(1H)-one-2-carboxy-N-(4-biphenylbenzylamide) (AM-6P). To a solution of 20 (200 mg, 0.42 mmol) in toluene (20 mL) and 2M aqueous K$_2$CO$_3$ (20 mL) was added 4-biphenylboronic acid (83 mg, 0.42 mmol), Pd(C$_2$H$_3$O$_2$)$_2$ (9.2 mg 0.04 mmol), and PPh$_3$ (11 mg, 0.04 mmol). The reaction was heated to reflux at 135° C. under N$_2$(g) for 24 h. The reaction was extracted with 3×30 mL toluene and the organic layer was washed with 30 mL water. The organic layer was dried over anhydrous MgSO$_4$ and filtered. The resulting filtrate was evaporated to yield a yellow solid. The product was purified by silica column chromatography (CHCl$_3$ with 0-5% MeOH) to an off-white solid (180 mg, 85%). $^1$HNMR (CDCl$_3$, 400 MHz, 25° C.): δ 2.38 (s, 3H, pyrone-CH$_3$), 4.48 (d, J=6.0 Hz, 2H), 5.35 (s, 2H, benzyl-CH$_2$), 6.29 (s, 1H, pyrone-H), 7.23 (m, 7H), 7.38 (t, J=8.4 HZ, 1H), 7.46 (t, J=8.0 HZ, 2H), 7.58 (d, J=8.0 Hz, 2H), 7.67 (m, 6H), 8.13 (t, J=5.4 Hz 1H, amide-H). $^{13}$CNMR (CDCl$_3$, 100 MHz, 25° C.): 820.1, 43.6, 75.2, 115.3, 126.9, 127.2, 127.3, 127.4, 128.4, 128.7, 129.0, 129.1, 131.2, 135.0 136.2, 139.3, 140.0, 140.1, 140.4, 159.0, 165.6, 175.9. ESI-MS (+): m/z 523.98 [M+Na]$^+$.

3-Hydroxy-6-methyl-pyran-4(1H)-one-2-carboxy-N-(4-biphenylbenzylamide) (AM-6). To AM-6P (160 mg, 0.32 mmol) was added 5 mL of a 1:1 solution of concentrated HCl and glacial acetic acid. The suspension was stirred under N$_2$(g) for 24 h at room temperature. The reaction was co-evaporated with methanol (2×20 mL), and dried under vacuum to yield a white solid (120 mg, 91%). $^1$HNMR (CDCl$_3$, 400 MHz, 25° C.): δ 2.35 (s, 3H, pyrone-CH$_3$), 4.70 (d, J=5.6 Hz, 2H), 6.28 (s, 1H, pyrone-H), 7.14 (br, 1H, amide-H), 7.25 (m, 3H), 7.37 (t, J=7.4 Hz, 1H), 7.46 (t, J=8.4 Hz, 3H), 7.67 (m, 6H). $^{13}$CNMR (CDCl$_3$, 100 MHz, 25° C.): δ 20.4, 43.3, 113.1, 126.9, 127.2, 127.3, 127.4, 127.5, 128.4, 128.7, 135.3, 135.8, 139.1 140.2, 140.3, 148.1, 140.4, 162.9, 164.3, 173.9. HR-FABMS Calcd for C$_{26}$H$_{22}$NO$_4$: 412.1543. Found: 412.1548. Anal. Calcd for C$_{26}$H$_{21}$NO$_4$·0.9H$_2$O: C, 73.08; H, 5.26; N, 3.06. Found: C, 73.02; H, 5.37; N, 3.28.

Scheme 3. Synthesis of CA1.

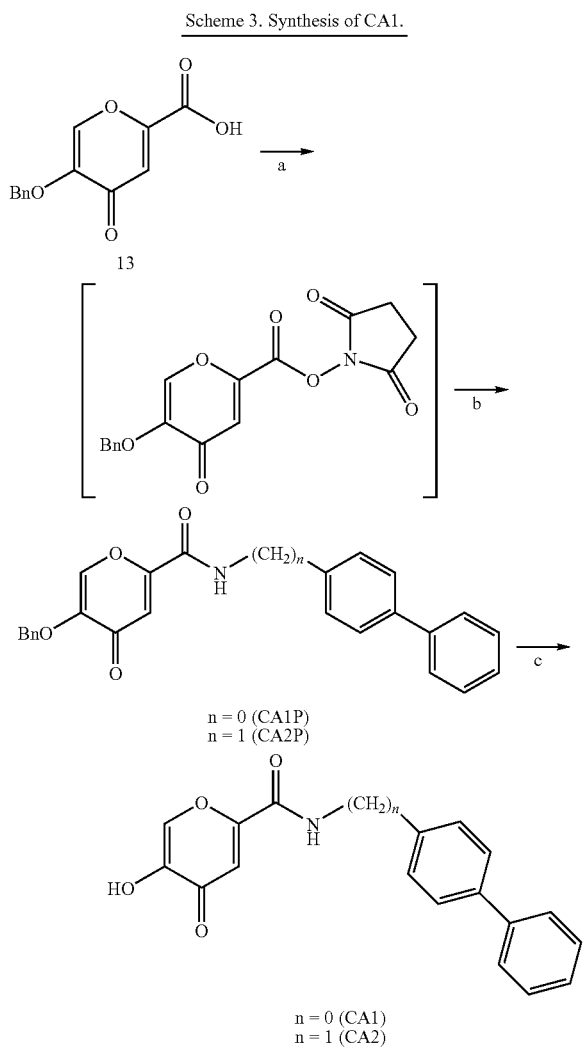

n = 0 (CA1P)
n = 1 (CA2P)

n = 0 (CA1)
n = 1 (CA2)

a) NHS, DCC, dry THF, RT; b) 4-phenylbenzylamine or biphenylamine, dry THF, 80% (2 steps); c) Pd/C 10%, H$_2$ 35psi, MeOH, RT, 75%.

5-Benzyloxy-pyran-4(1H)-one-2-carboxylic acid (13). Was synthesized according to a previous procedure.[24] Yield 74% $^1$H NMR (300 MHz CDCl$_3$) δ 3.5 (s, 2H, benzyl-CH$_2$), 6.9 (s, 1H, CH$_2$), 7.4 (m, 5H, phenyl-H), 8.4 (s, 1H, pyrone-H).

NHS activation of 5-Benzyloxy-pyran-4(1H)-one-2-carboxylic acid (benzyl comenic acid). To a solution of (13) (300 mg 1.3 mmol) in dry THF (20 mL) was added NHS (150 mg 1.3 mmol). The reaction mixture was stirred for 30 minutes at room temperature under a N$_2$(g) atmosphere. DCC (268 mg 1.3 mmol) was added to the stirring solution and the mixture was continued to stir for 3 hours until TLC showed consumption of starting material. The DCU was filtered and the resulting filtrate was used in situ to synthesize CA1P and CA2P.

CA2P. To the above solution was added phenyl benzyl amine (238 mg 1.3 mmol) in THF (20 mL) dropwise. The reaction was stirred at room temperature over night under a N$_2$(g) atmosphere. The product precipitated as a white solid, which was filtered, washed with 20 mL methanol and dried to yield 375 mg. Yield 73% $^1$H NMR (400 MHz d-DMSO) δ 4.5 (d, J=5.6 Hz, 2H, CH$_2$), 5.0 (s, 2H, benzyl-CH$_2$), 6.9 (s, 1H, pyrone-H), 7.4 (m, 10H, phenyl-H), 7.6 (m, 4H, phenyl-H), 8.3 (s, 1H, pyrone-H), 9.5 (t, J=12 Hz, 1H, amide-H). (+)-ESIMS: m/z 434.1 [M+Na]$^+$. CA2. To a suspension of CA2P (250 mg 0.63 mmol) in THF (130 mL) was added 25 mg of 10% Pd/C and placed under H$_2$ at 35 psi overnight at room temperature. The catalyst was filtered off and the filtrate was evaporated to an off-white solid, which was washed with 20 mL benzene and dried to yield 120 mg of a white solid. Yield 62% $^1$H NMR (400 MHz d-DMSO) δ 4.5 (d, J=6.0 Hz, 2H, CH$_2$), 6.9 (s, 1H, pyrone-H), 7.4 (m, 5H, phenyl-H), 7.6 (m, 4H, phenyl-H), 8.1 (s, 1H, pyrone-H), 9.5 (t, J=12 Hz, 1H, amide-H), 9.6 (br s, 1H, OH). (−)-ESIMS: m/z 320.02 [M—H].

CA1P. The same procedure was used as in the synthesis of CA2P but using p-aminobiphenyl. Yield 78% $^1$H NMR (400 MHz d-DMSO) δ 5.0 (s, 2H, benzyl-CH$_2$), 7.0 (s, 1H, pyrone-H), 7.4 (m, 8H, phenyl-H), 7.7 (t, 4H, J=15.0 Hz, phenyl-H), 7.8 (d, J=7.8 Hz, 2H, phenyl-H), 8.3 (s, 1H, pyrone-H), 10.7 (br, 1H, amide-H). (+)-APCIMS: m/z 398.02 [M$^+$+H].

CA1. The same procedure was used as in the synthesis of CA2 to yield a light yellow solid. Yield 43% $^1$H NMR (400 MHz d-DMSO) δ 7.0 (s, 1H, pyrone-H), 7.4 (br s, 1H, phenyl-H), 7.4 (t, J=15.2 Hz, 2H, phenyl-H), 7.7 (t, J=15.2 Hz, 4H, phenyl-H), 7.7 (d, J=8.8 Hz, 2H, phenyl-H), 8.2 (s, 1H, pyrone-H), 8.7 (br, 1H, amide-H), 10.7 (s, 1H, OH).

Scheme 4. Synthesis of CK2-3.

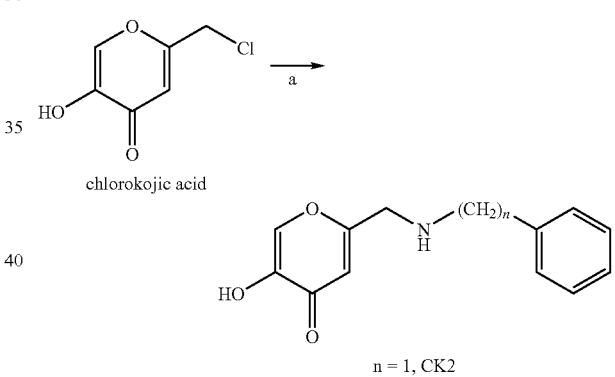

chlorokojic acid n = 1, CK2
n = 2, CK3 a) benzylamine or phenethylamine, N(CH$_2$CH$_3$)$_3$, DMF, RT, 52%.

CK2. To a solution of chlorokojic acid (3 g 18.7 mmol) and benzylamine (2.25 mL 20.6 mmol) in DMF (15 mL) was added dropwise triethylamine (7.8 mL 56 mmol). The reaction mixture was stirred overnight at room temperature under a N$_2$(g) atmosphere. Water (60 mL) was added to the reaction mixture and the product was extracted with 3×200 mL CH$_2$Cl$_2$, dried with sodium sulfate, and filtered. The organic layer was evaporated to a dark yellow oil and purified by column chromatography on silica gel (elutant: 2-5% MeOH in CH$_2$Cl$_2$) to yield 2.2 g of a light yellow solid. Yield 52% $^1$H NMR (300 MHz d-DMSO) δ 2.5 (br m, 1H, NH), 3.5 (s, 2H, CH$_2$)), 3.7 (s, 2H, CH$_2$), 6.4 (s, 1H, pyrone-CH$_2$), 7.3 (m, 5H, phenyl-H), 8.0 (s, 1H, pyrone-H).

CK3. The same procedure was used as in the synthesis of CK2, substituting phenethylamine for benzylamine. Yield 26% $^1$H NMR (300 MHz CDCl$_3$) (2.8 (br quad, 4H, CH$_2$CH$_2$), 3.5 (s, 1H, NH)), 3.7 (s, 2H, CH$_2$), 6.4 (s, 1H, pyrone-H), 7.3 (m, 5H, phenyl-H), 7.9 (s, 1H, pyrone-H).

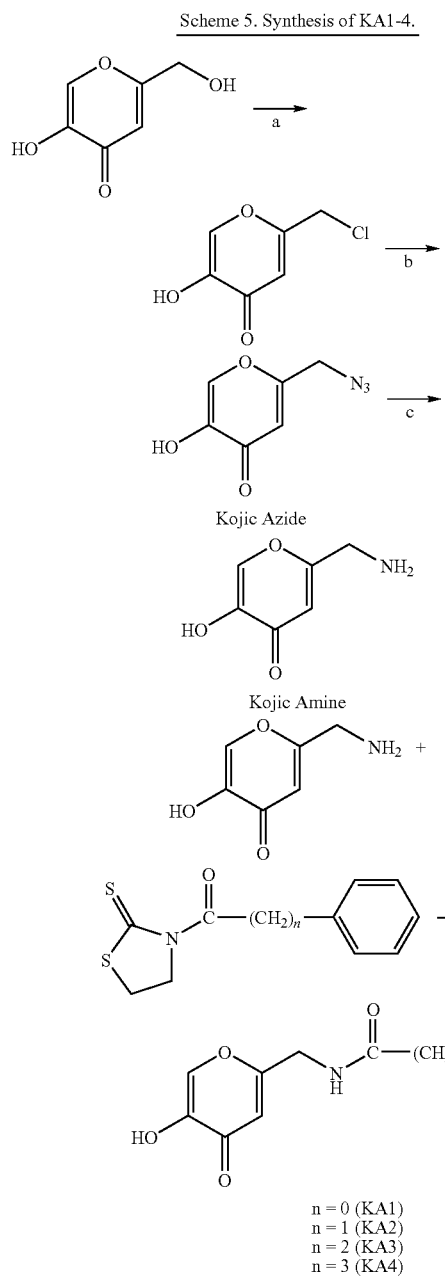

Scheme 5. Synthesis of KA1-4.

Kojic Azide

Kojic Amine n = 0 (KA1)
n = 1 (KA2)
n = 2 (KA3)
n = 3 (KA4)

a) SOCl$_2$, dry CH2Cl2, RT, 88%; b) NaN$_3$, DMF, RT, 80%; c) Lindlar Catalyst, H$_2$, 35 psi, MeOH, RT, 90%; d) phenyl(2-thioxothiazolidin-3-yl)methanone, N(CH$_2$CH$_3$)$_3$, MeOH, RT, 51%.

Kojic Amine. Kojic Azide (325 mg 1.94 mmol) was dissolved in 100 mL EtOH. To this solution was added Lindlar catalyst. The azide was hydrogenated at 35 psi for 1 hour at room temperature. Filtered off catalyst and rotovapped to light brown solid. Dissolved in hot water and filtered off insolubles. Rotovapped filtrate to a white-tan solid 250 mg (91%). $^1$HNMR (DMSO-d$_6$, 400 MHz, 25° C.) δ 3.52 (s, 2H, CH$_2$), 6.38 (s, 1H), 7.98 (s, 1H). IR (KBr): ν 1216, 1289, 1575, 1659 (C=O), 3374-2683 (b, NH$_3$, OH) cm$^{-1}$. MS ESI 142.1 (M+H), 140.0 (M−H).

General Procedure for MPIs KA1-4. Kojic amine (200 mg 1.4 mmol) was dissolved in methanol (60 mL). To this solution was added triethylamine (197.4 uL 1.4 mmol) and the corresponding activated amide (see above) dissolved in CH$_2$Cl$_2$. The solution was stirred overnight at room temperature under a N$_2$(g) atmosphere. The reaction mixture was evaporated to an oil which was purified by column chromatography on silica gel (elutant: 5-10% CH$_2$Cl$_2$/MeOH).

KA1. Yield 51% $^1$H NMR (400 MHz d-DMSO) δ 4.3 (d, J=5.4 Hz 2H, CH$_2$), 6.3 (s, 1H, pyrone-H), 7.5 (m, 3H, phenyl-H), 7.9 (d, J=6.9 Hz, 2H, phenyl-H), 8.0 (s, 1H, pyrone-H), 9.1 (t, J=12 Hz, 1H, amide-H).

KA2. Yield 30% $^1$H NMR (400 MHz d-DMSO) δ 3.5 (s, 2H, CH$_2$), 4.1 (d, J=5.4 Hz 2H, CH$_2$), 6.2 (s, 1H, pyrone-H), 7.3 (m, 5H, phenyl-H), 8.0 (s, 1H, pyrone-H), 8.5 (t, J=12 Hz, 1H, amide-H). $^{13}$CNMR (100 MHz, d-DMSO) δ 42.1, 110.3, 126.4, 128.2, 128.9, 135.8, 139.3, 145.5, 164.9, 170.4, 173.5.

KA3. Yield 43% $^1$H NMR (400 MHz d-DMSO) δ 2.5 (t, J=16 Hz, 2H, CH$_2$), 2.8 (t, J=15.6 Hz, 2H, CH$_2$), 4.1 (d, J=6.0 Hz 2H, CH$_2$), 6.2 (s, 1H, pyrone-H), 7.2 (m, 5H, phenyl-H), 8.0 (s, 1H, pyrone-H), 8.4 (t, J=12 Hz, 1H, amide-H), 9.1 (br s, 1H, pyrone-OH).

KA4. Yield 70% $^1$H NMR (400 MHz d-DMSO) δ 1.8 (quintuplet, J=15.2 Hz 2H, CH$_2$)), 2.2 (t, J=16 Hz, 2H, CH$_2$), 2.6 (t, J=15.6 Hz, 2H, CH$_2$), 4.1 (d, J=6.0 Hz 2H, CH$_2$), 6.2 (s, 1H, pyrone-H), 7.2 (d, J=7.6 Hz, 2H, phenyl-H), 7.3 (t, J=15.2 Hz, 3H, phenyl-H), 8.0 (s, 1H, pyrone-H), 8.4 (t, J=12 Hz, 1H, amide-H), 9.1 (br s, 1H, pyrone-OH).

Scheme 6. Synthesis of HP32A, HP32B, and HP32C.

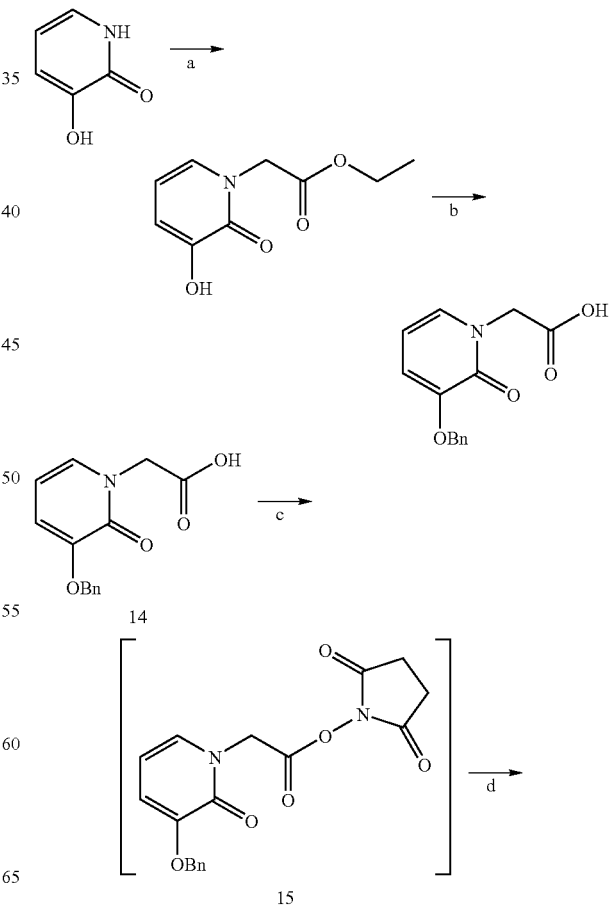

14

15

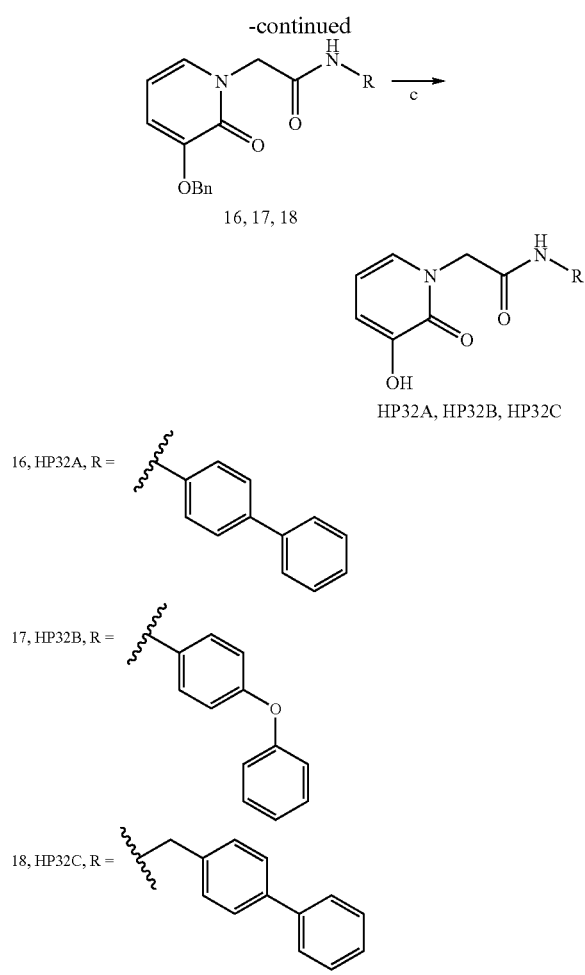

a) BrCH₂OEt, neat, 160° C., 40%; b) BnBr, NaOH, MeOH/H₂O, 95° C., 80%; c) DCC, NHS, DMF, 90%; d) H₂NR, dry CH₂Cl₂, RT, 50%; e) Pd/C 10%, H₂ (g) 35psi, EtOH, RT, 40%.

3-(Benzyloxy)-1-[[(succinimidyloxy)carbonyl]methyl]-2 (1H)-pyridinone (15). To a stirred solution of 14[25] (0.95 g, 3.7 mmol) in 50 mL of dimethylformamide (DMF) were added solutions of N-hydroxysuccinimide (NHS, 0.44 g, 3.9 mmol) and dicyclohexylcarbodiimide (DCC, 0.80 g, 3.9 mmol) each by dropwise addition and each in DMF (5 mL). The reaction mixture was protected from light with aluminum foil and stirred under a dinitrogen atmosphere at RT overnight. Glacial acetic acid (100 µL) was added. The solvent was removed by rotary evaporation to yield the crude product. Recrystallization from ethyl acetate (EtOAc) and isolation by vacuum filtration gave the pure product as white crystalline needles. Another batch of product was isolated by concentrating the EtOAc filtrate followed by cooling the mixture to 0° C. overnight and isolating the crystals by vacuum filtration the following day. Yield: 88%. ¹H NMR (d⁶-DMSO, 400 MHz, 25° C.): δ 2.80 (s, 4H, succinimidyl-H), 5.02 (s, 2H, —CH₂—), 5.17 (s, 2H, —CH₂—), 6.20 (t, J=7.2 Hz, 1H, Ar—H), 6.95 (d, J=7.6 Hz, 1H, Ar—H), 7.39 (m, 6H, Ar—H, benzyl-H).

3-Benzyloxy-1-[(biphenylcarbamoyl)methyl]-2-(1H)-pyridinone (16). 15 (0.5 g, 1.4 mmol) was dissolved in 40 mL of CH₂Cl₂. 4-aminobiphenyl (0.26 g, 1.5 mmol) was dissolved in 10 mL of CH₂Cl₂ to yield a chocolate brown solution and was quickly added to the stirring solution of 15. The reaction flask was protected from light with aluminum foil and stirred at room temperature under a dinitrogen atmosphere for 22 h. A white solid was removed by vacuum filtration. The CH₂Cl₂ filtrate layer was washed with 0.05 M aqueous sodium bicarbonate solution (3×25 mL). The methylene chloride layer was washed with ddH₂O (1×25 mL) and then dried over anhydrous sodium sulfate. The clear, colorless solution was concentrated by rotary evaporation to yield a white solid. Yield: 51%. ¹H NMR (d⁶-DMSO, 400 MHz, 25° C.): δ 4.77 (s, 2H, —CH₂—), 5.02 (s, 2H, —CH₂—), 6.16 (t, J=7.0 Hz, 1H, Ar—H), 6.94 (d, J=5.6 Hz, 1H, Ar—H), 7.39 (m, 9H, Biphenyl-H), 7.64 (m, 6H, Ar—H, Bz-H), 10.43 (d, J=6.9 Hz, 1H, —NH—). ESI-MS: m/z 433.1 [M+Na]⁺, m/z 411.0 [M+H]⁺.

3-Hydroxy-1-[(biphenylcarbamoyl)methyl]-2-(1H)-pyridinone (HP32A). 16 (200 mg, 0.5 mmol) was suspended in 100 mL of EtOH. 10% (w/w, 38 mg) of 10% Pd/C catalyst was added to the hydrogenation flask (500 mL Pyrex® Parr reaction bottle tested to 120 psi, max. working pressure of 60 psi). The hydrogen pressure was set to 35 psi with agitation, and the process went on for 10 h. The catalyst was removed by vacuum filtration and separated from the product by dissolving the white precipitate in 125 mL hot CH₂Cl₂ and MeOH. The clear solution was concentrated by rotary evaporation to yield a white solid. The solid was washed with MeOH to remove residual DCU and recrystallized from EtOH to yield a white, feathery microcrystalline solid. Yield: 31%. ¹H NMR (d⁶-DMSO, 400 MHz, 25° C.): δ 4.79 (s, 2H, —CH₂—), 6.12 (t, J=7.2 Hz, 1H, Ar—H), 6.73 (d, J=7.2 Hz, 1H, Ar—H), 7.15 (d, J=6.8 Hz, 1H, Ar—H), 7.31 (t, J=7.2 Hz, 1H, Biphenyl-H), 7.42 (t, J=7.0 Hz, 2H, Biphenyl-H), 7.64 (m, 6H, Biphenyl-H), 9.07 (s, 1H, —OH), 10.45 (s, 1H, —NH—). ESI-MS: m/z 320.9 [M+H]⁺, m/z 319.1 [M–H]⁻. Anal. Calcd for C₁₉H₁₆N₂O₃.½H₂O: C, 69.29; H, 5.20; N, 8.51. Found: C, 68.96; H, 5.60; N, 8.34.

3-Benzyloxy-1-[(phenoxycarbamoyl)methyl]-2-(1H)-pyridinone (17). 15 (1.0 g, 2.8 mmol) was dissolved in 100 mL of dry CH₂Cl₂. 4-phenoxyaniline (0.57 g, 3.1 mmol) was dissolved in 10 mL of CH₂Cl₂ to yield a clear, brown solution and was quickly added to the stirring solution of 15. The reaction flask was protected from light with aluminum foil and stirred at room temperature under a dinitrogen atmosphere for 21 h. The resultant clear, light brown CH₂Cl₂ solution was washed with 0.05 M aqueous sodium bicarbonate solution (3×50 mL). The methylene chloride layer was washed with ddH₂O (1×50 mL) and then dried over anhydrous sodium sulfate. The clear, colorless solution was concentrated by rotary evaporation to yield a white solid. Yield: 55%. ¹H NMR (d⁶-DMSO, 300 MHz, 25° C.): δ 4.73 (s, 2H, —CH₂—), 5.01 (s, 2H, —CH₂—), 6.15 (t, J=7.2 Hz, 1H, Ar—H), 7.35 (m, 16H, 2 Ar—H, Bz-H, Phenoxy-H), 10.36 (s, 1H, —NH—).

3-Hydroxy-1-[(phenoxycarbamoyl)methyl]-2-(1H)-pyridinone (HP32B). 17 (350 mg, 0.8 mmol) was suspended in 175 mL of EtOH. 10% (w/w, 38 mg) of 10% Pd/C catalyst was added to the hydrogenation flask (500 mL Pyrex® Parr reaction bottle tested to 120 psi, max. working pressure of 60 psi). The hydrogen pressure was set to 35 psi with agitation, and the process went on for 41 h. The catalyst was removed by vacuum filtration and separated from the product by dissolving the white precipitate in 125 mL hot CH₂Cl₂ and MeOH and THF. The clear solution was concentrated by rotary evaporation to yield a white solid. The solid was washed with MeOH to remove residual DCU to yield a white, feathery microcrystalline solid. Yield: 57%. ¹H NMR (d⁶-DMSO, 400 MHz, 25° C.): δ 4.75 (s, 2H, —CH₂—), 6.11 (t, J=7.0 Hz, 1H, Ar—H), 6.72 (d, J=7.2 Hz, 1H, Ar—H), 6.97 (m, 4H, Phenoxy-H), 7.11 (m, 2H, Ar—H, Phenoxy-H), 7.36 (t, J=7.2 Hz, 2H, Phenoxy-H), 7.58 (d, J=6.8 Hz, 2H, Phenoxy-H), 9.03 (s, 1H, —OH), 10.36 (s, 1H, —NH—). APCI-MS: m/z 336.9 [M+H]⁺. Anal. Calcd for C₁₉H₁₆N₂O₄: C, 67.85; H, 4.79; N, 8.33. Found: C, 67.75; H, 5.07; N, 8.49.

3-Benzyloxy-1-[(phenylbenzylcarbamoyl)methyl]-2-(1H)-pyridinone (18). 15 (0.5 g, 1.4 mmol) was dissolved in 50 mL of dry CH₂Cl₂. 4-phenylbenzylamine (0.28 g, 1.5 mmol) was dissolved in 10 mL of dry CH₂Cl₂ to yield an almost clear, colorless solution and was quickly added to the stirring solution of 15. The reaction flask was protected from light with aluminum foil and stirred at room temperature under a dinitrogen atmosphere for 18 h. A white solid was removed by vacuum filtration. A second crop of white precipitate was isolated after cooling the filtrate at 4° C. for 3 h. The CH₂Cl₂ filtrate layer was washed with 0.05 M aqueous sodium bicarbonate solution (3×25 mL). The methylene chloride layer was washed with ddH₂O (1×25 mL) and then dried over anhydrous sodium sulfate. The clear, colorless solution was concentrated by rotary evaporation to yield a white solid. Yield: 55%. ¹H NMR (d⁶-DMSO, 400 MHz, 25° C.): δ 4.33 (d, J=6.0 Hz, 2H, —CH₂—), 4.61 (s, 2H, —CH₂—), 5.00 (s, 2H, —CH₂—), 6.12 (t, J=7.2 Hz, 1H, Ar—H), 6.91 (d, J=7.6 Hz, 1H, Ar—H), 7.22 (d, J=6.8 Hz, 1H, Ar—H), 7.39 (m, 9H, Phenyl-H, Bz-H), 7.62 (m, 5H, Bz-H), 8.70 (t, J=5.8 Hz, 1H, —NH—).

3-Hydroxy-1-[(phenylbenzylcarbamoyl)methyl]-2-(1H)-pyridinone (HP32C). 18 (280 mg, 0.7 mmol) was suspended in 150 mL of EtOH. 10% (w/w, 38 mg) of 10% Pd/C catalyst was added to the hydrogenation flask (500 mL Pyrex® Parr reaction bottle tested to 120 psi, max. working pressure of 60 psi). The hydrogen pressure was set to 35 psi with agitation, and the process went on for 19 h. The catalyst was removed by vacuum filtration and separated from the product by dissolving the white precipitate in 100 mL hot CH₂Cl₂. An additional batch of product was isolated by cooling the EtOH filtrate to 0° C. for 2 h. The clear solution was concentrated by rotary evaporation to yield a white solid. The solid was washed with MeOH to remove residual DCU. Yield: 22%. ¹H NMR (d⁶-DMSO, 400 MHz, 25° C.): δ 4.34 (d, J=6.0 Hz, 2H, —CH₂—), 4.63 (s, 2H, —CH₂—), 6.08 (t, J=7.2 Hz, 1H, Ar—H), 6.69 (d, J=7.2 Hz, 1H, Ar—H), 7.10 (d, J=6.4 Hz, 1H, Ar—H), 7.44 (m, 5H, Bz-H), 7.64 (m, 4H, Phenyl-H), 8.70 (t, J=5.6 Hz, 1H, —NH—), 9.02 (s, 1H, —OH). APCI-MS: m/z 334.9 [M+H]⁺. Anal. Calcd for C₂₀H₁₈N₂O₃: C, 71.84; H, 5.43; N, 8.38. Found: C, 71.49; H, 5.78; N, 8.52.

1-Hydroxy-6-[(4-Phenylbenzyl)carbamoyl]-2-pyridinone (20)

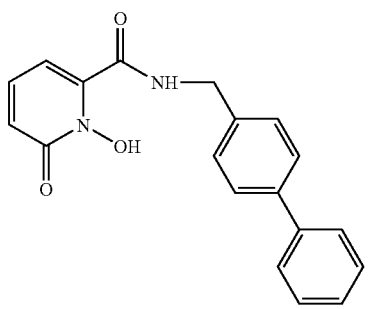

20

Synthesis of benzyl protected 1,2-HOPO acid (1,2-HOPOBn acid) (1-benzyloxy-6-carboxypyridin-2-one), from 6-hydroxypicolinic acid was performed as reported by Raymond et al. (*J. Med. Chem.*, 45, 3963 (2002)) (yield=80%). 1,2-HOPOBn acid (760 mg, 3.1 mmol) was added to 50 ml THF and dissolved immediately to a slightly yellow solution. NHS (360 mg, 3.1 mmol) was added to this solution (no color change) and stirred under N₂ for 30 mins. DCC (640 mg, 3.1 mmol) was then added to the flask (no color change) and stirred for 3 hrs under N₂. Solution was vacuum filtered to remove DCU and 4-phenylbenzylamine (568 mg, 3.1 mmol) was added to clear bronze filtrate. The solution stirred o/n at RT under N₂. The creamy yellow solution was rotovaped to dryness; the residue was dissolved in methylene chloride and washed with saturated sodium bicarbonate. The organic layer was dryed over magnesium sulfate and then rotovaped to dryness to an off-white residue. The residue was sonicated in a minimal amount of MeOH to remove any remaining DCU. The sonicate was rotovaped to dryness and oven dried for 3 hours to a white solid with a 71% yield. Deprotection of the benzyl group was carried out in a 1:1 mixture of HCl (40 ml) to glacial acetic acid (40 ml) for 5 days. The milky white solution was then rotovaped to dryness and washed 3 times with MeOH. The final white residue (20) was oven dried to a 91% yield.

¹H NMR (400 MHz) δ 4.45 (d, J=6 Hz, 2H), δ 6.33 (d, J=6.8 Hz, 1H), δ 6.56 (d, J=9.2 Hz, 1H), δ 7.32-7.46 (m, 9H), δ 7.63 (t, J=8 Hz, 1H), δ 9.42 (s, 1H) HR-EI-MS calcd for C₁₉H₁₆N₂O₃ 320.1155. Found 320.1158.

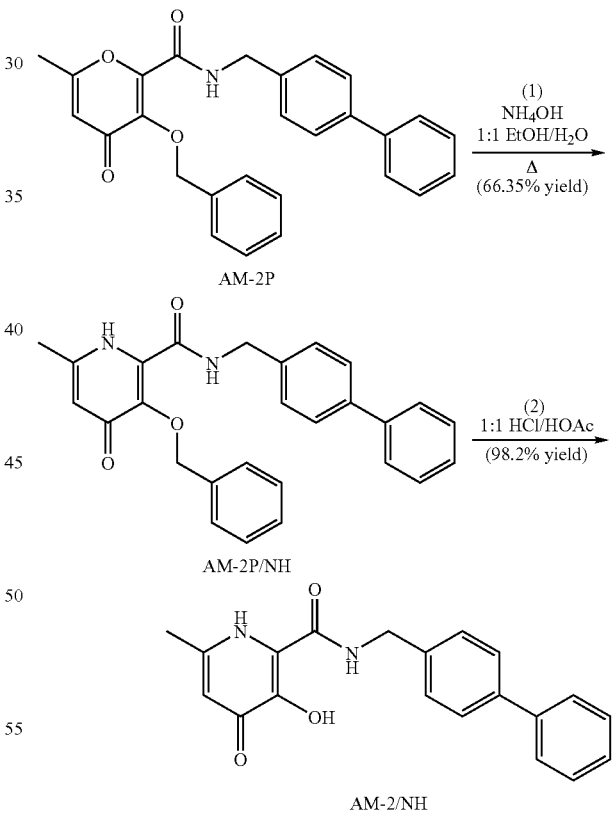

(1) 3-(Benzyloxy)-N-(biphenyl-4-ylmethyl)-6-methyl-4-oxo-1,4-dihydropyridine-2-carboxamide (AM-2P/NH). A 40-mL sealed tube was charged with 3-(benzyloxy)-N-(biphenyl-4-ylmethyl)-6-methyl-4-oxo-4H-pyran-2-carboxamide (AM-2P) (0.2535 g, 0.5958 mmol) and 35 mL of 1:1 (v/v) ethanol/water. Mixture was then cooled to 0° C. on an ice-bath. To the cold mixture was added 2.3 mL of 30% ammonium hydroxide. The tube was sealed, placed in an oil-bath, and heated to 80° C. for 4 days. The reaction was allowed to cool to room temperature and placed in the freezer over night, producing off-white solids which were collected and air-dried (0.167 g, 0.3953 mmol, 66.35%); $^1$H NMR (DMSO-$d_6$) δ: 2.22 (s, 3H, CH$_3$), 4.58 (d, 2H, CH$_2$), 5.31 (s, 2H, CH$_2$), 6.12, (s, 1H, CH) 7.25-7.65 (m, 14H, Ar), 9.03 (t, 1H, NH-amide), 11.20 (s, 1H, NH); HPLC-MS (ESI) m/z 424.94 [M+H]$^+$, >95% pure.

(2) N-(biphenyl-4-ylmethyl)-3-hydroxy-6-methyl-4-oxo-1,4-dihydropyridine-2-carboxamide (AM-2NH). A 100-mL round-bottomed flask was charged with AM-2P/NH (0.1107 g, 0.2608 mmol), 5.8 mL of 1:1 conc. HCl/acetic acid, and a stir bar. The mixture was stirred at room temperature for 4 days. Acids were removed on a rotary evaporator by co-evaporation with methanol to yield 0.086 g of AM-2NH (0.256 mmol, 98.2%). $^1$H NMR (DMSO-$d_6$) δ: 4.62 (d, 2H), 7.14 (s, 1H), 7.35 (t, 1H), 7.43-7.47 (m, 4H), 7.62-7.65 (m, 4H), 9.46 (t, 1H). HR-EI-MS: Found m/z 334.1315 (expected 334.1312).

Scheme 8. Route to PY-derivative amides through activated ester coupling.

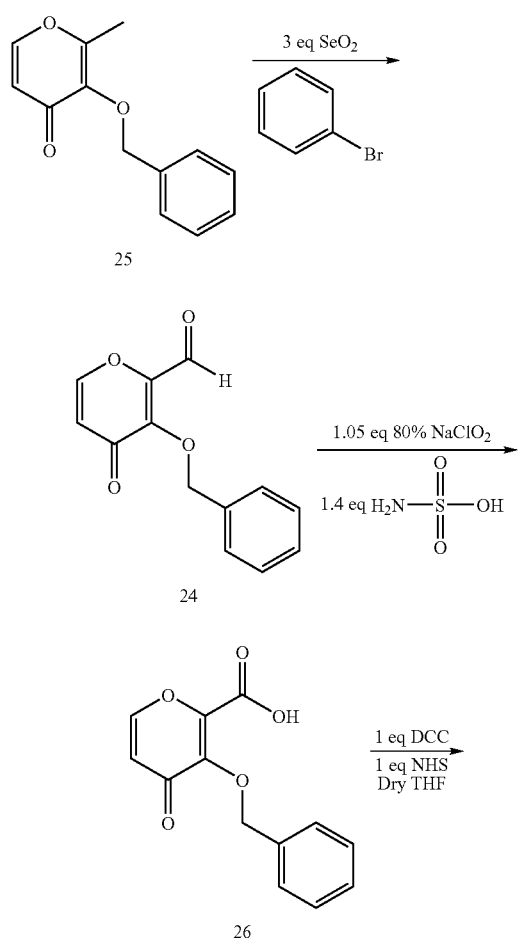

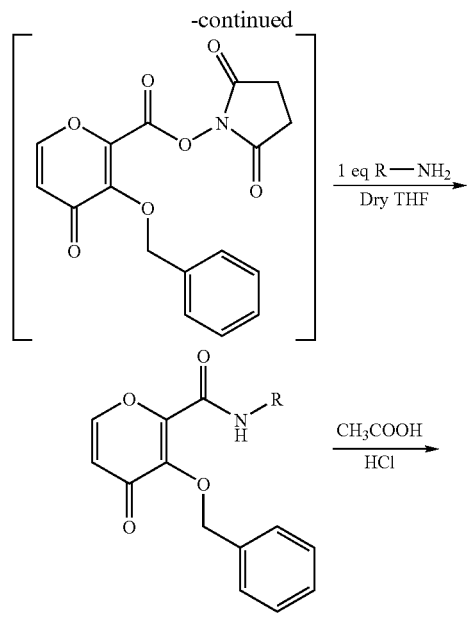

PY-3P (28) (R = 4-phenylphenethyl)
PY-5P (35) (R = (4-(4-cyanophenyl)benzyl)
PY-6P (39) (R = 4, 4-biphenylbenzyl)

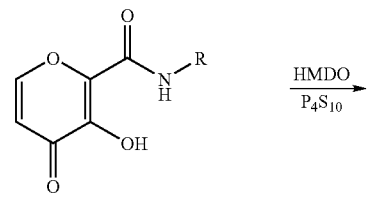

21 ( R= 4-phenylbenzyl)(PY-2)
29 (R = 4-phenylphenethyl) (PY-3)
36 (R = (4-(4-cyanophenyl)benzyl))(PY-5)
40 (R = 4, 4-biphenylbenzyl)(PY-6)

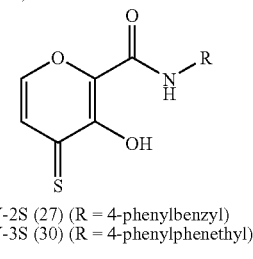

PY-2S (27) (R = 4-phenylbenzyl)
PY-3S (30) (R = 4-phenylphenethyl)

General. Unless otherwise noted, starting materials were obtained from commercial suppliers (Aldrich) and used without further purification. 3-Hydroxy-pyran-4(1H)-one-2-carboxy-N-(4-phenylbenzylamide) (PY-2, 21) was synthesized in a manner similar to that shown in Scheme 1 for AM2, but starting from compound 26 (see Scheme 8). The synthesis of 24 and 26 was based on a literature procedure. See, P. Pace et al., *Bioorg. Med. Chem. Lett.*, 14, 3257 (2004).

3-Hydroxy-4-thiopyrone-2-carboxy-N-(4-phenylbenzylamide) (PY-2S, 27). 21 (PY-2, 134 mg, 0.42 mmol) was suspended in chloroform (60 mL) and dissolved upon heating to ~60° C. HMDO (225 mg, 1.4 mmol, 3.3 equiv) and P$_4$S$_{10}$ (67 mg, 0.15 mmol, 0.36 equiv) were added to the stirring solution. The reaction flask was fitted with a condenser, and heated to reflux (~70° C.) under a dinitrogen atmosphere for 7.75 h. After heating, a dark brown solid was removed by vacuum filtration, and the filtrate was concentrated to give a brown residue. The residue was recrystallized from a 1:2 mixture of benzene:CHCl$_3$ by slow evaporation. $^1$H NMR (CDCl$_3$, 400 MHz, 25° C.): δ 4.71 (d, J=5.2 Hz, 2H, —CH$_2$—), 7.35 (m, 6H), 7.57 (t, J=6.4 Hz, 4H), 7.73 (d, J=5.2 Hz, 1H, Ar—H), 7.91 (s, br, 1H, amide-H), 9.69 (s, br, 1H, —OH). APCI-MS (+): m/z 337.89 [M+H]$^+$. HR-EI-MS Calcd for C$_{19}$H$_{15}$O$_3$NS [M]: 337.0767. Found, A: 337.0772, 0.4 ppm.

3-Benzyloxy-pyran-4(1H)-one-2-carboxy-N-[2-(4-biphenyl)ethylamide)] (PY-3P, 28). To a suspension of 26 (666 mg, 2.7 mmol) in dry THF (25 mL) was added NHS (311 mg, 2.7 mmol, 1 equiv), and the mixture was stirred at room temperature under a dinitrogen atmosphere for 30 min. DCC (558 mg, 2.7 mmol, 1 equiv) was then added, and the reaction was stirred at room temperature under a dinitrogen atmosphere for 3 h. The DCU was removed by vacuum filtration, and to the resulting filtrate was added 2-(4-biphenyl)ethylamine (533 mg, 2.7 mmol, 1 equiv) as a solid. A precipitate formed immediately after the addition of the amine. The reaction was stirred at room temperature overnight under a dinitrogen atmosphere. The solvent was removed by rotary evaporation to yield an off-white solid. The solid was taken up in CHCl$_3$ (25 mL) and washed with 2×50 mL saturated sodium bicarbonate solution. The CHCl$_3$ layer was dried over magnesium sulfate and concentrated by rotary evaporation to an off-white residue. This residue was taken up in CHCl$_3$ and purified by silica flash chromatography. The product eluted with CHCl$_3$. The white product was dried on a Schlenk line with a vacuum pump for 3.5 h. Yield: 55%. $^1$H NMR (CDCl$_3$, 400 MHz, 25° C.): δ 2.71 (t, J=7.0 Hz, 2H, ethyl-CH$_2$—), 3.53 (q, J=6.5 Hz, 2H, ethyl-CH$_2$—), 5.28 (s, 2H, benzyl-CH$_2$—), 6.45 (d, J=6.0 Hz, 1H, Ar—H), 7.20 (m, 5H), 7.33 (m, 5H), 7.41 (t, J=7.8 Hz, 1H), 7.53 (t, J=7.2 Hz, 4H), 7.81 (d, J=5.6 Hz, 1H, Ar—H). $^{13}$C NMR (CDCl$_3$, 100 MHz, 25° C.): δ 34.7, 41.0, 75.2, 117.4, 126.8, 127.1, 127.3, 128.6, 128.7, 128.9, 129.0, 129.1, 135.0, 137.3, 139.5, 140.5, 146.8, 146.9, 154.3, 158.6, 175.5. ESI-MS (+): m/z 448.05 [M+Na]$^+$.

3-Hydroxy-pyran-4(1H)-one-2-carboxy-N-[2-(4-biphenyl)ethylamide)] (PY-3, 29). 28 (565 mg, 1.3 mmol) was dissolved in 30.7 mL of a 1:1 solution of concentrated HCl and glacial acetic acid. The solution was stirred at room temperature under a dinitrogen atmosphere for 24 h. The reaction was co-evaporated with methanol (3×30 mL) to yield an off-white solid. $^1$H NMR (CDCl$_3$, 400 MHz, 25° C.): δ 2.97 (t, J=7.0 Hz, 2H, ethyl-CH$_2$—), 3.76 (q, J=6.5 Hz, 2H, ethyl-CH$_2$—), 6.45 (d, J=6.0 Hz, 1H, Ar—H), 6.81 (s, br, amide-H), 7.32 (m, 4H), 7.43 (t, J=7.6 Hz, 1H), 7.56 (m, 4H), 7.67 (d, J=6.0 Hz, 1H, Ar—H). $^{13}$C NMR (CDCl$_3$, 100 MHz, 25° C.): δ 35.1, 40.1, 115.3, 126.8, 127.2, 127.4, 128.7, 129.0, 135.9, 136.8, 139.6, 140.4, 152.9. ESI-MS (+): m/z 358.06 [M+Na]$^+$.

3-Hydroxy-4-thiopyrone-2-carboxy-N-[2-(4-biphenyl)ethylamide)] (PY-3S, 30). 29 (390 mg, 1.2 mmol) was suspended in benzene (120 mL) and dissolved upon heating to ~65° C. HMDO (627 mg, 3.9 mmol, 3.3 equiv) and P$_4$S$_{10}$ (186 mg, 0.4 mmol, 0.36 equiv) were added to the stirring solution. The reaction flask was fitted with a condenser, and heated to reflux (~90° C.) under a dinitrogen atmosphere for 2 h. After heating, a small amount of yellow solid was removed by vacuum filtration, and the filtrate was concentrated to give an orange residue. The residue was purified by silica flash chromatography.

The column was prepared so as to remove excess metal ions from the silica before loading of the reaction mixture. 3-Hydroxy-2-methyl-4-pyrone (maltol, ~50 mg) was dissolved in 5% MeOH in CHCl$_3$ (~100 mL) and flushed through the packed silica column. Rinsing with the maltol solution was continued until no red color was observed as a mobile band moving through the silica. Upon disappearance of any red color from the column, two more column volumes of the maltol solution were added to ensure complete demetallation of the silica. Finally, the column was flushed with 2×200 mL of 1% MeOH in CHCl$_3$ to remove any remaining maltol.

The residue from the reaction mixture was then loaded onto the conditioned column and eluted with 1% MeOH in CHCl$_3$ to obtain the desired product as a bright yellow band. After removal of solvent on a rotary evaporator, crude product was obtained as an orange solid. The product was then recrystallized from hot benzene. Yield: 83%. $^1$H NMR (CDCl$_3$, 400 MHz, 25° C.): δ 2.97 (t, J=7.0 Hz, 2H, ethyl-CH$_2$—), 3.78 (q, J=6.7 Hz, 2H, ethyl-CH$_2$—), 6.70 (s, br, 1H, amide-H), 7.31 (m, 3H), 7.42 (m, 3H), 7.56 (t, J=7.8 Hz, 4H), 7.69 (d, J=4.8 Hz, 1H, Ar—H). APCI-MS (+): m/z 352.04 [M+H]$^+$. HR-FAB-MS Calcd for C$_{20}$H$_{18}$O$_3$NS [M+H]: 352.1002. Found, A: 352.1000, −0.5 ppm.

3-Benzyloxy-pyran-4(1H)-one-2-carboxy-N-(4,4-cyanophenylbenzylamide) (PY-5P, 35). To a suspension of 26 (123 mg, 0.5 mmol) in dry THF (20 mL) was added NHS (58 mg, 0.5 mmol, 1 equiv), and the mixture was stirred at room temperature under a dinitrogen atmosphere for 30 min. DCC (103 mg, 0.5 mmol, 1 equiv) was then added, and the reaction was stirred at room temperature under a dinitrogen atmosphere for 3 h. The DCU was removed by vacuum filtration, and to the resulting filtrate was added 4-cyanophenylbenzylamine (104 mg, 0.5 mmol, 1 equiv) as a solid. The reaction was stirred at room temperature overnight under a dinitrogen atmosphere. The solvent was removed by rotary evaporation to yield a pale yellow solid. The solid was taken up in CHCl$_3$ (20 mL) and washed with 3×25 mL saturated sodium bicarbonate solution. The CHCl$_3$ layer was dried over magnesium sulfate, filtered, and concentrated by rotary evaporation to a yellow solid. The product was purified by silica column chromatography (CHCl$_3$ with 0-1% MeOH) to yield a white solid. The solid was titurated with hexanes. The white product was dried in a vacuum oven with heat for 1.5 h. Yield: 56%. $^1$H NMR (CDCl$_3$, 400 MHz, 25° C.): δ 4.48 (d, J=5.6 Hz, 2H, ethyl-CH$_2$—), 5.37 (s, 2H, benzyl-CH$_2$—), 6.51 (d, J=5.6 Hz, 1H, Ar—H), 7.27 (m, 7H), 7.53 (d, J=8.0 Hz, 2H), 7.68 (d, J=8.4 Hz, 2H), 7.75 (d, J=8.4 Hz, 2H), 7.86 (d, J=5.6 Hz, 1H, Ar—H), 8.16 (s, br, 1H, amide-H). ESI-MS (+): m/z 458.98 [M+Na]$^+$, m/z 436.89 [M+H]$^+$.

3-Hydroxy-pyran-4(1H)-one-2-carboxy-N-(4,4-cyanophenylbenzylamide) (PY-5, 36). 35 (132 mg, 0.30 mmol) was dissolved in 15 mL of a 1:1 solution of concentrated HCl and glacial acetic acid. The solution was stirred at room temperature under a dinitrogen atmosphere for 4.5 days. The reaction was concentrated by rotary evaporation followed by co-evaporation with methanol (3×10 mL) to yield a pale pink solid. Yield: 60%. $^1$H NMR (CDCl$_3$, 400 MHz, 25° C.): δ 4.69 (d, J=5.6 Hz, 2H, ethyl-CH$_2$—), 6.48 (d, J=5.6 Hz, 1H, Ar—H), 7.18 (s, br, 2H), 7.46 (d, J=8.0 Hz, 2H), 7.59 (d, J=7.6 Hz, 2H), 7.66 (d, J=8.0 Hz, 2H), 7.73 (d, J=7.2 Hz, 1H, Ar—H). APCI-MS (+): m/z 346.89 [M+H]$^+$.

3-Benzyloxy-pyran-4(1H)-one-2-carboxy-N-(4,4-biphenylbenzylamide) (PY-6P, 39). To a suspension of 26 (103 mg, 0.42 mmol) in dry THF (20 mL) was added NHS (48 mg, 0.42 mmol, 1 equiv), and the mixture was stirred at room temperature under a dinitrogen atmosphere for 30 min. DCC (86 mg, 0.42 mmol, 1 equiv) was then added, and the reaction was stirred at room temperature under a dinitrogen atmosphere for 3 h. The DCU was removed by vacuum filtration, and to the resulting filtrate was added 4-biphenylbenzylamine (108 mg, 0.42 mmol, 1 equiv) as a solid. The reaction was stirred at room temperature overnight under a dinitrogen atmosphere. The solvent was removed by rotary evaporation to yield yellow oil. The oil was taken up in $CHCl_3$ (20 mL) and washed with 3×25 mL saturated sodium bicarbonate solution. The $CHCl_3$ layer was dried over magnesium sulfate, filtered, and concentrated by rotary evaporation to a yellow solid. The product was purified by silica column chromatography ($CHCl_3$ with 0-1% MeOH) to yield a white solid. The solid was titurated with EtOH. The off-white product was dried in a vacuum oven with heat for 1.5 h. Yield: 78%. $^1$H NMR ($d^6$-DMSO, 500 MHz, 25° C.): δ 4.49 (d, J=5.5 Hz, 2H, ethyl-$CH_2$—), 5.37 (s, 2H, benzyl-$CH_2$—), 6.51 (d, J=6.0 Hz, 1H, Ar—H), 7.23 (m, 3H), 7.29 (m, 1H), 7.37 (m, 1H), 7.47 (t, J=8.0 Hz, 2H), 7.59 (d, J=8.0 Hz, 2H), 7.68 (m, 6H), 7.86 (d, J=5.0 Hz, 1H, Ar—H), 8.14 (s, br, 1H, amide-H).

3-Hydroxy-pyran-4(1H)-one-2-carboxy-N-(4,4-biphenyl-benzylamide) (PY-6, 40). 39 (100 mg, 0.21 mmol) was dissolved in 10 mL of a 1:1 solution of concentrated HCl and glacial acetic acid. The solution was stirred at room temperature under a dinitrogen atmosphere for 6 days. The reaction was concentrated by rotary evaporation followed by co-evaporation with methanol (3×10 mL) to yield a pale pink solid. Yield: 77%. $^1$H NMR ($d^6$-DMSO, 400 MHz, 25° C.): δ 4.54 (d, J=5.6 Hz, 2H, ethyl-$CH_2$—), 6.47 (d, J=5.2 Hz, 1H, Ar—H), 7.37 (m, 1H), 7.44 (m, 4H), 7.70 (t, J=7.2 Hz, 4H), 7.75 (s, 4H), 8.18 (d, J=5.6 Hz, 1H, Ar—H), 8.14 (t, J=5.8 Hz, 1H, amide-H). APCI-MS (−): m/z 396.08 [M−H]$^−$.

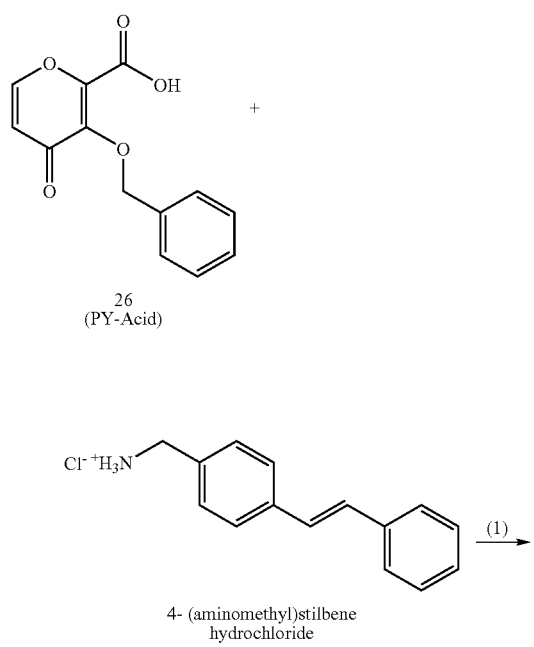

Scheme 9

26
(PY-Acid)

4-(aminomethyl)stilbene hydrochloride

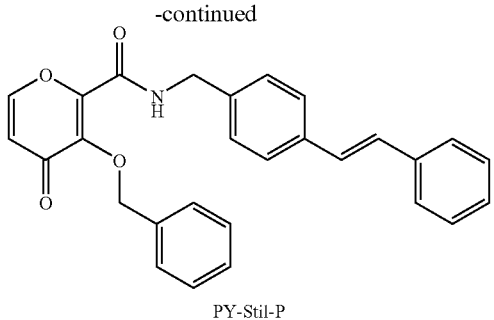

PY-Stil-P

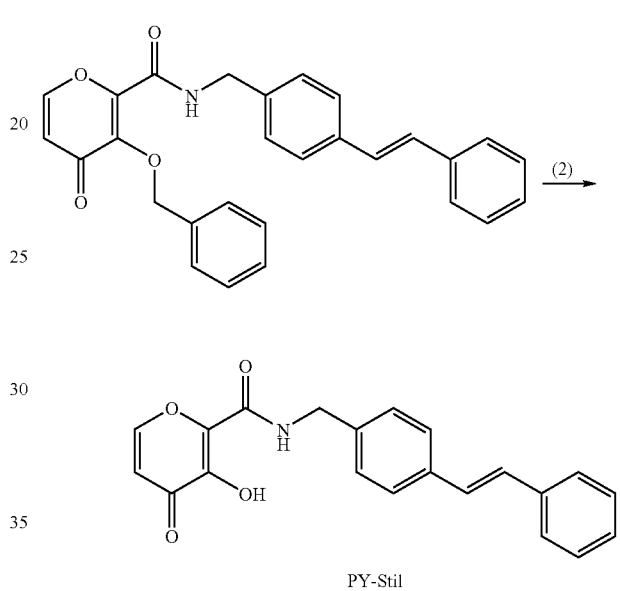

PY-Stil 4-(Aminomethyl)stilbene hydrochloride was prepared by reduction of 4-cyanostilbene with lithium aluminum hydride in ether according to the procedure of C. T. Cavalito et al., J. Med. Chem., 14, 130 (1971).

(1) (E)-3-(benzyloxy)-4-oxo-N-(4-styrylbenzyl)-4H-pyran-2-carboxamide (PY-Stil-P). 3-(Benzyloxy)-4-oxo-4H-pyran-2-carboxylic acid (26, PY-Acid) (0.4918 g, 1.997 mmol) was dissolved in 111 mL of dry THF under $N_2$. N-hydroxysuccinamide (NHS) (0.2301 g, 1.999 mmol) was added, and the mixture was stirred under $N_2$ for 30 min. DCC (0.4136 g, 2.000 mmol) was added, and the mixture stirred under $N_2$ for 3 hours, after which the resulting DCU was filtered off and washed with 2 mL of THF. The filtrate was added to a solution of 4-(aminomethyl)stilbene hydrochloride (0.4994 g, 2.032 mmol) and 1.12 mL (7.98 mmol) of triethylamine in 111 mL of warm THF, and the mixture was slowly refluxed (oil bath temperature: 79° C.) for 67 hours. Solvent was removed on a rotary evaporator. The tan residue was taken up in 15 mL of chloroform and washed with saturated $NaHCO_3$ (3×10 mL). Organic phase was dried over $MgSO_4$ and rotovapped to a tan powder. Recrystallization of the residue from methanol gave the product as a light tan solid in 34.72% yield (0.3033 g, 0.6933 mmol). $^1$H-NMR (DMSO-$d_6$) δ: 4.42 (d, 2H), 5.17 (s, 2H), 6.54

(d, 1H), 7.24-7.40 (m, 12H), 7.53 (d, 2H), 7.61 (d, 2H), 8.22 (d, 1H), 9.15 (t, 1H). HR-EI-MS: Found m/z=437.1623 (437.1622).

(2) (E)-3-hydroxy-4-oxo-N-(4-styrylbenzyl)-4H-pyran-2-carboxamide (PY-Stil). PY-Stil-P (0.1500 g, 0.3429 mmol) was stirred in 7.6 mL of 1:1 conc. HCl/acetic acid at room temperature, under $N_2$, for 45 hours. Acids were removed by co-evaporation with methanol. A brown contaminant was removed by sonicating the residue in methanol and collecting the faintly pink powder, which was then dried at 60° C., in vacuo to yield 0.0812 g of PY-Stil (0.234 mmol, 68.2%). $^1$H-NMR (DMSO-$d_6$) δ: 4.49 (d, 2H), 6.47 (d, 1H), 7.24-7.28 (m, 3H), 7.33-7.39 (m, 4H), 7.57-7.60 (m, 4H), 8.18, (d, 1H), 9.33 (t, 1H), 11.39 (s, br, 1H). $^{13}$C-NMR (DMSO-$d_6$) δ: 42.2, 114.6, 126.4, 126.5, 127.8, 128.0, 128.2, 128.7, 135.9, 137.0, 137.2, 137.8, 148.5, 154.9, 162.4, 173.3. (Note: $^{13}$C-NMR was too noisy to integrate.) HR-EI-MS: Found m/z=347.1158 (347.1152). LC-ESI(pos)-MS shows ~96% purity.

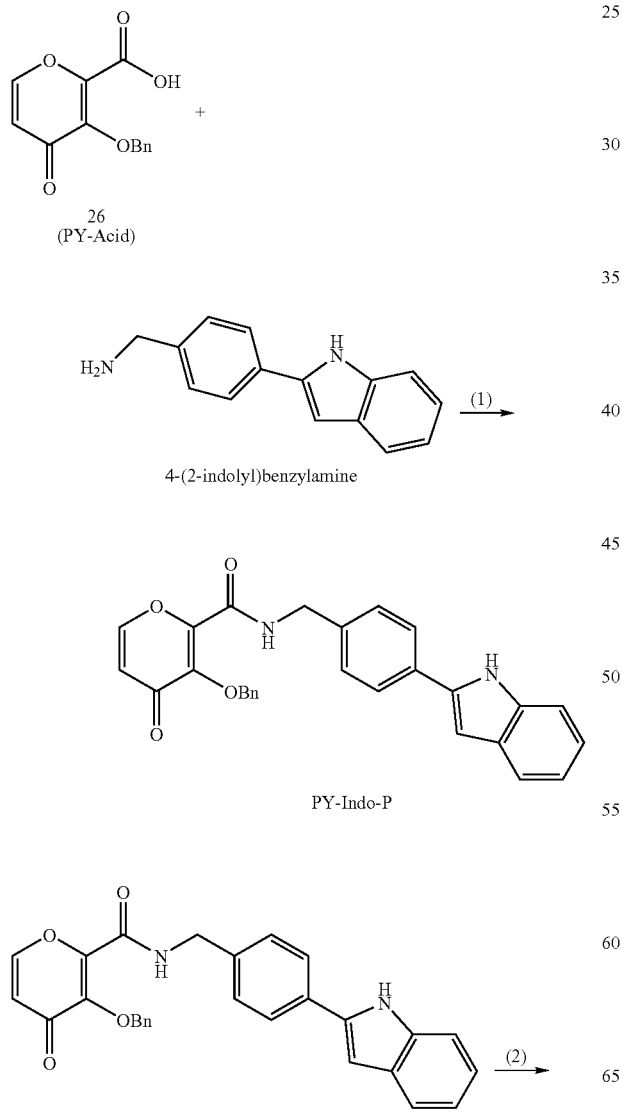

Scheme 10

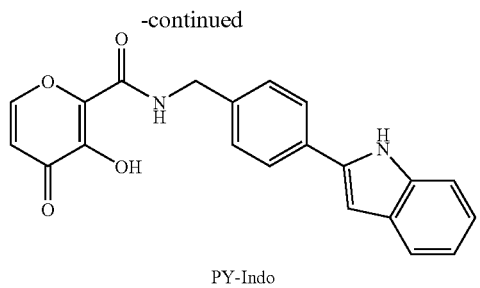

PY-Indo 4-(2-Indolyl)benzylamine was prepared by the procedure of P. J. Palmer et al., *J. Med. Chem.*, 14, 1226 (1971).

(1) N-(4-(1H-indol-2-yl)benzyl)-3-(benzyloxy)-4-oxo-4H-pyran-2-carboxamide (PY-Indo-P): 3-(Benzyloxy)-4-oxo-4H-pyran-2-carboxylic acid (26, PY-Acid) (0.4919 g, 1.998 mmol) was dissolved in 11 mL of dry THF under $N_2$. N-hydroxysuccinamide (NHS) (0.2303 g, 2.001 mmol) was added, and the mixture was stirred under $N_2$ for 30 min. DCC (0.4150 g, 2.006 mmol) was added, and the mixture stirred under $N_2$ for 3 hours, after which the resulting DCU was filtered off and washed with 3 mL of THF. The filtrate was added to a solution of 4-(2-indolyl)benzylamine (0.3998 g, 1.799 mmol) in 111 mL of warm THF, and the mixture was slowly refluxed (oil bath temperature: 79° C.) for 40 hours. Solvent was removed on a rotovapor. The amber oil was taken up in 50 mL of dichloromethane (DCM) and washed with saturated $NaHCO_3$ (3×15 mL). Organic phase was dried over $MgSO_4$ and rotovapped to a yellow powder. Powder was taken up in DCM, a few mg of silica gel was added, and the mixture was rotovapped to a friable powder. Powder was chromatographed on silica gel (DCM, 0-5% methanol). The yellow-orange fraction was evaporated to a yellow powder, then dried in vacuo at 50° C. to give 0.4784 of PY-Indo-P (1.062 mmol, 59.03%). $^1$H-NMR (Acet-$d_6$) δ: 4.55 (d, 2H), 5.34 (s, 2H), 6.46 (d, 1H), 6.91 (s, 1H), 7.02 (t, 1H), 7.10 (t, 1H), 7.29 (t, 3H), 7.36-7.41 (m, 5H), 7.56 (d, 1H), 7.83 (d, 2H), 8.05 (d, 2H), 8.43 (t, 1H), 10.68 (s, 1H). ESI(pos)-MS: Found [M+H]$^+$=451.03. LC-ESI(pos)-MS shows ~90% purity.

(2) N-(4-(1H-indol-2-yl)benzyl)-3-hydroxy-4-oxo-4H-pyran-2-carboxamide (PY-Indo): PY-Indo-P (0.3587 g, 0.7963 mmol) was stirred in 18 mL of 1:1 conc. HCl/acetic acid at room temperature, under $N_2$, for 23 hours. Acids were removed by co-evaporation with methanol to give a black residue. Material was sonicated in 10 mL of 1:1 $NH_4OH$, then neutralized (pH=7-8) with 80% acetic acid. After standing for 1 hour, the solids were collected and air-dried. Material was then boiled in methanol, cooled to room temperature and filtered. Evaporation of filtrate and drying in vacuo (60° C.) gave PY-Indo as a yellow powder (0.115 g, 0.319 mmol, 40.1%). $^1$H-NMR (DMSO-$d_6$) δ: 4.51 (d, 2H), 6.38 (d, 1H), 6.87 (s, 1H), 6.98 (t, 1H), 7.08 (t, 1H), 7.39 (m, 3H), 7.52 (d, 1H), 7.82 (d, 2H), 8.10 (d, 1H), 9.82 (t, 1H), 11.51 (s, 1H).

Structures of representative MMP inhibitors prepared in accord with the present examples are summarized in Table 3.

TABLE 3
Structure of MMP Inhibitors
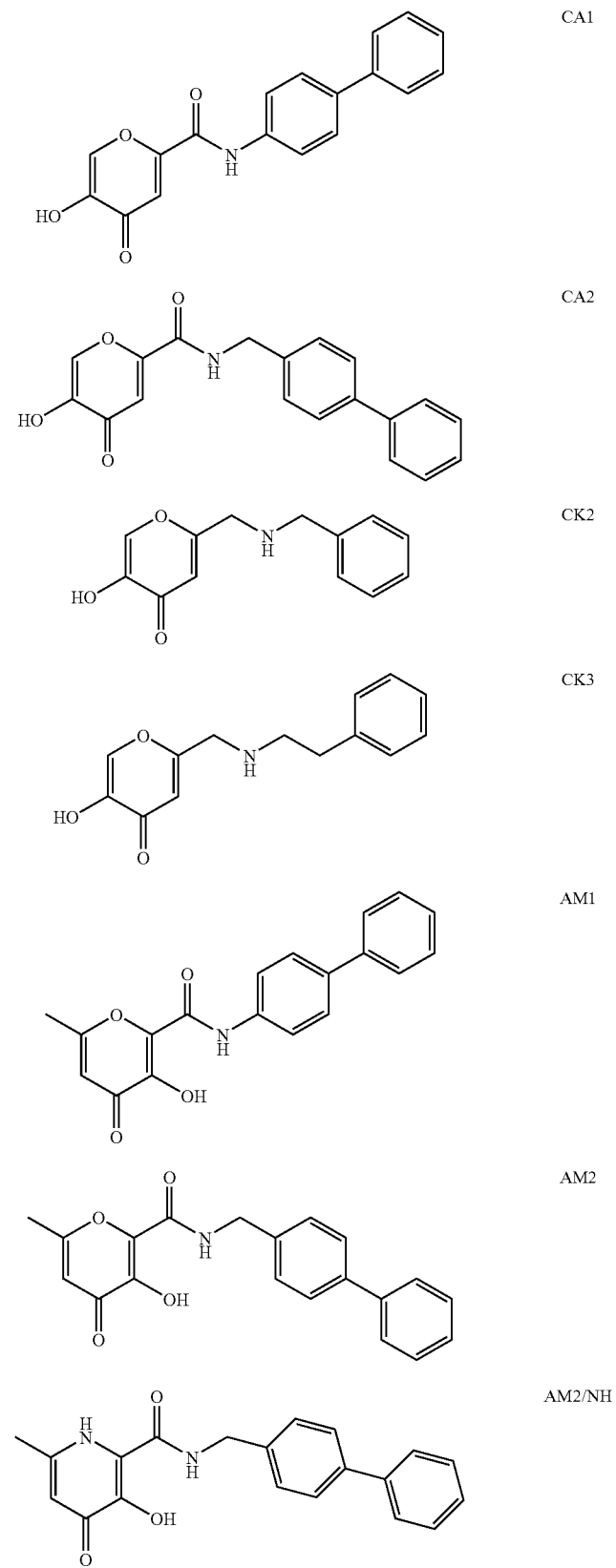

TABLE 3-continued
Structure of MMP Inhibitors
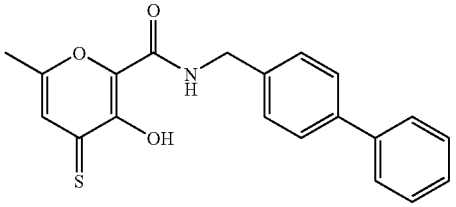
AM-2S
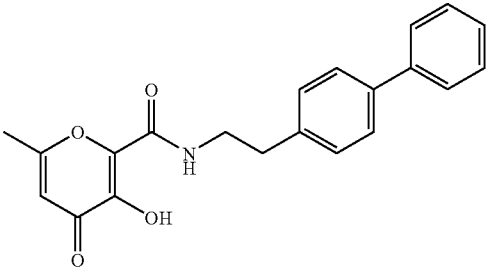
AM3
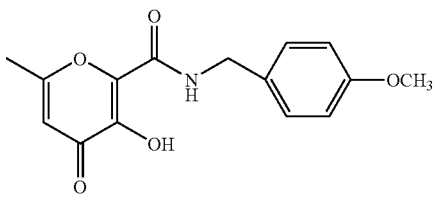
AM4
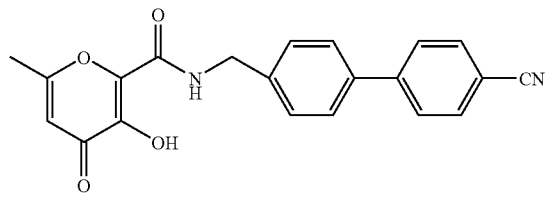
AM5
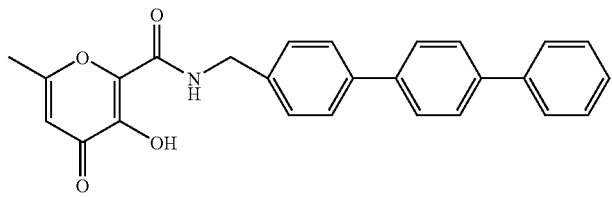
AM6
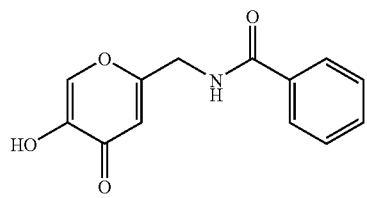
KA1
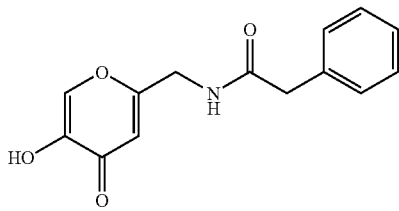
KA2

TABLE 3-continued
Structure of MMP Inhibitors
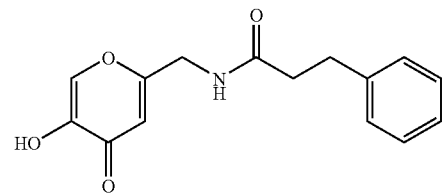
KA3
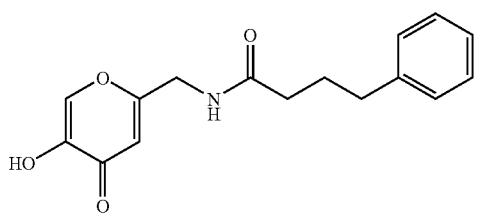
KA4
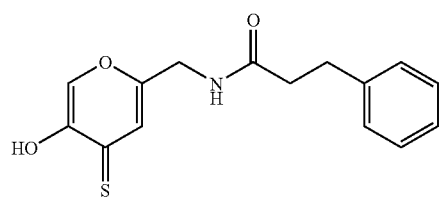
TKA3
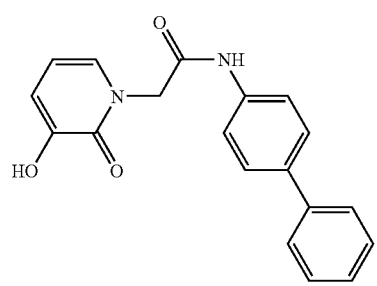
HP32A
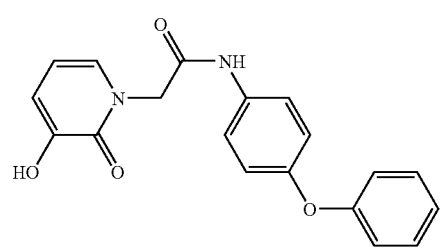
HP32B
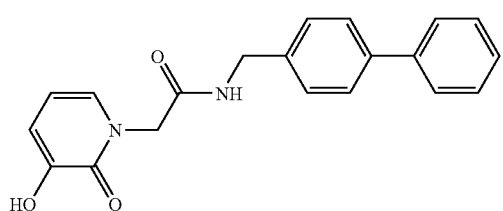
HP32C TABLE 3-continued
Structure of MMP Inhibitors
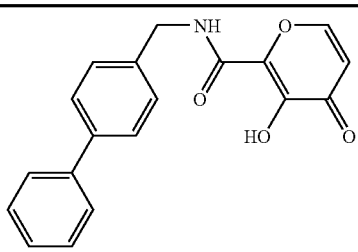
21 PY-2
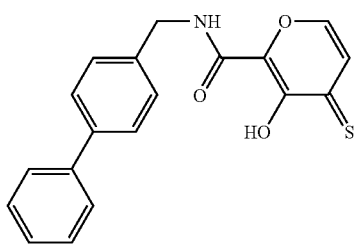
27 PY-2S
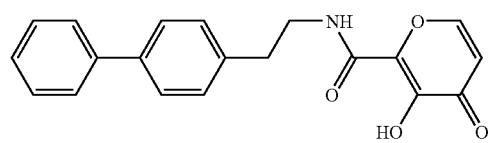
29 PY-3
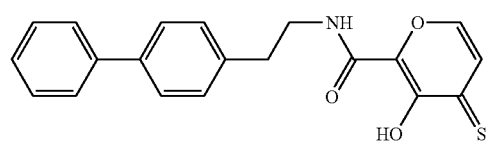
30 PY-3S
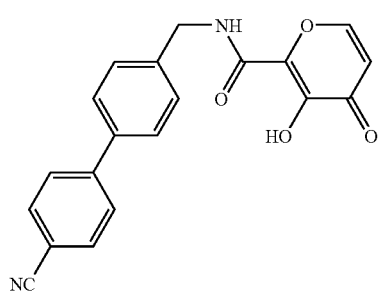
36 PY-5

TABLE 3-continued

Structure of MMP Inhibitors

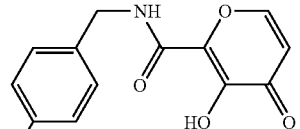

PY-6

40

Figure 8:
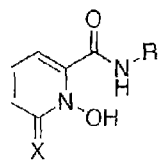
FIG. 8. Depicts additional embodiments of the invention.
Figure 8:
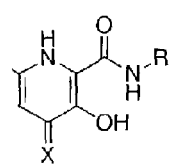
Figure 8:
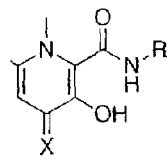
Figure 8:
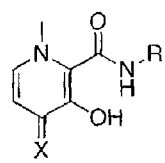
Figure 8:
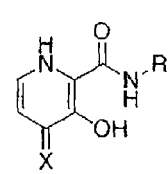
Figure 8:
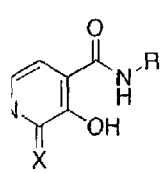
Figure 8:
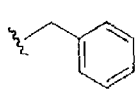
Figure 8:
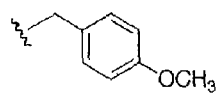
Figure 8:
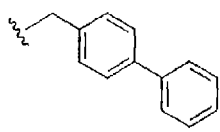
Figure 8:
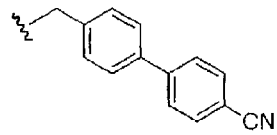
Figure 8:
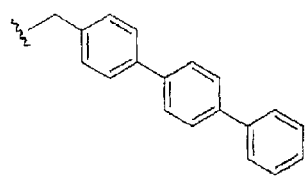
Figure 8:
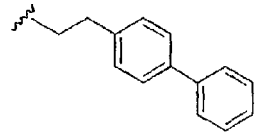
Figure 8:
Figure 8:
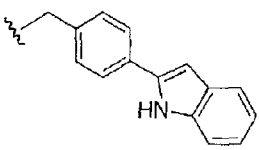
Figure 8:
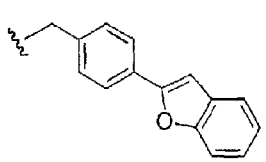

Additional structures of compounds of the invention are depicted in FIG. 8.

Computer Modeling Analysis. Computer modeling was utilized to facilitate the design of the full-length MMPi described above. This was performed as per a published procedure[26] and further augmented with the use of LUDI (Accelyrs, Inc.).

Oxygen-Containing MPIs. Since MMPs were first linked to diseases such as inflammatory conditions such as arthritis and cancer, hydroxamate-derived drugs have been the staple for MMPi design.[1] There has been much effort placed to improve the design of better peptidomimetic "backbones" of MMP inhibitors, with the effort focused on enhancing the ZBG being relatively miniscule in comparison. Furthermore, many HDACi and LFi compounds are also based on the hydroxamate ZBG.

New chelators were selected that were expected to bind as well as or better than hydroxamates. Hydroxypyridinones (HOPOs) were selected as lead compounds for several reasons. HOPOs are known to be strong metal chelators.[27,28] In addition, the cyclic structure of hydroxypyridinones reduces the degrees of freedom in the ligand, preventing the cis to trans isomerization that can occur in hydroxamic acids, which ultimately detracts from the thermodynamic affinity of the metal-ligand interaction. The basicity of hydroxypyridinones varies between isomers, which potentially allows for tuning the protonation state of the ligand to accommodate possible hydrogen-bonding interactions in the protein active site.[29] Finally, many hydroxypyridinones and related compounds have been or are used in medical and food industry applications,[30] suggesting a reasonable level of biological tolerance for these chemical moieties. Several hydroxypyridinone and hydroxypyrone derivatives were also developed, including N-methylated hydroxypyridinones, a hydroxypyridinethione, and 3-hydroxy-2-methyl-4-pyrone (see above and also see FIG. 1).

Sulfur-Containing MPIs. Sulfur-containing ligands may be very good ZBGs because of the apparent thiophilicity of zinc(II).[31,32] Similarly, other thiol-based MPIs have been studied and have shown reasonably good activity when compared to hydroxamate-based inhibitors.[1,16,33,34] Combining the best features of both hydroxamates and thiol inhibitors into a single ZBG, sulfur-containing ZBGs were developed because of the higher affinity of sulfur for the $Zn^{2+}$ ion compared to oxygen. Furthermore, ZBGs with rigid ring structures that lock the O,S-donor atoms in a cis conformation, can bind $Zn^{2+}$ ion in a bidentate fashion, to minimize oxidation and disulfide bond formation, which can be problems for thiol MPI, in biological systems. FIG. 1 discloses the sulfur-containing molecules which were evaluated as ZBGs for MPI.

Figure 3:
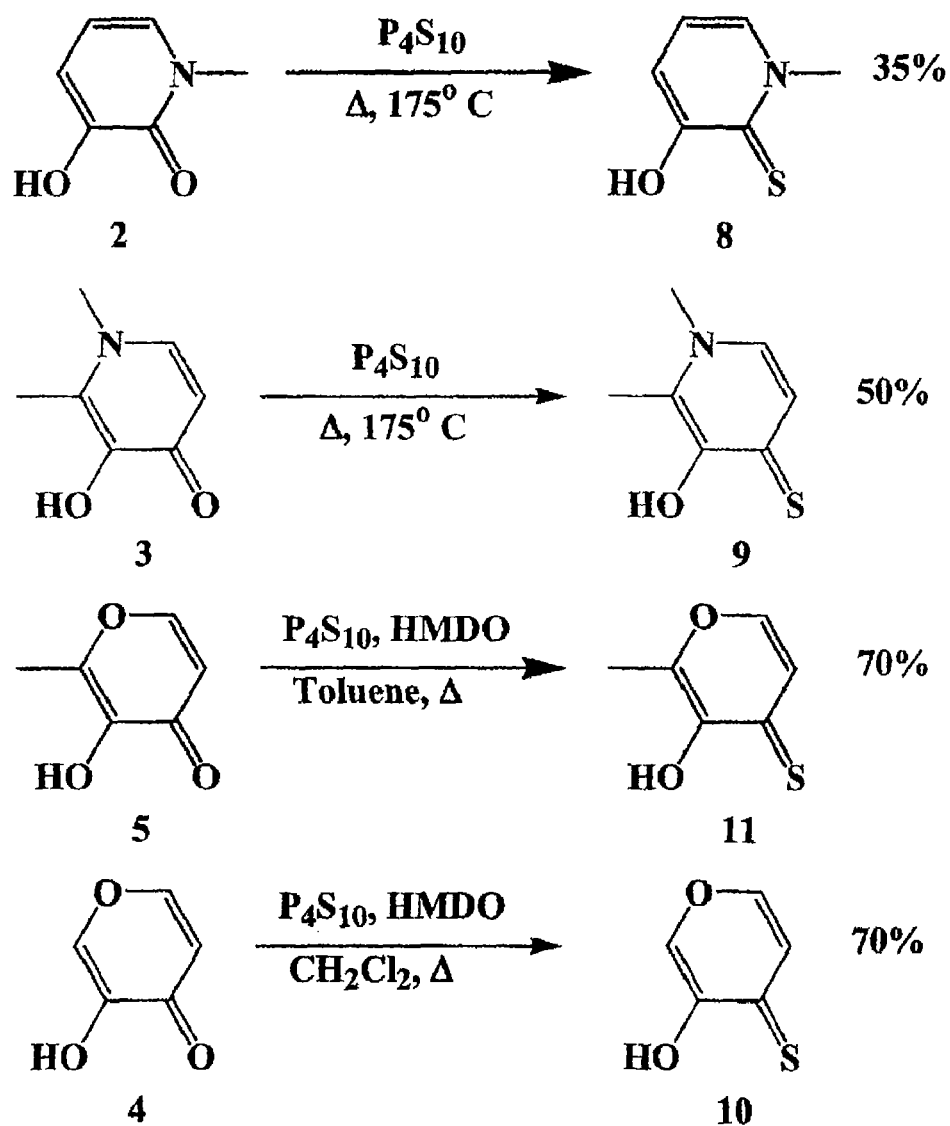
FIG. 3. Syntheses of representative O, S novel ZBGs. From top to bottom, synthesis of Me3,2-HOPTO (8) from Me3,2-HOPO (2), 3,4-HOPTO (9) from commercially available 3,4-HOPO (3), thiopyromeconic acid (10) from pyromeconic acid (4), and thiomaltol (11) from commercially available maltol (5).

Various thionation routes were explored to optimize reaction conditions. Facile, high-yielding reactions for novel sulfur-containing ligands have been developed (FIG. 3).[35,36] As demonstrated above for oxygen-containing ZBGs, the sulfur-containing ZBGs 11, 8, and 9 bind the $Zn^{2+}$ metal center in $(Tp^{Ph,Me})Zn$ in a bidentate fashion similar to acetohydroxamic acid, which makes them especially promising ZBGs.

MMP Assays with ZBGs of the Present Invention. Biological assays were used to test the potency of the ZBGs with respect to binding the MMP enzyme.[37] The assay plate was incubated with buffer, various concentrations of ZBG, and enzyme MMP-3 at 37° C. for 1 h. Increasing fluorescence was measured over time at 37° C.

As shown on the Table on FIG. 4, all of the ZBGs tested in the biological assay were more potent than acetohydroxamic acid (AHA). The O,S mixed donor ligands (7-11) were all about two orders of magnitude more potent than AHA. The raw data from the assays (FIG. 5) were converted to percentages of the control activity (FIG. 6) by comparing the slopes of the data sets to the control slope. Control activity was determined from wells with enzyme, buffer, and substrate. The amount of fluorescence over time correlated with MMP-3 enzymatic activity, wherein, more fluorescence over shorter time periods indicated a less potent ZBG. The $IC_{50}$ values were determined by a linear fit as per the assay kit instructions (Biomol, Inc.). In order to confirm the values obtained fluorescence-based assays, additional experiments were performed on some ZBGs using a widely-used colorimetric-based assay.[38] The $IC_{50}$ values from the colorimetric assays (FIG. 4) are in good agreement with those obtained by fluorescence measurements.

Based on the promising results obtained for the compounds in FIG. 1, the $IC_{50}$ value for inhibitors comprising at least one organic substituent were measured.

Activities of E. coli recombinant human MMP-1 catalytic domain (amino acids 81-249, 19.9 kDa), MMP-2 catalytic domain (amino acids 81-423, 40 kDa), and MMP-3 catalytic domain (amino acids 83-255, 19.5 kDa) were measured utilizing a 96-well microplate fluorescent assay kit purchased from BIOMOL International, following the procedure provided with the kit. Experiments were performed using a Bio-Tek Flx 800 fluorescence plate reader and Nunc white 96-well plates. The inhibitors were dissolved in DMSO and further diluted 500-fold in assay buffer: 50 mM HEPES, 10 mM $CaCl_2$, 0.05% Brij-35, pH 7.5 (MMP-1 and MMP-2) and 50 mM MES, 10 mM $CaCl_2$, 0.05% Brij-35, pH 6.0 (MMP-3). MMP-1, MMP-2 and MMP-3 were incubated individually with varying concentrations of different inhibitors for 1 h at 37° C., followed by addition of substrate to initiate the assay. Reactions were agitated by shaking for 1 sec after each fluorescence measurement. Upon cleavage of the fluorescent substrate, Mca-Pro-Leu-Gly-Leu-Dpa-Ala-Arg-$NH_2$ (0.4 mM in assay; Mca=7-methoxycoumarin-4-yl)-acetyl; Dpa=N-3-(2, 4-dinitrophenyl)-L-α-β-diaminopropionyl) at the Gly-Leu bond, Mca fluorescence ($\lambda_{ex}$=340 nm, $\lambda_{em}$=400 nm) was measured at 60-second intervals for 20 min. Experiments were repeated at least three times. $IC_{50}$ values were calculated as the inhibitor concentration at which the enzyme is at 50% control activity (no inhibitor present).

The inhibitory activity of compounds AM-1 through AM-6 was evaluated using the fluorescence-based assay; the $IC_{50}$ values are listed in Table 4.

TABLE 4

$IC_{50}$ Values (μM) for MPIs Against MMP-1, MMP-2, and MMP-3 are Shown

| Inhibitor | MMP-1 | MMP-2 | MMP-3 |
|---|---|---|---|
| AM-1 | >50 | 36 (5) | >50 |
| AM-2 | >50 | 9.3 (0.5) | 0.24 (0.01) |
| AM-3 | >50 | 27 (2) | 36 (1) |
| AM-4 | >50 | >50 | 2.4 (0.2) |
| AM-5 | >50 | 0.61 (0.01) | 0.010 (0.002) |
| AM-6 | >50 | >50 | 0.019 (0.002) |
| 20 | >12.5 | 0.9 | 0.56 |
| AM-2/NH | — | — | 0.943 |
| PY-Stil | — | — | 0.071 |

TABLE 5

Average $IC_{50}$ values (μM) against metalloenzymes.

| Compound | LF | HDAC |
|---|---|---|
| PY-2S (27) | 38 (5) | |
| PY-3S (30) | 18.5 (1.4) | |
| 1,2-HOPTO | 3900 (200) | 860 (100) |
| Thiomaltol | 260 (30) | 247 (12) |
| AHA (N-hydroxyacetamide) | 11400 (1000) | 3200 (300) |

AM-2, AM-5, and AM-6 were the most potent compounds against MMP-3, with $IC_{50}$ values in the nanomolar range. Additional representative $IC_{50}$ values for MMP-3 inhibition include AM3: 90 μM; KA2: 200 μM; KA3: 930 μM; TKA3: 90 μM; KA4: 400 μM; and CA1: 25% inhibition at 50 μM. The pyrone-based MPIs are more potent than the analogous hydroxamate-based inhibitors, which is contrary to the accepted dogma that hydroxamic acids are the best ZBGs.[37, 39] As expected, the effects of linker length (compare AM-1, AM-2, and AM-3) and backbone substituents (AM-5 relative to AM-2) are consistent with analogous hydroxamate-based MPIs.[39] These results demonstrate that ZBGs equal or superior to hydroxamates can be identified and utilized in novel MPI designs.

The observed trends in the $IC_{50}$ values of the MPIs described here against MMP-3 suggest that the large aromatic backbone substituents of these compounds occupy the S1' subsite. This hypothesis was further examined by determining the selectivity of these compounds against different MMPs. All six MPIs were found to be poor inhibitors of MMP-1 (Table 4).

The inhibitors were also tested for potency against MMP-2. Like MMP-3, MMP-2 has a deep S1' pocket, and potency against these two enzymes is expected to be comparable, as found with hydroxamate-based MPIs. (140) Interestingly, although AM-2, AM-4, AM-5, and AM-6 showed a range of potencies against MMP-3, all four compounds were substantially less potent against MMP-2. Indeed, AM-6 showed >2500-fold selectivity for MMP-3, which is the highest selectivity reported for an MPI for MMP-3 over MMP-2.

Cell Invasion Assay. A cell invasion assay kit was purchased from Chemicon International (Cat. No. ECM 555) and the assay was performed as per kit instructions with minor modifications. Rat cardiac fibroblasts (CF) were prepared as previously described (F. J. Villarreal, N. N. Kim, G. D. Ungab, M. P. Printz, W. H. Dillmann, *Circulation* 1993, 88, 2849). Briefly, CF were prepared from hearts of 1-2 day old Sprague Dawley rats. Following collagenase digestions (4×), non-myocyte cells (mostly fibroblasts) were isolated by Percoll density gradient. The cell suspension was plated onto uncoated tissue culture dishes for 30 min to allow preferential attachment of CF to the bottom of the dish. The non-adherent cells were removed and fresh media (Dulbecco's modified Eagle's media+10% fetal bovine serum) was added. CF were allowed to proliferate to confluence and then trypsinized and frozen at −70° C. Stocks were freshly plated for the experiment and used from second passage. When reaching 90% confluence, cells were serum deprived for 24 h and then treated according to the experimental design (vide infra).

The CF were trypsinized once more and suspended in fresh serum-free media. Inhibitors AM-5 and AM-6 were dissolved in DMSO and diluted 10-fold in serum free media. The inhibitor solution (2 μL) was added to 100 μL of the cell suspension. The cell suspension containing inhibitors was added to the upper chamber of the well. Media with 10% fetal bovine serum (as chemoattractant) was added to the lower chamber of the well. The plate was incubated for 20 h in a $CO_2$ incubator (10% $CO_2$). The cells that had invaded into the lower chamber were dislodged from the underside of the ECMatrix™ membrane and lysed. The lysed cells were treated with CyQuant GR Dye, and monitored for fluorescence using a Bio-Tek Flx 800 fluorescence plate reader and Nunc white 96-well plates ($\lambda_{ex}$=485 nm, $\lambda_{em}$=516 nm). Increased fluorescence indicates the presence of invaded cells.

Figure 7:
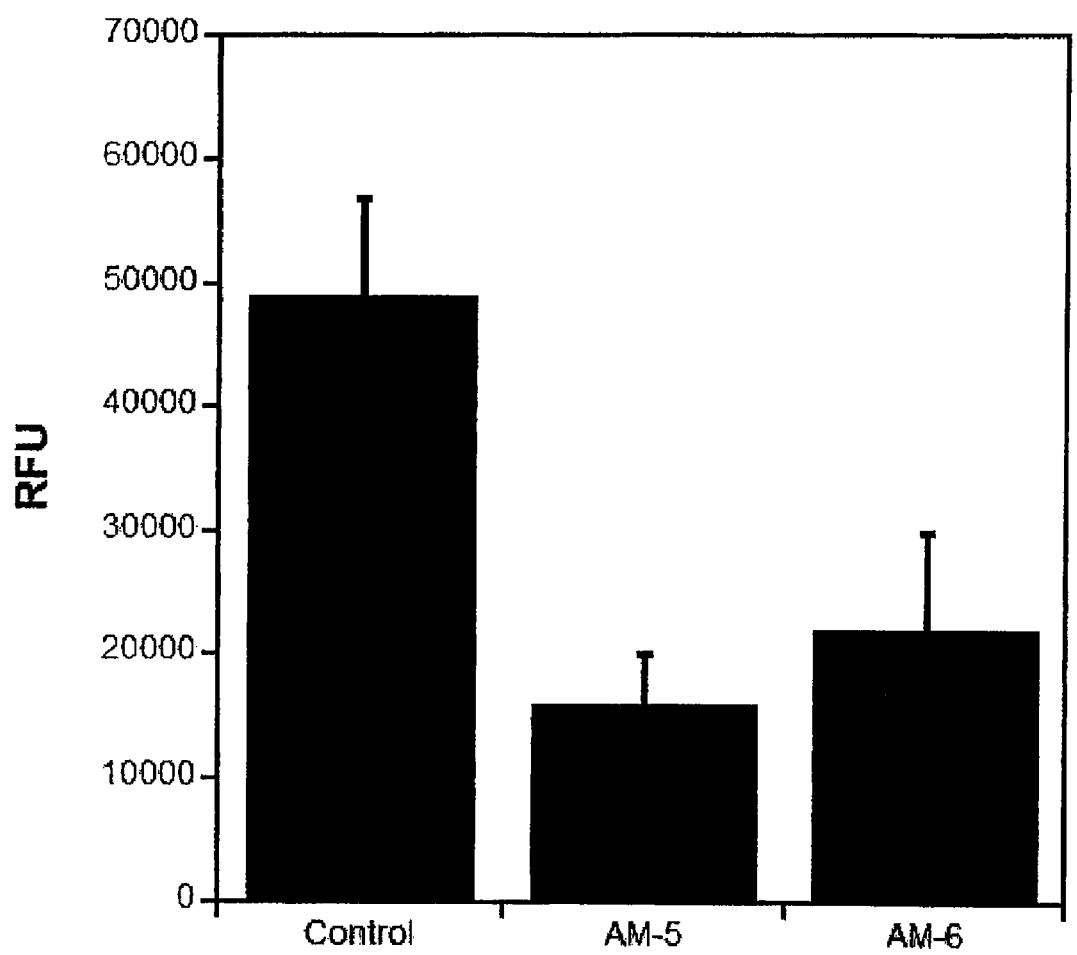
FIG. 7. Is a graph depicting the neonatal cardiac fibroblast (CF) invasion assay results. Fluorescent measurement in RFUs of lysed cells after invasion: no indicator (control), 250 nM AM-5 and 250 nM AM-6. Increased RFUs indicates increased cell invasion.

The ability of AM-5 and AM-6 to inhibit invasion of neonatal rat cardiac fibroblasts through a collagen membrane was examined, as a gauge of the in vivo potential of these MPIs. At a concentration of 250 nM, the two inhibitors were found to reduce invasion by 67% (AM-5) and 55% (AM-6) (FIG. 7).

The design of potent and selective metalloprotein inhibitors such as matrix metalloproteinase inhibitors presents the possibility to treat many diseases, including those disclosed in Refs. 1-3, incorporated by reference herein. The ZBGs specifically disclosed herein can readily be elaborated by adding a wide variety of substituents to the open ring positions, particularly peptidomimetic backbones, such as those shown in Reference 1 and in EPA 126,974.

REFERENCES (1) Whittaker, M.; Floyd, C. D.; Brown, P.; Gearing, A. J. H. *Chem. Rev.* 1999, 99, 2735-2776.

(2) Overall, C. M.; Lüpez-Otín, C. *Nat. Rev. Cancer* 2002, 2, 657-672.

(3) Puerta, D. T.; Cohen, A. *Curr. Top. Med. Chem.* 2004, 4, 1551-1573.
(4) Wegener, D.; Hildmann, C.; Schwienhorst, A. *Mol. Genet. Metab.* 2003, 80, 138-147.
(5) Grozinger, C. M.; Schreiber, S. L. *Chem. Biol.* 2002, 9, 3-16.
(6) Vigushin, D. M.; Coombes, R. C. *Anti-Cancer Drugs* 2002, 13, 1-13.
(7) Miller, T. A.; Witter, D. J.; Belvedere, S. *J. Med. Chem.* 2003, 46, 5098-5116.
(8) Johnstone, R. W. *Nat. Rev. Drug. Discov.* 2002, 1, 287-299.
(9) Park, J. M.; Greten, F. R.; Li, Z.-W.; Karin, M. *Science* 2002, 297, 2048-2051.
(10) Collier, R. J.; Young, J. A. T. *Anu. Rev. Cell Dev. Biol.* 2003, 19, 45-70.
(11) Pezard, C.; Berche, P.; Mock, M. *Infect. Immun.* 1991, 59, 3472-3477.
(12) Panchal, R. G.; Hermone, A. R.; Nguyen, T. L.; Wong, T. Y.; Schwarzenbacher, R.; Schmidt, J.; Lane, D.; McGrath, C.; Turk, B. E.; Burnett, J.; Aman, M. J.; Little, S.; Sausville, E. A.; Zaharevitz, D. W.; Cantley, L. C.; Liddington, R. C.; Gussio, R.; Bavari, S, *Nat. Struct. Mol. Biol.* 2004, 11, 67-72.
(13) Turk, B. E.; Wong, T. Y.; Schwarzenbacher, R.; Jarrell, E. T.; Leppla, S. H.; Collier, R. J.; Liddington, R. C.; Cantley, L. C. *Nature* 2004, 11, 60-66.
(14) Lee, L. V.; Bower, K. E.; Liang, F.-S.; Shi, J.; Wu, D.; Sucheck, S. J.; Vogt, P. K.; Wong, C.-H. *J. Am. Chem. Soc.* 2004, 126, 4774-4775.
(15) Agrawal, A.; Pulendran, B. *Cell. Mol. Life. Sci.* 2004, 61, 2859-2865.
(16) Puerta, D. T.; Cohen, S. M. *Inorg. Chem.* 2002, 41, 5075-5082.
(17) Puerta, D. T.; Cohen, S. M. *Inorg. Chem.* 2003, 42, 3423-3430.
(18) Parkin, G. *Chem. Commun.* 2000, 20.
(19) Trofimenko, S. *Chem. Rev.* 1993, 93, 943-980.
(20) Vahrenkamp, H. *Acc. Chem. Res.* 1999, 32, 589-596.
(21) Ruf, M.; Weis, K.; Brasack, I.; Vahrenkamp, H. *Inorg. Chim. Acta* 1996, 250, 271-281.
(22) Puerta, D. T.; Lewis, J. A.; Cohen, S. M. *J. Am. Chem. Soc.* 2004, 126, 8388-8389.
(23) Liu, Z. D.; Piyamongkol, S.; Liu, D. Y.; Khodr, H. H.; Lu, S. L.; Hider, R. C. *Bioorg. Med. Chem.* 2001, 9, 563-573.
(24) Aytemir, M. D.; Hider, R. C.; Erol, D. D.; Ekizoglu, M. O. M. Turk. *J. Chem.* 2003, 27, 445-452.
(25) Streater, M.; Taylor, P. D.; Hider, R. C.; Porter, J. *J. Med. Chem.* 1990, 33, 1749-1755.
(26) Puerta, D. T.; Schames, J. R.; Henchman, R. H.; McCammon, J. A.; Cohen, S. M. *Angew. Chem. Int. Ed.* 2003, 42, 3772-3774.
(27) Abu-Dari, K.; Karpishin, T. B.; Raymond, K. N. *Inorg. Chem.* 1993, 32, 3052-3055.
(28) Scarrow, R. C.; Riley, P. E.; Abu-Dari, K.; White, D. L.; Raymond, K. N. *Inorg. Chem.* 1985, 24, 954-967.
(29) Babine, R. E.; Bender, S. L. *Chem. Rev.* 1997, 97, 1359-1472.
(30) Thompson, K. H.; Orvig, C. In *Metal Ions in Biological Systems*; Sigel, A., Sigel, H., Eds.; Marcel Dekker, Inc.: New York, 2004; Vol. 41, pp 221-253.
(31) Lippard, S. J.; Berg, J. M. *Principles of Bioinorganic Chemistry*; University Science Books: Mill Valley, 1994.
(32) Sigel, H.; McCormick, D. B. *Chem. Rev.* 1970, 3, 201-208.
(33) Levin, J. I.; DiJoseph, J. F.; Killar, L. M.; Sharr, M. A.; Skotnicki, J. S.; Patel, D. V.; Xiao, X.-Y.; Shi, L.; Navre, M.; Campbell, D. A. *Bioorg. Med. Chem. Lett.* 1998, 8, 1163-1168.
(34) Campbell, D. A.; Xiao, X.-Y.; Harris, D.; Ida, S.; Mortezaei, R.; Ngu, K.; Shi, L.; Tien, D.; Wang, Y.; Navre, M.; Patel, D. V.; Sharr, M. A.; DiJoseph, J. F.; Killar, L. M.; Leone, C. L.; Levin, J. I.; Skotnicki, J. S. *Bioorg. Med. Chem. Lett.* 1998, 8, 1157-1162.
(35) Lewis, J. A.; Puerta, D. T.; Cohen, S. M. *Inorg. Chem.* 2003, 42, 7455-7459.
(36) Lewis, J. A.; Cohen, S. M. *Inorg. Chem.* 2004, 43, 6534-6536.
(37) Knight, C. G.; Willenbrock, F.; Murphy, G. *FEBS Lett.* 1992, 296, 263-266.
(38) Weingarten, H.; Martin, R.; Feder, J. *Biochemistry* 1985, 24, 6730-6734.
(39) P. Hajduk et al., *J. Amer. Chem. Soc.,* 119, 5818 (1997).
(40) J. W. Skiles et al., *Curr. Med. Chem.,* 11, 2911 (2004).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A metalloprotein inhibitor of formula (IA) or (IB):

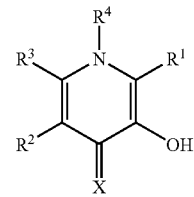

wherein X is O or S and
wherein $R^1$ is a group of the formula —C(=O)NHR$^{1'}$, wherein $R^{1'}$ is biphenyl, biphenyl($C_1$-$C_6$)alkyl, or phenoxyphenyl, wherein the —C(=O) group of $R^1$ is bonded directly to a ring carbon atom, wherein any phenyl can be independently substituted; and wherein $R^2$ is hydrogen, or is an unsubstituted ($C_1$-$C_6$)alkyl, ($C_3$-$C_6$)cycloalkyl, ($C_3$-$C_6$)cycloalkyl-($C_1$-$C_6$)alkyl), ($C_6$-$C_{10}$)aryl, ($C_6$-$C_{10}$)aryl-($C_2$-$C_{10}$)alkyl, and $R^3$ is hydrogen, or is an unsubstituted ($C_1$-$C_6$)alkyl, hydroxy($C_1$-$C_6$)alkyl or ($C_1$-$C_6$)alkanoyloxy, and $R^4$, when present, is hydrogen, or is an unsubstituted ($C_1$-$C_6$)alkyl, ($C_3$-$C_6$)cycloalkyl, ($C_3$-$C_6$)cycloalkyl-($C_1$-$C_6$)alkyl), ($C_6$-$C_{10}$)aryl, or ($C_6$-$C_{10}$)aryl-($C_2$-$C_{10}$)alkyl; provided that $R^2$ and $R^3$ are not both hydrogen; and provided that when X is O for a compound of formula (IA) that $R^3$ is not methyl;
or a pharmaceutically-acceptable salt thereof.

2. The inhibitor of claim 1 wherein $R^{1'}$ is biphenyl($C_1$-$C_6$) alkyl, wherein the alkyl group is bonded directly to the NH of the —C(=O)NH moiety.

3. The inhibitor of claim 1 wherein $R^{1'}$ is biphenylmethyl, wherein the methyl group is bonded directly to the NH of the —C(=O)NH moiety.

4. The inhibitor of claim 2 of formula (IA) wherein X is O.

* * * * *

UNITED STATES PATENT AND TRADEMARK OFFICE
CERTIFICATE OF CORRECTION

PATENT NO. : 7,786,316 B2  
APPLICATION NO. : 12/503190  
DATED : August 31, 2010  
INVENTOR(S) : David T. Puerta et al.

It is certified that error appears in the above-identified patent and that said Letters Patent is hereby corrected as shown below:

On the Title Pg on page 2, Item (56) under "Other Publications", line 21, delete "Applicatiion" and insert -- Application --, therefor.

On the Title Pg on page 2, Item (56) under "Other Publications", line 23, delete "Applicatiion" and insert -- Application --, therefor.

On the Title Pg on page 2, Item (56) under "Other Publications", line 44, delete "Pyronecarboxylic" and insert -- Pyrenecarboxylic --, therefor.

On the Title Pg on page 2, Item (56) under "Other Publications", line 51, delete "Doman" and insert -- Domain --, therefor.

On the Title Pg on page 2, Item (56) under "Other Publications", line 19, delete "Medicial" and insert -- Medical --, therefor.

On the Title Pg on page 2, Item (56) under "Other Publications", lines 36-37, delete "Mettaloproteinase" and insert -- Metalloproteinase --, therefor.

On the Title Pg on page 2, Item (56) under "Other Publications", line 60, before "Suppl." insert -- ( --.

On the Title Pg on page 3, Item (56) under "Other Publications", line 13, delete "Biorbanic" and insert -- Bioorganic --, therefor.

In column 2, line 31, delete "animoglycosides" and insert -- aminoglycosides --, therefor.

In column 4, line 63, after "minutes" insert -- . --.

In column 6, line 44, delete "((" and insert -- ( --, therefor.

In column 8, line 20, delete "$CH^3$." and insert -- $CH_3$. --, therefor.

Signed and Sealed this

Thirtieth Day of November, 2010

David J. Kappos  
*Director of the United States Patent and Trademark Office*

CERTIFICATE OF CORRECTION (continued)

In column 12, line 21, delete "dilutent" and insert -- diluent --, therefor.

In column 15, line 9, delete "polaxomers," and insert -- poloxamer, --, therefor.

In column 20, line 24, after "$P_4S_{10}$" insert -- . --.

In column 21, line 16, delete "(6" and insert -- ($d^6$ --, therefor.

In column 21, line 21, delete "4(1)" and insert -- 4(1H) --, therefor.

In column 21, line 27, delete "(6" and insert -- ($d^6$ --, therefor.

In column 21, line 31, delete "(6" and insert -- ($d^6$ --, therefor.

In column 22, line 49, delete "$C_{21}H_{19}NO_4$ $0.20H_2O$:" and insert -- $C_{21}H_{19}NO_4$•$0.20H_2O$: --, therefor.

In column 23, lines 5-10, delete " 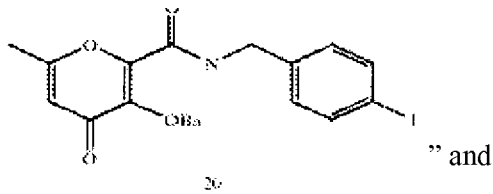 " and insert -- 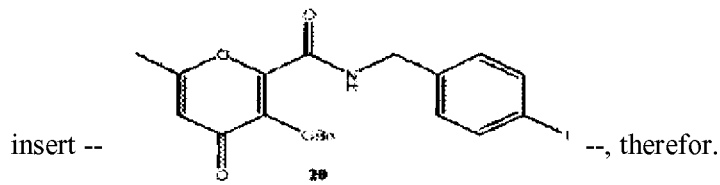 --, therefor.

In column 23, line 30, after "60-91%" insert -- . --.

In column 23, lines 35-36, delete "N-hydroxysuccinamide" and insert -- N-hydroxysuccinimide --, therefor.

In column 24, line 20, after "2H)" delete "." and insert -- , --, therefor.

In column 24, line 26, delete ".$1.5H_2O$" and insert -- •1.5 $H_2O$ --, therefor.

In column 24, line 44, before "1H)," delete "HZ," and insert -- Hz, --, therefor.

In column 24, line 44, before "2H)," delete "HZ," and insert -- Hz, --, therefor.

In column 24, line 46, delete "820.1," and insert -- δ 20.1, --, therefor.

In column 24, line 47, after "135.0" insert -- , --.

In column 24, line 66, delete ".$0.9H_2O$:" and insert -- •0.9 $H_2O$: --, therefor.

In column 25, line 47, after "CDCl₃)" insert -- : --.

In column 26, line 61, delete "CH₂))," and insert -- CH₂), --, therefor.

In column 26, line 65, delete "(2.8" and insert -- δ 2.8 --, therefor.

In column 26, line 66, delete "NH))," and insert -- NH), --, therefor.

In column 27, line 51, delete "CH2Cl2," and insert -- CH₂Cl₂, --, therefor.

In column 28, line 24, delete "CH₂))," and insert -- CH₂), --, therefor.

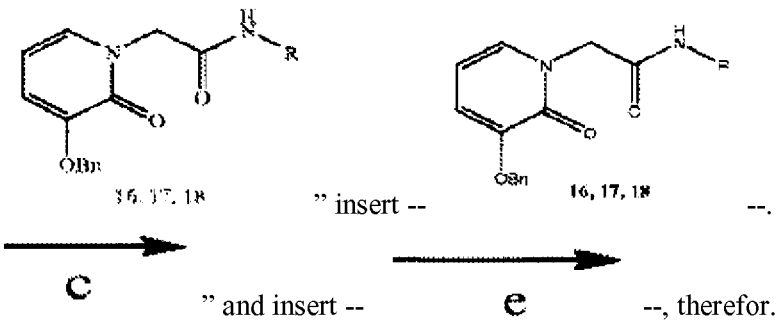

In column 29, lines 1-5, before " " insert -- --.

In column 29, lines 1-5, delete " " and insert -- --, therefor.

In column 29, line 58, after "Yield" delete ":".

In column 30, line 7, after "Yield" delete ":".

In column 30, line 25, after "Yield" delete ":".

In column 30, line 32, delete ".½H₂O:" and insert -- •½ H₂O: --, therefor.

In column 30, line 46, after "Yield" delete ":".

In column 30, line 63, after "Yield" delete ":".

In column 31, line 19, after "Yield" delete ":".

In column 31, line 37, after "Yield" delete ":".

In column 32, line 11, delete "dryed" and insert -- dried --, therefor.

In column 32, line 21, after "(400 MHz)" insert -- : --.

In column 32, line 23, delete "calcd" and insert -- Calcd --, therefor.

In column 32, line 24, after "C₁₉H₁₆N₂O₃" insert -- : --.

In column 32, line 63, delete "40-mL" and insert -- 40 mL --, therefor.

In column 33, line 8, before "2.22" delete "δ:" and insert -- : δ --, therefor.

In column 33, line 9, delete "6.12, (s, 1H, CH)" and insert-- 6.12 (s, 1H, CH), --, therefor.

In column 33, line 10, after "(ESI)" insert -- : --.

In column 33, line 16, delete "100-mL" and insert -- 100 mL --, therefor.

In column 33, line 23, after "(DMSO-d$_6$)" delete "δ:" and insert -- : δ --, therefor.

In column 33, line 25, after "m/z" insert -- = --.

In column 34, lines 1-15, delete " 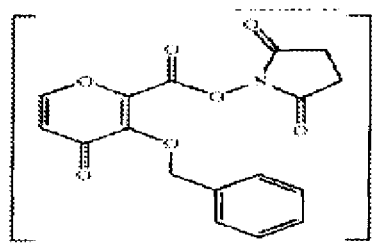 " and insert -- 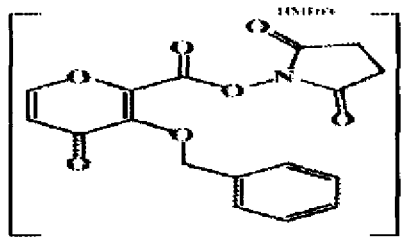 --, therefor.

In column 35, line 6, delete "A:" and insert -- Δ: --, therefor.

In column 35, line 30, after "Yield" delete ":".

In column 36, line 16, after "Yield" delete ":".

In column 36, line 22, delete "A:" and insert -- Δ: --, therefor.

In column 36, line 43, after "Yield" delete ":".

In column 36, line 58, after "Yield" delete ":".

In column 37, line 18, after "Yield" delete ":".

In column 37, line 33, after "Yield" delete ":".

In column 38, line 48, delete "111 mL" and insert -- 11 mL --, therefor.

CERTIFICATE OF CORRECTION (continued)

In column 38, line 49, delete "N-hydroxysuccinamide" and insert -- N-hydroxysuccinimide --, therefor.

In column 38, line 57, delete "111 mL" and insert -- 11 mL --, therefor.

In column 38, line 67, after "(DMSO-$d_6$)" delete "δ:" and insert -- : δ --, therefor.

In column 39, line 12, after "(DMSO-$d_6$)" delete "δ:" and insert -- : δ --, therefor.

In column 39, line 16, after "(DMSO-$d_6$)" delete "δ:" and insert -- : δ --, therefor.

In column 39, line 19, delete "ELI" and insert -- EI --, therefor.

In column 40, line 21, delete "N-hydroxysuccinamide" and insert -- N-hydroxysuccinimide --, therefor.

In column 40, line 29, delete "111 mL" and insert -- 11 mL --, therefor.

In column 40, line 42, after "(Acet-$d_6$)" delete "δ:" and insert -- : δ --, therefor.

In column 40, line 62, after "(DMSO-$d_6$)" delete "δ:" and insert -- : δ --, therefor.

In column 49, lines 27-28, delete "Accelyrs," and insert -- Accelrys, --, therefor.

In column 52, line 7, delete "(140)" and insert -- $^{(1,\,40)}$ --, therefor.

In column 53, line 30, after "Life" delete ".".

In column 53, line 59, in Claim 2, delete "$R^1$" and insert -- $R^{1'}$ --, therefor.